US011037658B2

(12) United States Patent
Cox et al.

(10) Patent No.: US 11,037,658 B2
(45) Date of Patent: Jun. 15, 2021

(54) CLINICAL CONDITION BASED COHORT IDENTIFICATION AND EVALUATION

(71) Applicant: International Business Machines Corporation, Armonk, NY (US)

(72) Inventors: James S. Cox, Plano, TX (US); Anthony J. DiGiorgio, Arlington, TX (US)

(73) Assignee: International Business Machines Corporation, Armonk, NY (US)

(*) Notice: Subject to any disclaimer, the term of this patent is extended or adjusted under 35 U.S.C. 154(b) by 1428 days.

(21) Appl. No.: 15/045,378

(22) Filed: Feb. 17, 2016

(65) Prior Publication Data

US 2017/0235893 A1   Aug. 17, 2017

(51) Int. Cl.
*G16H 10/60* (2018.01)
*G16H 40/67* (2018.01)
*G16H 70/20* (2018.01)

(52) U.S. Cl.
CPC ............. *G16H 10/60* (2018.01); *G16H 40/67* (2018.01); *G16H 70/20* (2018.01)

(58) Field of Classification Search
CPC ......... G16H 10/60; G06H 50/20; G06Q 50/22
(Continued)

(56) References Cited

U.S. PATENT DOCUMENTS 5,199,439 A   4/1993 Zimmerman et al.
5,819,228 A   10/1998 Spiro
(Continued)

FOREIGN PATENT DOCUMENTS

CN   101676921 A   3/2010
CN   101814111 A   8/2010
(Continued)

OTHER PUBLICATIONS

Rosenzweig et al., "Mindfulness-based stress reduction for chronic pain conditions: Variation in treatment outcomes and role of home meditation practice," Journal of Psychosomatic Research 68 (2010) pp. 29-36. (Year: 2010).*

(Continued)

*Primary Examiner* — Elaine Gort
*Assistant Examiner* — Jonathon A. Szumny
(74) *Attorney, Agent, or Firm* — Stephen J. Walder, Jr.; William J. Stock

(57) ABSTRACT

Mechanisms are provided for monitoring treatment of patients. The mechanisms generate a patient registry comprising a plurality of patient registry records, each patient registry record being associated with a corresponding patient and comprising attributes specifying personal and medical information about the corresponding patient. The mechanisms collect, for each patient registry record, treatment data regarding treatment of the corresponding patient. The mechanism analyzes the treatment data to identify successful treatments administered to the corresponding patients. The mechanisms generate one or more cohorts of corresponding patients based on attributes of the patient registry records associated with corresponding patients for which successful treatments were administered. The mechanisms perform at least one patient management operation based on the generated one or more cohorts.

18 Claims, 19 Drawing Sheets

(58) Field of Classification Search
USPC .......................................................... 705/2
See application file for complete search history.

(56) References Cited

U.S. PATENT DOCUMENTS

| | | | |
|---|---|---|---|
| 6,154,726 A | 11/2000 | Rensimer et al. |
| 6,173,068 B1 | 1/2001 | Prokoski |
| 6,611,846 B1 | 8/2003 | Stoodley |
| 6,915,254 B1 | 7/2005 | Heinze et al. |
| 7,167,855 B1 | 1/2007 | Koenig |
| 7,177,699 B2 | 2/2007 | Fabian et al. |
| 7,233,938 B2 | 6/2007 | Carus et al. |
| 7,315,825 B2 | 1/2008 | Rosenfeld et al. |
| 7,389,245 B1 | 6/2008 | Ashford et al. |
| 7,395,216 B2 | 7/2008 | Rosenfeld et al. |
| 7,493,253 B1 | 2/2009 | Ceusters et al. |
| 7,640,174 B2 | 12/2009 | Surpin et al. |
| 7,668,732 B1 | 2/2010 | Charles |
| 7,702,522 B1 | 4/2010 | Sholem |
| 7,716,067 B2 | 5/2010 | Surpin et al. |
| 7,752,035 B2 | 7/2010 | Oon |
| 7,765,114 B2 | 7/2010 | Frick |
| 7,949,544 B2 | 5/2011 | Miglietta et al. |
| RE42,508 E | 6/2011 | Lewis et al. |
| 7,967,749 B2 | 6/2011 | Hutchinson et al. |
| 7,996,240 B2 | 8/2011 | Canda |
| 8,010,717 B2 | 8/2011 | Evans et al. |
| 8,050,937 B1 | 11/2011 | Henderson |
| 8,060,377 B2 | 11/2011 | Dunham et al. |
| 8,099,305 B2 | 1/2012 | Kuo et al. |
| 8,135,470 B2 | 3/2012 | Keimel et al. |
| 8,208,619 B2 | 6/2012 | Perrin et al. |
| RE43,550 E | 7/2012 | Moore et al. |
| 8,260,636 B2 | 9/2012 | Grichnik et al. |
| 8,275,803 B2 | 9/2012 | Brown et al. |
| 8,316,237 B1 | 11/2012 | Felsher et al. |
| 8,346,804 B2 | 1/2013 | Phillips |
| 8,374,988 B2 | 2/2013 | Gawlick |
| 8,380,542 B2 | 2/2013 | Wons et al. |
| 8,417,662 B2 | 4/2013 | Gawlick |
| 8,515,780 B2 | 8/2013 | Soto et al. |
| 8,521,563 B2 | 8/2013 | Severin |
| 8,543,414 B2 | 9/2013 | Iwano |
| 8,554,195 B2 | 10/2013 | Rao |
| 8,571,889 B2 | 10/2013 | Ashford |
| 8,612,261 B1 | 12/2013 | Swanson et al. |
| 8,645,171 B2 | 2/2014 | Lutgen et al. |
| 8,663,104 B2 | 3/2014 | Iliff |
| 8,666,539 B2 | 3/2014 | Ervin |
| 8,666,763 B2 | 3/2014 | Fabius et al. |
| 8,666,926 B1 | 3/2014 | Nease et al. |
| 8,676,607 B2 | 3/2014 | Patel et al. |
| 8,681,009 B2 | 3/2014 | Pendse |
| 8,712,796 B2 | 4/2014 | Moore et al. |
| 8,725,538 B2 | 5/2014 | Kay |
| 8,725,539 B2 | 5/2014 | Romano et al. |
| 8,738,396 B2 | 5/2014 | Green, III et al. |
| 8,744,867 B2 | 6/2014 | Spertus |
| 8,751,257 B2 | 6/2014 | Amland et al. |
| 8,751,889 B2 | 6/2014 | Zhang et al. |
| 8,756,079 B2 | 6/2014 | Yegnanarayanan |
| 8,762,173 B2 | 6/2014 | Wasson et al. |
| 8,781,849 B1 | 7/2014 | Grossman |
| 8,781,853 B2 | 7/2014 | Green, III et al. |
| 8,781,859 B2 | 7/2014 | Manning et al. |
| 8,788,289 B2 | 7/2014 | Flanagan et al. |
| 8,799,023 B2 | 8/2014 | White et al. |
| 8,805,756 B2 | 8/2014 | Boss et al. |
| 8,832,808 B2 | 9/2014 | Liu et al. |
| 8,847,767 B2 | 9/2014 | Lim et al. |
| 8,852,093 B2 | 10/2014 | Clapp et al. |
| 8,880,454 B2 | 11/2014 | Christie, IV et al. |
| 8,886,587 B1 | 11/2014 | Hainsworth et al. |
| 8,930,223 B2 | 1/2015 | Friedlander et al. |
| 8,935,155 B2 | 1/2015 | Bretschneider et al. |
| 8,949,082 B2 | 2/2015 | Farooq et al. |
| 8,951,192 B2 | 2/2015 | Osorio |
| 8,984,017 B2 | 3/2015 | Naeymi-Rad et al. |
| 8,996,428 B2 | 3/2015 | Baras et al. |
| 9,008,385 B2 | 4/2015 | Baym et al. |
| 9,015,054 B2 | 4/2015 | Lara et al. |
| 9,064,040 B2 | 6/2015 | Sudharsan |
| 9,923,931 B1 | 3/2018 | Wagster et al. |
| 10,108,975 B1 | 10/2018 | Benner et al. |
| 2002/0029784 A1 | 3/2002 | Stark et al. |
| 2002/0128816 A1 | 9/2002 | Haug et al. |
| 2003/0105638 A1 | 6/2003 | Taira |
| 2003/0130595 A1 | 7/2003 | Mault |
| 2003/0225597 A1 | 12/2003 | Levine |
| 2004/0059196 A1 | 3/2004 | Abraham-Fuchs et al. |
| 2004/0059622 A1 | 3/2004 | Mueller |
| 2004/0133543 A1 | 7/2004 | Shlaes et al. |
| 2004/0204961 A1 | 10/2004 | Rensimer et al. |
| 2004/0249667 A1 | 12/2004 | Oon |
| 2005/0102159 A1 | 5/2005 | Mondshine |
| 2005/0144042 A1 | 6/2005 | Joffe et al. |
| 2006/0036619 A1 | 2/2006 | Fuerst et al. |
| 2006/0047538 A1 | 3/2006 | Condurso et al. |
| 2006/0080142 A1 | 4/2006 | Hart et al. |
| 2006/0116557 A1 | 6/2006 | Moore et al. |
| 2006/0129427 A1 | 6/2006 | Wennberg |
| 2007/0033072 A1 | 2/2007 | Bildirici |
| 2007/0061166 A1 | 3/2007 | Ramasubramanian et al. |
| 2007/0083396 A1 | 4/2007 | Kanada et al. |
| 2008/0010090 A1 | 1/2008 | Surpin et al. |
| 2008/0086327 A1 | 4/2008 | Cox et al. |
| 2008/0120138 A1 | 5/2008 | Morita et al. |
| 2008/0195417 A1 | 8/2008 | Surpin et al. |
| 2008/0195594 A1 | 8/2008 | Gerjets et al. |
| 2008/0201174 A1 | 8/2008 | Ramasubramanian et al. |
| 2008/0238666 A1 | 10/2008 | Loncar |
| 2008/0263050 A1 | 10/2008 | Randazzo et al. |
| 2009/0076845 A1* | 3/2009 | Bellin ................... G06Q 10/10 705/2 |
| 2009/0138285 A1* | 5/2009 | Denberg ............... A61B 5/0002 705/3 |
| 2009/0274286 A1 | 11/2009 | O'Shaughnessy et al. |
| 2009/0287678 A1 | 11/2009 | Brown et al. |
| 2009/0299767 A1 | 12/2009 | Michon et al. |
| 2010/0049756 A1 | 2/2010 | Chemitiganti et al. |
| 2010/0070293 A1 | 3/2010 | Brown et al. |
| 2010/0070306 A1 | 3/2010 | Dvorak et al. |
| 2010/0082369 A1 | 4/2010 | Prenelus et al. |
| 2010/0191071 A1 | 7/2010 | Anderson et al. |
| 2010/0198755 A1 | 8/2010 | Soll et al. |
| 2010/0268549 A1 | 10/2010 | Hicks et al. |
| 2010/0274584 A1 | 10/2010 | Kim |
| 2010/0286490 A1 | 11/2010 | Koverzin et al. |
| 2010/0324927 A1 | 12/2010 | Tinsley |
| 2010/0324936 A1 | 12/2010 | Venkata et al. |
| 2011/0004070 A1 | 1/2011 | Rist et al. |
| 2011/0054289 A1 | 3/2011 | Derchak et al. |
| 2011/0066587 A1 | 3/2011 | Ferrucci et al. |
| 2011/0071868 A1 | 3/2011 | Parker et al. |
| 2011/0077973 A1 | 3/2011 | Breitenstein et al. |
| 2011/0112855 A1 | 5/2011 | Chen et al. |
| 2011/0125734 A1 | 5/2011 | Duboue et al. |
| 2011/0161107 A1 | 6/2011 | Goldberg et al. |
| 2011/0191122 A1 | 8/2011 | Kharraz Tavakol et al. |
| 2011/0202490 A1 | 8/2011 | Gawlick |
| 2011/0238439 A1 | 9/2011 | Rice |
| 2011/0246220 A1 | 10/2011 | Albert |
| 2011/0313791 A1 | 12/2011 | Mault et al. |
| 2012/0004924 A1 | 1/2012 | Kachnowski et al. |
| 2012/0010900 A1 | 1/2012 | Kaniadakis |
| 2012/0016690 A1 | 1/2012 | Ramarajan et al. |
| 2012/0065987 A1* | 3/2012 | Farooq ................. G06F 19/328 705/2 |
| 2012/0084092 A1 | 4/2012 | Kozuch et al. |
| 2012/0089909 A1 | 4/2012 | Block et al. |
| 2012/0110016 A1 | 5/2012 | Phillips |
| 2012/0116806 A1 | 5/2012 | Stark et al. |
| 2012/0117092 A1 | 5/2012 | Stankiewicz et al. |
| 2012/0166212 A1 | 6/2012 | Campbell |

(56) References Cited

U.S. PATENT DOCUMENTS

| | | |
|---|---|---|
| 2012/0173265 A1 | 7/2012 | Brush et al. |
| 2012/0173273 A1 | 7/2012 | Ashford |
| 2012/0179480 A1 | 7/2012 | Patel et al. |
| 2012/0221350 A1* | 8/2012 | Kenedy .............. G09B 19/00 705/2 |
| 2012/0239590 A1 | 9/2012 | Broder et al. |
| 2012/0310661 A1 | 12/2012 | Greene |
| 2012/0316891 A1* | 12/2012 | Friedlander .......... G06F 19/325 705/2 |
| 2013/0007055 A1 | 1/2013 | Brown et al. |
| 2013/0018652 A1 | 1/2013 | Ferrucci et al. |
| 2013/0066886 A1 | 3/2013 | Bagchi et al. |
| 2013/0086069 A1 | 4/2013 | Phillips |
| 2013/0124226 A1 | 5/2013 | Gedala |
| 2013/0138450 A1 | 5/2013 | Vigneux |
| 2013/0179176 A1 | 7/2013 | Gotthardt |
| 2013/0179178 A1 | 7/2013 | Vemireddy et al. |
| 2013/0185108 A1 | 7/2013 | Bainbridge et al. |
| 2013/0197942 A1 | 8/2013 | Chiu et al. |
| 2013/0223606 A1 | 8/2013 | Lee |
| 2013/0226608 A1 | 8/2013 | DiLascia et al. |
| 2013/0226617 A1 | 8/2013 | Mok et al. |
| 2013/0246088 A1 | 9/2013 | Huster et al. |
| 2013/0262155 A1 | 10/2013 | Hinkamp |
| 2013/0297348 A1 | 11/2013 | Cardoza et al. |
| 2013/0311193 A1 | 11/2013 | Know et al. |
| 2013/0311201 A1 | 11/2013 | Chatfield et al. |
| 2013/0346105 A1 | 12/2013 | Ryan et al. |
| 2014/0025393 A1 | 1/2014 | Wang et al. |
| 2014/0025687 A1 | 1/2014 | Aleksovski et al. |
| 2014/0052470 A1 | 2/2014 | Ashford |
| 2014/0081623 A1 | 3/2014 | Bretschneider et al. |
| 2014/0095201 A1 | 4/2014 | Farooq et al. |
| 2014/0100882 A1 | 4/2014 | Hamilton et al. |
| 2014/0100885 A1 | 4/2014 | Stern |
| 2014/0108024 A1 | 4/2014 | Evans et al. |
| 2014/0108048 A1 | 4/2014 | Cohn |
| 2014/0142924 A1 | 5/2014 | Friedman |
| 2014/0164005 A1 | 6/2014 | Merkin |
| 2014/0164784 A1* | 6/2014 | Sinderbrand ......... G06F 21/602 713/189 |
| 2014/0221785 A1 | 8/2014 | Pacione et al. |
| 2014/0236630 A1 | 8/2014 | Murata |
| 2014/0244292 A1 | 8/2014 | Rosenberg et al. |
| 2014/0257838 A1 | 9/2014 | Karra et al. |
| 2014/0278475 A1 | 9/2014 | Tran |
| 2014/0278544 A1 | 9/2014 | Khurana et al. |
| 2014/0288970 A1 | 9/2014 | Lee et al. |
| 2014/0297301 A1 | 10/2014 | Rock |
| 2014/0324457 A1 | 10/2014 | Kim et al. |
| 2014/0324467 A1 | 10/2014 | Hayes |
| 2014/0330581 A1 | 11/2014 | Billings et al. |
| 2014/0330586 A1 | 11/2014 | Riskin et al. |
| 2014/0343961 A1 | 11/2014 | Thesman |
| 2014/0348318 A1 | 11/2014 | Talapady et al. |
| 2014/0379366 A1 | 12/2014 | Alloway et al. |
| 2015/0006192 A1 | 1/2015 | Sudharsan et al. |
| 2015/0012295 A1 | 1/2015 | Mahoney |
| 2015/0019247 A1 | 1/2015 | Stedillie |
| 2015/0019257 A1 | 1/2015 | Doyle et al. |
| 2015/0088536 A1 | 3/2015 | Thelen et al. |
| 2015/0088548 A1 | 3/2015 | Charlot et al. |
| 2015/0095016 A1 | 4/2015 | Karres et al. |
| 2015/0095044 A1 | 4/2015 | Hartman et al. |
| 2015/0100327 A1 | 4/2015 | Kelly et al. |
| 2015/0100343 A1 | 4/2015 | Siedlecki et al. |
| 2015/0106123 A1 | 4/2015 | Amarasingham et al. |
| 2015/0112703 A1 | 4/2015 | Sysko et al. |
| 2015/0112721 A1 | 4/2015 | Bloodsworth, Jr. |
| 2015/0112726 A1 | 4/2015 | Miglietta et al. |
| 2015/0142701 A1 | 5/2015 | Ashparie et al. |
| 2015/0154372 A1 | 6/2015 | Soenksen et al. |
| 2015/0161535 A1 | 6/2015 | Ptashek et al. |
| 2015/0190098 A1 | 7/2015 | Patek et al. |
| 2015/0213225 A1 | 7/2015 | Amarasingham et al. |
| 2015/0254407 A1 | 9/2015 | Sporleder |
| 2015/0261922 A1 | 9/2015 | Nawana et al. |
| 2015/0347705 A1 | 12/2015 | Simon et al. |
| 2015/0363566 A1 | 12/2015 | Johnson et al. |
| 2016/0042306 A1 | 2/2016 | Emerson et al. |
| 2016/0063209 A1 | 3/2016 | Malaviya |
| 2016/0098536 A1 | 4/2016 | Dettinger et al. |
| 2016/0210426 A1 | 7/2016 | Robinson et al. |
| 2016/0232328 A1 | 8/2016 | Sklar et al. |
| 2016/0328530 A1 | 11/2016 | Felemban et al. |
| 2016/0350501 A1 | 12/2016 | Rothschild et al. |
| 2016/0357910 A1 | 12/2016 | Ghouri et al. |
| 2017/0024546 A1 | 1/2017 | Schmidt |
| 2017/0061091 A1 | 3/2017 | McElhinney et al. |
| 2017/0091391 A1 | 3/2017 | LePendu |
| 2017/0098032 A1 | 4/2017 | Desai et al. |
| 2017/0116388 A1 | 4/2017 | Robinson |
| 2017/0193171 A1 | 7/2017 | Perloroth et al. |
| 2017/0220757 A1 | 8/2017 | Cox et al. |
| 2017/0220758 A1 | 8/2017 | Cox et al. |
| 2017/0235885 A1 | 8/2017 | Cox |
| 2017/0235906 A1 | 8/2017 | Dorris et al. |
| 2017/0236063 A1 | 8/2017 | Dorris et al. |
| 2017/0262604 A1 | 9/2017 | Francois |
| 2019/0095629 A1 | 3/2019 | Lee et al. |
| 2019/0110754 A1 | 4/2019 | Rao et al. |
| 2019/0130110 A1 | 5/2019 | Lee et al. |
| 2019/0188562 A1 | 6/2019 | Edwards et al. |

FOREIGN PATENT DOCUMENTS

| | | |
|---|---|---|
| CN | 103455961 A | 12/2013 |
| CN | 104834989 A | 8/2015 |
| GB | 2507812 A | 11/2012 |
| JP | 2005-258994 A | 9/2005 |
| JP | 2005-349088 A | 12/2005 |
| JP | 2008-229172 A | 10/2008 |
| WO | WO2009/134587 A2 | 11/2009 |

OTHER PUBLICATIONS

Workman, Thomas A., "Engaging Patients in Information Sharing and Data Collection: The Role of Patient-Powered Registries and Research Networks", Agency of Healthcare Research and Quality, AHRQ Publication No. 13-EHC124-EF Sep. 2013, 18 pages.

"ICD-10 Code Translator", https://www.aapc.vom/icd-10/codes/, Accessed from the Internet on Nov. 20, 2015, 4 pages.

List of IBM Patents or Patent Applications Treated as Related, Apr. 28, 2016, 2 pages.

"Capitation (healthcare)", Wikipedia.org, https://en.wikipedia.org/wiki/Capitation_(healthcare), last modified on Jun. 30, 2015, accessed on Oct. 26, 2015, 3 pages.

"Clinical Language Understanding", Clinical Language Understanding & EHR Structured Data, Nuance Healthcare, http://www.nuance.com/for-healthcare/resources/clinical-language-understanding/index.htm, Accessed from the Internet on Nov. 10, 2015, 3 pages.

"Course 12: Convert CPT Codes to ICD-9 Codes for Medical Billing and Coding", Understanding Current Procedural Technology (CPT) Codes, Medical Billing and Coding Online, A guide of CPT to ICD-9 codes, Accessed from the Internet on Nov. 6, 2015, http://www.medicalbillingandcodingonline.com/cpt-to-icd-coding/, 4 pages.

"Healthcare risk assessment made easy", Reference No. 0555, Issue date Mar. 1, 2007, http://www.nrls,npsa.nhs.uk/resources/?EntryId45=59825, Accessed from the Internet on Nov. 6, 2015, 1 page.

"Measured Outcomes; A Video on Value-Based Healthcare", HealthCatalyst, https://www.healthcatalyst.com/videos/measured-outcomes-a-future-view-of-value-based-healthcare/?mkt_tok=3RkMMJWWfF9wsRogvKjKZKXonjHpfsX66uslWaG0IMI%2F0ER3fOvrPUfGjI4GRMZnI%2BSLDwEYGJIv6SgFQrDDMaNy37gIUhE%3D, Accessed from the Internet on Oct. 27, 2015, 2 pages.

"Patient Registration System", Kramer Technologies, http://www.kramergroup.com/patient-registration-system.html, accessed online Sep. 25, 2015, 1 page.

(56) References Cited

OTHER PUBLICATIONS

"Risk Assessment—8P, Project BOOST Implementation Toolkit", Touch Points: Admission, During Hospitalization, and Discharge, http://www.hospitalmedicine.org/Web/Quality_Innovation/Implementation_Toolkits/Project_BOOST/Web/Quality_Innovation/Implementation_Toolkit/Boost/BOOST_Intervention/Tools/Risk_Assessment.aspx Accessed from the Internet on Nov. 10, 2015, 2 pages.

"United Healthcare ICD-10-CM Code Lookup Tool", ICD Sep. 2010, https://icd10codelookup.smartbaselink.com/, Accessed from the Internet on Nov. 6, 2015, 1 page.

Hagland, Mark, "How Does Your Doctor Get Paid? The Controversy Over Capitation", PBS.org, http://www.pbs.org/wgbh/pages/frontline/shows/doctor/care/capitation.html, accessed on Oct. 26, 2015, 3 pages.

High, Rob, "The Era of Cognitive Systems: An Inside Look at IBM Watson and How it Works", IBM Corporation, Redbooks, Dec. 12, 2012, 16 pages.

McCord, M.C. et al., "Deep parsing in Watson", IBM J, Res. & Dev. vol. 56 No. 3/4 Paper 3, May/Jul. 2012, pp. 3:1-3:15.

Mell, Peter et al., "The NIST Definition of Cloud Computing", National Institute of Standards and Technology, Information Technology Laboratory, Draft, Version 15, Oct. 7, 2009, 2 pages.

Petro, Joe, "Natural language processing in electronic health records", Tech, Sep. 1, 2011, KevinMD.com, http://www.kevinmd.com/blog/2011/09/natural-language-processing-electronic-health-records.html, 3 pages.

Sox, Holly F., "What is a Careplan?", https://www.careplans.com/pages/about.aspx, accessed from the Internet on Nov. 3, 2015, 2 pages.

Sud, Heather et al., "Developing a risk-assessment tool to improve patient safety", Nursing Times, http://www.nursingtimes.net/nursing-practice/specialisms/infection-control/developing-a-risk-assessment-tool-to-improve-patient-safety/1833916.article, Sep. 4, 2008, 8 pages.

Thomas, Anil A. et al., Extracting Data from Electronic Medical Records: Validation of a Natural Language Processing Program to Assess Prostate Biopsy Results, World J Urol, Feb. 2014, 32(1), http://www.ncbi.nlm.nih.gov/pubmed/23417341, Abstract, 1 page.

Townsend, Hilary, "The Promise and Progress of NLP for Improved Care", Natural Language Processing and Clinical Outcomes, Journal of AHIMA, 84, No. 2, Mar. 2013, http://library.ahima.org/xpedio/groups/public/documents/ahima/bok1_050082,hcsp?dDocName=bok1_050082, 3 pages.

Wilson, John W. et al., "Hospital Rules-Based System: The Next Generation of Medical informatics for Patient Safety", http://www.medscape.com/viewarticle/502843, Accessed online Sep. 25, 2015, 12 pages.

Yuan, Michael J., "Watson and Healthcare, How natural language processing and semantic search could revolutionize clinical decision support", IBM Corporation, developerWorks, http://www.ibm.com/developerworks/industry/library/ind-watson/, Apr. 12, 2011, pp. 1-14.

Das, Ajay et al., "Supplier integration—Finding an optimal configuration", ScienceDirect Elsevier Journal of Operations Management vol. 24, Issue 5, Sep. 2006, pp. 563-582, 20 pages.

Han, Hyun-Soo et al., "Analyzing the impact of a firm's capability on outsourcing success: A process perspective", ScienceDirect Elsevier Information and Management, vol. 45, Issue 1, Jan. 2008, pp. 31-42.

Paulraj, Antony et al., "Inter-organizational communication as a relational competency: Antecedents and performance outcomes in collaborative buyer-supplier relationships", ScienceDirect Elsevier Journal of Operations Management 26 (2008) 45-64, 20 pages.

Pavlo, Andrew et al., "A Comparison of Approaches to Large-Scale Data Analysis", ACM (DL) Digital Library, SIGMOD '09, Proceedings of the 2009 ACM SIGMOD International Conference on Management of Data, pp. 165-178, Jun. 29-Jul. 2, 14 pages.

International Search Report and Written Opinion dated Jun. 22, 2017 for International Application No. PCT/IB2017/051036, 11 pages.

List of IBM Patents or Patent Applications Treated as Related, Sep. 5, 2017, 2 pages.

Ball, C J et al., "A Comparison of Communication Modes in Adult Psychiatry", Journal of Telemedicine and Telecare, Jan. 1995, pp. 22-26.

Takahashi, Akira et al., "Standardization Activities in the ITU for a QoE assessment of IPTV", Published in IEEE Communications Magazine (vol. 46, Issue 2, Feb. 2008), 7 Pages.

Dillman, Don A. et al., "Response rate and measurement differences in mixed-mode surveys using mail, telephone, interactive voice response (IVR) and the Internet", Social Science Research 38 (2009), Available online May 12, 2008, 18 pages.

\* cited by examiner

CODE TABLE – POP DM-1 HEDIS

PHYTEL CODES | CONTRACT CODES | PROTOCOLS | ICD/CPT OPTIONS

STANDARD CODES:

| CODING SYSTEM | CODE | CODE DESCRIPTION | REASON | REQ. |
|---|---|---|---|---|
| 19 | 250 | DIABETES MELLITUS | HEDIS 2011 | PHYTEL |
| 19 | 250.0 | DIABETES MELLITUS W/O COMPLICATION | HEDIS 2011 | PHYTEL |
| 19 | 250.00 | DIABETES MELLITUS (NIDDM) | HEDIS 2011 | PHYTEL |
| 19 | 250.01 | DIABETES MELLITUS W/O COMPLICATION TYPE I (... | HEDIS 2011 | PHYTEL |
| 19 | 250.02 | DIABETES MELLITUS W/O COMPLICATION TYPE II (... | HEDIS 2011 | PHYTEL |
| 19 | 250.03 | DIABETES MELLITUS W/O COMPLICATION TYPE I (... | HEDIS 2011 | PHYTEL |
| 19 | 250.1 | DIABETES WITH KETOACIDOSIS | HEDIS 2011 | PHYTEL |
| 19 | 250.10 | DIABETES WITH KETOACIDOSIS TYPE II OR UNSPE... | HEDIS 2011 | PHYTEL |
| 19 | 250.11 | DIABETES WITH KETOACIDOSIS TYPE I (JUVENILE... | HEDIS 2011 | PHYTEL |
| 19 | 250.12 | DIABETES WITH KETOACIDOSIS TYPE II OR UNSPE... | HEDIS 2011 | PHYTEL |
| 19 | 250.13 | DIABETES WITH KETOACIDOSIS TYPE I (JUVENILE... | HEDIS 2011 | PHYTEL |
| 19 | 250.2 | DIABETES WITH HYPEROSMOLARITY | HEDIS 2011 | PHYTEL |
| 19 | 250.20 | DIABETES WITH HYPEROSMOLARITY TYPE II OR... | HEDIS 2011 | PHYTEL |
| 19 | 250.21 | DIABETES WITH HYPEROSMOLARITY TYPE I (JUVE... | HEDIS 2011 | PHYTEL |
| ... | ... | ... | ... | ... |

IMPORT...    SAVE    SAVE & CLOSE    CANCEL

*FIG. 9A*

Diabetes - HEDIS

- Diabetes - HEDIS
  - All Of
    - Pts 18-75
  - Any Of
    - Two ICD/EM combinations
    - One ICD/EM combination
  - DM Problem
    - All Of
      - Diabetes Problem
    - Not Any Of
      - Secondary Diabetes
        - Any Of
          - Polycystic Ovaries
          - StDM or GDM
        - Not Any Of
          - Diabetes ICD

Rule Name
Diabetes - HEDIS

Short Name
pDM_HEDIS

Keywords

---

Variables | Rule Criteria

CODE RULE

Title: Two ICE/EM combinations

Code Table: Pop DM-1 INSIGHT

Look Back | Set Variable Name | Multiple Instances (Combo – 2 Instances

☑ Child Rule Enabled

*Are Multiple Instances/Codes Required?*
○ No, single instance of code qualifies.
● Yes, requires at least [2] instances [1] days apart.

☑ Code must have a combo to qualify

Code Table
ENC-27

[Add...]

[OK] [CANCEL]

FIG. 9C

Select Parent Rules

Rule Name
Diabetes HbA1C Poor Control (>9%)

Short Name
sDM_A1C_UNC

Select at least one parent from available rules:

Available Parent Rules
pDM_HEDIS
sDM_Health
sDM_A1C
sDM_Health_INVERSE

ALL of these (*)

AND ANY of these (*)
sDM_A1C_INVERSE
sDM_A1C_VH

AND NOT in any of these

* At least one parent rule required

Available Sibling Rules
sDM_A1C_C8
sDM_A1C_H

OK    CANCEL

*FIG. 9D*

CLINICAL CONDITION BASED COHORT IDENTIFICATION AND EVALUATION

BACKGROUND

The present application relates generally to an improved data processing apparatus and method and more specifically to mechanisms for generating clinical condition based cohorts and evaluating patients based on such clinical condition based cohort generation.

Monitoring patients with chronic illnesses, such as congestive heart failure, diabetes, and asthma represents one of the greatest challenges facing modern medicine. Patients with chronic illnesses require ongoing, follow-up treatment and care to properly manage their conditions. Unfortunately, a number of these patients do not receive ongoing treatment and care, receive treatment and care on a sporadic basis, or receive treatment and care which is not in accordance with recommended guidelines. Worse, patients often fail to do the basic simple day-to-day tasks that could prevent or reduce the frequency and magnitude of a catastrophic event such as a hospitalization. As a result, these patients often unnecessarily suffer from symptoms of their chronic illness which would have been minimized or prevented with proper ongoing treatment and care. Additionally, some of these patients may later require hospitalization, or in severe cases some of these patients may die, both of which may have been prevented if the patient was receiving the proper ongoing treatment and care.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method is provided, in a data processing system comprising a processor and a memory for monitoring treatment of patients. The method comprises generating, by the data processing system, a patient registry comprising a plurality of patient registry records, each patient registry record being associated with a corresponding patient and comprising attributes specifying personal and medical information about the corresponding patient. The method further comprises collecting, by the data processing system, for each patient registry record, treatment data regarding treatment of the corresponding patient. In addition, the method comprises analyzing, by the data processing system, the treatment data to identify successful treatments administered to the corresponding patients. Moreover, the method comprises generating, by the data processing system, one or more cohorts of corresponding patients based on attributes of the patient registry records associated with corresponding patients for which successful treatments were administered. The method also comprises performing, by the data processing system, at least one patient management operation based on the generated one or more cohorts.

In other illustrative embodiments, a computer program product comprising a computer useable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE DRAWINGS

The invention, as well as a preferred mode of use and further objectives and advantages thereof, will best be understood by reference to the following detailed description of illustrative embodiments when read in conjunction with the accompanying drawings, wherein:

FIGS. 9A-9D are diagrams illustrating example graphical user interfaces for rule generation in accordance with one illustrative embodiment;

DETAILED DESCRIPTION

Figure 1:
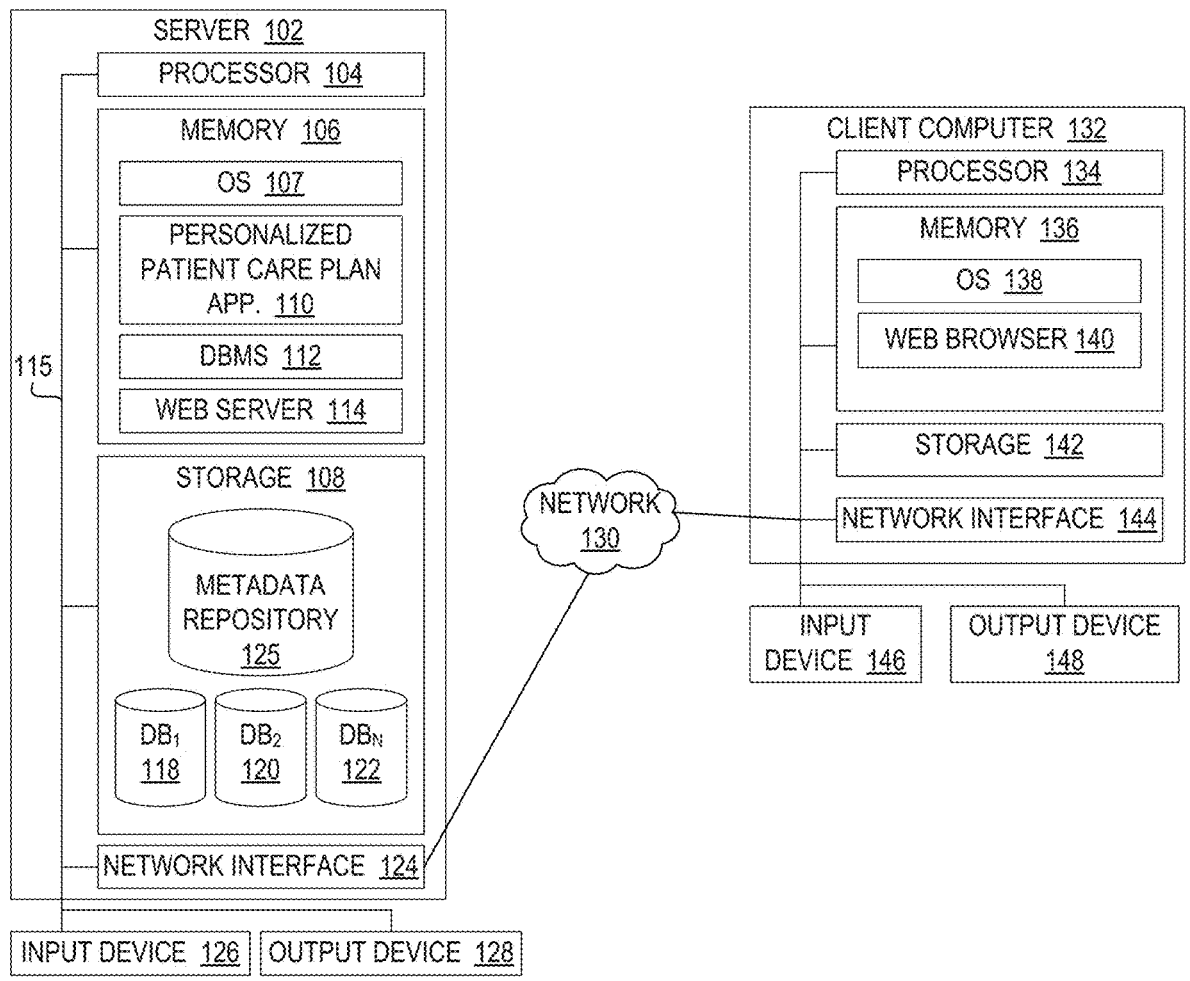
FIG. 1 is a block diagram illustrating a cloud computing system 100 for providing software as a service, where a server provides applications and stores data for multiple clients in databases according to one example embodiment of the invention.

Before beginning the discussion of the various aspects of the illustrative embodiments, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general purpose hardware, a procedure or method for executing the functions, or a combination of any of the above.

The present description and claims may make use of the terms "a", "at least one of", and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

In the following description, reference is made to embodiments of the invention. However, it should be understood that the invention is not limited to specific described embodiments. Instead, any combination of the following features and elements, whether related to different embodiments or not, is contemplated to implement and practice the invention. Furthermore, although embodiments of the invention may achieve advantages over other possible solutions and/or over the prior art, whether or not a particular advantage is achieved by a given embodiment is not limiting of the invention. Thus, the following aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

In addition, it should be appreciated that the present description uses a plurality of various examples for various elements of the illustrative embodiments to further illustrate example implementations of the illustrative embodiments and to aid in the understanding of the mechanisms of the illustrative embodiments. These examples are intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

Overview

As noted above, providing treatment and care for patients having illness requiring ongoing treatment is a major issue in modern medicine. Many times this ongoing treatment and care is a shared responsibility between the medical workers, e.g., doctors, nurses, etc. and the patient. That is, the patient must perform certain actions on their own to provide self-treatment for the illness, which often involves making different lifestyle choices, e.g., changing diet, increasing physical activity, taking prescribed medications, eliminating habits and consumption of products that are detrimental to health, etc., with the medical workers providing monitoring and periodic checks of the patient's progress to ensure that the patient is adhering to the treatment needed to control and/or improve the patient's condition.

A number of mechanisms have been developed for assisting the patient and medical workers in handling their shared responsibilities including mechanisms for generating patient care plans based on the patient's medical condition, mechanisms for patient's to self-monitor their adherence to their own care plans, and the like. Such mechanisms often regard patients as generic types of patients, e.g., a generic asthma patient, a generic diabetes patient, etc. possibly with some classification within these generic categories based on the patient's age, gender, race, and other generic demographics. Even with such classification within the generic categories, the resulting care plan associated with the patient is one that is applicable to multiple patients having the same set of medical diagnosis and demographics. The care plan is not in fact personalized to the specific patient but to a general categorization of the patient.

Each individual patient has a specific and different set of lifestyle conditions that make that patient unique from other patients. It is this uniqueness that is not reflected in the patient care plans generated by known mechanisms.

That is, the known patient care plan mechanisms are created to classify patients into generic categories and apply generic care plans to these patients. While mechanisms employing such patient care plan mechanisms may refer to them as being "personalized" or "customized" to the patient, they in fact are only superficially customized in that they may be customized based on generic customization categories, e.g., customized based on generic demographics such as age, race, gender, etc. As a result, patients are not in fact presented with a patient care plan that the patient feels is specifically suited to them. The patient care plans do not in fact take into account the patient's own individual circumstances and can be applied to a plurality of patients having the same demographics and medical condition, e.g., all 40 year old female diabetes patients. There are no mechanisms that personalize a patient's on-going treatment and care based on both their medical condition and the patient's own personal lifestyle, taking into account multiple lifestyle conditions and the facilities and resources available to that particular patient based on their lifestyle.

It should be appreciated that the term "lifestyle" as it is used herein refers to the way in which a person lives their lives. The term "lifestyle information" refers to the data collected that characterizes the lifestyle of the patient and may encompass various temporal, spatial, environmental, and behavioral information/data about the patient that together comprises a unique combination of information/data that characterizes and represents the way in which that specific patient conducts their life on a daily basis. The lifestyle information for a patient is specific to that patient and is not generally applicable to multiple patients. The lifestyle information may be provided at various levels of granularity depending upon the particular implementation. As part of this lifestyle information, data generated by the specific patient via one or more computing devices or other data communication devices may be included such as actions performed by the patient on a daily basis, personal schedules, specifications of preferences, etc. For example, lifestyle information may include the patient entering information, such as into a computing device executing a patient tracking application, indicating that the patient ate breakfast at a fast food restaurant in the airport on the way to Virginia this morning. In addition, data generated by external systems associated with third parties that characterizes the patient's lifestyle may be included in the lifestyle information as well, e.g., a healthcare insurance company may have information about the patient's lifestyle, e.g., smoker, overweight, sedentary, high risk for diabetes, etc., which may be characteristic of the patient's lifestyle.

For example, with regard to temporal lifestyle information, the lifestyle information may comprise one or more data structures specifying one or more schedules of events that the patient undergoes either on a routine basis or on a dynamic basis, e.g., a baseline routine schedule that may be dynamically updated as events occur or do not occur. The temporal lifestyle information may comprise, for example, the time that the patient wakes in the morning, when they have their meals, when they go to work and return home, when they take their children to school, when they shop for groceries, when they go to bed at night, scheduled non-routine events, free time, scheduled flight, ferry, train, or other ground transportation departure/arrival times, and/or any other temporal information characteristic of the patient's daily life and other non-routine scheduled events.

With regard to spatial lifestyle information, this information may comprise one or more data structures identifying locations associated with the patient's daily lifestyle including routine locations frequented by the patient, e.g., the location of their home, the location of their work, the location of their child's school, the location of the retail establishments that they frequent, the location of their doctors, the typical travel paths between locations utilized by the patient, and the like. The spatial lifestyle information may further comprise information about each location including the number of stories or levels in the buildings, e.g., two-story home, five-story office building, etc., whether the location has stairs, etc. The spatial lifestyle information may further comprise geographic information including the city, state, county, country, etc., in which the patient lives, works, travels to, or otherwise conducts their life.

With regard to environmental lifestyle information, this information comprises one or more data structures with indications of the environmental quality and resource availability in the environments in which the patient is present, is predicted to be present at a later time (such as based on the temporal and spatial lifestyle information), or typically is present on a daily or routine basis. For example, environmental lifestyle information may include information about the patient's home location, e.g., in a rural, urban, or suburban environment, has access to parks, walking trails, etc. This environmental lifestyle information may include information about the patient's work location including whether the patient works in an office setting with fluorescent lights and relative quiet, in a manufacturing setting with heavy machinery and loud noises, works with computers the majority of the day, has his/her own office or is in a cubicle, the number of co-workers the patient has that they interface with on a daily basis, the types and/or identities of establishments around the patient's home/work for purposes of determining access to resources (e.g., products and services), air quality, weather conditions, elevation (for purposes of oxygen level determination, for example), and the like.

Regarding behavioral lifestyle information, this information comprises one or more data structures having indications of the patient's own behavior and likes/dislikes, i.e. lifestyle preferences. The behavioral lifestyle information may comprise such information as the patient's habits, responses to communications of different modalities, patterns of activity, and the like. For example, such behavioral lifestyle information may indicate that the patient has a habit of eating a snack every evening after 9 p.m. or takes his/her dog for a walk in the mornings before 9 a.m. and after 5 p.m. The behavioral lifestyle information may further indicate the patient's likes and dislikes (preferences) with regard to various elements of daily life including types of foods the patient likes/dislikes, types of physical activity the patient likes/dislikes, when the patient likes to engage in certain activities, e.g., exercising before work/after work, or the like.

The various lifestyle information data may be obtained directly from the patient, such as via an electronic questionnaire, through analysis of electronic medical records (EMRs) or other entries in databases associated with the patient (e.g., governmental databases associated with a patient's social security number, address, or the like), or otherwise obtained from one or more monitoring devices and/or applications utilized on one or more computing devices associated with the patient and with which the patient interacts, e.g., patient tracking applications on a smart phone, a medical monitoring device, or the like, that monitors physical activity, food logs, and the like. This lifestyle information may be generated from static information and may also be dynamically updated on a periodic or constant basis to obtain the most current lifestyle information representative of the patient's current lifestyle. The lifestyle information is utilized to customize or personalize a patient care plan for the specific patient such that the patient is presented with a resulting patient care plan that the patient feels is tailored specifically to them and they way they conduct their lives.

In addition to known patient care plan mechanism suffering from the drawback of not in fact generating personalized patient care plans taking into account a patient's unique lifestyle, the known patient care plan mechanisms also do not provide for the ability to integrate third-party information about the lifestyle of a patient into the patient care plan personalization such that a more complete understanding of the capabilities of the patient based on their lifestyle is realized when generating and monitoring the patient's adherence to the patient care plan. For example, third-party lifestyle information may comprise information from commercial and governmental computing systems, databases, and the like, that characterize the patient's environment, availability to resources (e.g., products/services/facilities), etc., or is otherwise ancillary and further defining of other lifestyle information associated with the patient.

As one example, a third-party lifestyle information source may comprise a global positioning system (GPS) source that identifies the patient's associated locations, e.g., home, work, etc., and identifies establishments around those locations that provide resources that are of interest to the patient's lifestyle and potentially of interest in generating a patient care plan. For example, specialty grocery stores, vitamin stores, pharmacies, restaurants, gyms, walking paths, parks, recreational areas, community pools, and the like, may be identified based on a GPS system and its associated databases of information. This information may include identifications of types (e.g., Vietnamese Restaurant) and specific identities of the particular establishments which can be used with other third-party lifestyle information sources (e.g., a particular restaurant's website comprising menu and nutrition information) to retrieve specific information about those identified establishments. For example, a particular restaurant may be determined to be within a specified distance of the patient's home location and corresponding restaurant menu item information and hours of operation information may be retrieved from that particular restaurant's website, computing system, or other database. The retrieved menu item information and hours of operation information may be used, as described hereafter, to correlate the information with patient care plan information, e.g., nutritional and caloric information may be correlated with the patient care plan, to generate patient care plan actions/tasks and/or recommendations for assisting the patient in adhering to the patient's personalized patient care plan. Similarly, other third-party lifestyle information sources may provide information for correlation with patient care plan actions/tasks including hours of operations, products/services provided, distance from the patient's locations, and the like.

The illustrative embodiments of the present invention collect patient demographic and medical data, such as from questionnaires, electronic medical records, and the like, and generate a baseline patient care plan based on an initial diagnosis of the patient's medical condition, one or more categorizations of the patient based on the collected demographic and medical data, established patient care plan guidelines, and goals to be achieved by the patient care plan. Thus, for example, a patient's demographic information and electronic medical records may indicate that the patient is a 40 year old female that has been diagnosed with diabetes. Various pre-established categories and sub-categories may be defined for different types of patients in an ontology based on the various demographic and medical history characteristics, e.g., a category for diabetes patients, a sub-category of patients in the age range of 40 to 50 years old, a sub-sub-category of female patients, and so on.

Similarly, treatment guidelines may be established for defining ways in which to treat various medical maladies with these treatment guidelines having various triggering patient characteristics. For example, a treatment guideline may specify that for female diabetes patients that are in the age range of 40 to 60 years old, the patient should follow a low sugar diet and have at least 30 minutes of stressful exercise per day. A database of such treatments and their guidelines may be provided that correlates various combinations of patient characteristics with a corresponding treatment. Thus, by categorizing the patient in accordance with their characteristic information as obtained from demographic and medical data for the patient, these categories may be used to evaluate the applicability of the various treatments by matching the categories with the patient characteristics of the treatments to identify the best treatment for the patient, i.e. the treatment having the most matches between the patient categories and the treatment's required patient characteristics.

At this point, a general patient care plan is generated for the patient that identifies the treatment, which may be an on-going treatment, which should be prescribed for the patient. A patient care plan in this context is essentially a set of goals and actions for achieving those goals. As will be described hereafter, in addition, the present invention includes, in a patient care plan, a patient monitoring plan with specific actions to be taken on the part of an assessor to monitor and interface with the patient to elicit positive results from the patient, e.g., adherence to the patient care plan.

While a general patient care plan is present at this point, the general patient care plan has not yet been personalized or customized to the specific patient's unique lifestyle information. That is, while in general a 40 year old female diabetes patient should follow a low sugar diet with 30 minutes of stressful exercise each day, not every patient's lifestyle will accommodate such actions in the same way.

The illustrative embodiments further operate to personalize the general patient care plan to the particular lifestyle of the specific patient. Lifestyle information data is obtained from various sources to obtain an overall representation of the lifestyle of the patient. Examples of such sources include geospatial information sources, weather information sources, commercial establishment websites or computing devices/databases, governmental or regulatory organization information sources, and the like.

A patient's lifestyle information may also include data gathered from social media sources, including social media posts, comments, likes, browsing and other activity by the patient to determine their social circle, hobbies, likes, dislikes, interests, etc. This may include, but is not limited to, data from websites like Facebook™, Twitter™, Instagram™, Reddit™, Pinterest™, blog posts, and the like. Purchases and shopping activity are also a powerful indicators of lifestyle. Purchase data may include not only data about past purchases, but also shopping and activity online. Web browsing and search history similar to that used in driving online advertising can also be used to build lifestyle information and a lifestyle profile for a patient. Membership in customer loyalty programs from retail stores, grocery chains, and restaurants can also be used. Data that can be obtained from these programs may include membership, frequency of store visits, prior purchases, and the like. This data provides meaningful information about store, dining, grocery preferences, personal habits and schedules, and dietary data, among other information. This data may be used when building lifestyle information for the patient using products, goods, services, stores, and restaurants that the patient favors.

These third-party lifestyle information sources may provide lifestyle information that is combined with lifestyle information provided by the patient himself/herself for analysis to identify the types of personalized care plan actions to be used with the patient's care plan, the timing of the actions, and the types and timing of patient care plan monitoring and management actions to be performed by an assessor, e.g., a human assessor, automated assessment system, or a combination of human and automated assessment mechanisms. Thus, the selection of patient care plan actions (i.e. patient actions and monitoring actions) is based on the general patient care plan goals, the general patient care plan actions to be performed, and the personalization of these general patient care plan actions to the specific lifestyle of the patient.

Various lifestyle information analysis logic is provided to evaluate and classify the patient's lifestyle in accordance with a number of defined lifestyle categories. For example, the patient's lifestyle may be categorized according to level of physical activity, level of availability to healthy food sources, quality of home and work environment (lighting, air quality, quietness, safety, etc.), level of access to exercise facilities, various qualitative aspects of the patient's home and work life, and the like. From these categories, a more specific patient care plan is generated to achieve the goals and actions of the generic patient care plan, e.g., prescribe a specific type of diet plan which the patient has access to foods that meet with the diet plan and has a schedule that facilitates preparation of particular types of food.

For example, if the patient has limited time due to long work hours, having young children that require attention in the mornings/evenings before/after work, and the like, then food preparation time will be determined to be a minimum and thus, a corresponding diet plan will be selected for this particular type of lifestyle involving more processed foods than another patient that may have more time to perform more complex food preparation actions. Similarly, based on the patient's lifestyle information as obtained from the various sources, the mechanisms of the illustrative embodiments may prescribe a walking regimen based on the fact that the patient lives near a walking trail (as obtained from GPS data) and works in a building that has multiple floors (as obtained from patient supplied lifestyle information, GPS data, and/or governmental real estate databases) such that walking the stairs is an option. The patient's lifestyle information may further indicate an ability to prescribe a strength-building regimen since the patient lives near a gym (obtained from GPS data) or has gym facilities at their office (obtained from the patient supplied lifestyle information and/or real estate database information listing amenities of the building where the patient works). The timing of such actions may be specified in the patient care plan such that the walking regimen may instruct the patient to take a 25 minute walk at 8 a.m. every weekday and walk up/down the stairs at their office on their way to and from work and to and from lunch. The patient care plan may further specify that the patient is to go to the gym on Tuesday and Thursday at 7:30 p.m. to do 30 minutes of strength building exercise.

The granularity of the patient care plan may be even more specific depending upon the implementation. For example, with regard to a walking regimen, a particular path for the patient to walk may be specified in order to achieve a desired level of stress on the patient may be specified based on the geospatial information for the patient's home, work, and other locations, e.g., "Walk up Main Street to $2^{nd}$ Street, take a left, walk along $2^{nd}$ Street to Picard Street, take a left, walk down Picard Street to $1^{st}$ Street, take a left, and return to building." Such a path determination may be made based on information obtained about the geographical location of the patient's office building including the elevations of the streets to indicate uphill or downhill walking, distances, etc.

Because the lifestyle information may comprise specific establishment information, the patient care plan actions may be further personalized to the patient's particular locations and may specify particular establishments that can be frequented as well as what products/services the patient can utilize to be in compliance with the patient's prescribed care plan. For example, the menu items at a local restaurant may be analyzed to identify which menu items meet the diet requirements of the patient's care plan, e.g., low sugar foods, and the restaurant and its compliant menu items may be provided to the patient as part of their patient care plan. Personal trainer information for gyms may be obtained which includes the personal trainers' schedules, class schedules, and times of availability such that the patient may be instructed, as part of their personal patient care plan, when would be the best time for them to go to the gym to obtain personal trainer assistance with their strength building exercise regimen.

This more personalized patient care plan may further be customized to the specific lifestyle of the patient by evaluating the temporal lifestyle information and behavioral lifestyle information for the patient. Thus, having established a set of goals and actions to achieve those goals that are specific to the patient based on their demographics, medical data, and the patient's lifestyle information, the goals and actions may be converted to specific actions to be taken by the patient on a daily basis. For example, the patient's lifestyle information may be further analyzed to identify specific exercise actions to be taken by the patient based on their location, the facilities available, the patient's personal schedule of activities during the day, the patient's personal likes/dislikes (preferences), etc. For example, the patient may have a schedule that shows that the patient is available to exercise between 8 and 9 a.m. and 7:00 p.m. till 8:00 p.m. on most weekdays, is not available Thursday evenings after work for exercise, is available between 1 and 2 p.m. on Saturdays, and all day on Sundays. The preferences may further state that the patient does not like hot or rainy weather. The patient lifestyle information may further indicate that the patient likes to sleep late on Saturdays and Sundays and thus, while available early on these days, the mechanisms of the illustrative embodiments may adjust the scheduling of actions in the personalized care plan to accommodate this timing preference of the patient. Furthermore, the patient care plan may be dynamically adjusted based on determine weather and temperature conditions, e.g., instead of a standard walking regime that may have been previously part of the patient care plan, because the weather outside indicates a temperature of approximately 90 degrees and 20% chance of rain, the patient care plan may be adjusted to walking for 25 minutes in a neighborhood shopping mall.

It can be appreciated that because the lifestyle information that may be utilized to provide personalization of patient care plans is varied and vast, the types of personalizations that may be made to a patient care plan are likewise varied and vast. The patient care plan personalization mechanism of the illustrative embodiments provides logic for analyzing and evaluating a large set of lifestyle information data from various sources, determine specific patient care plan actions that meet the categorization and characterization of the patient's lifestyle as obtained from the analysis of the patient's lifestyle information, as well as achieves the goals and general actions associated with the generalized patient care plan corresponding to the patient's demographics and medical data, and compose the various personalized patient care plan actions into a series of actions to be taken by the patient over a set time period, e.g., daily, weekly, monthly, etc., in order to achieve desired goals of the patient care plan.

Thus, the illustrative embodiments provide various mechanisms for providing actual personalized patient care plans based not only on a categorization of the patient based on their medical diagnosis and demographic information, but also based on their own specific lifestyle information and lifestyle information obtained from third-party sources, e.g., information sources that provide information about a user's geographical surroundings, establishments in the user's geographical surroundings, event information sources, and the like. By personalizing the patient's care plan to their specific lifestyle, the likelihood that the patient will adhere to the care plan and perform the actions specified in the care plan is increased. Essentially, the personalized patient care plan helps to instruct the patient how the patient can integrate the care plan into their existing lifestyle without placing the burden on the patient to perform the analysis and evaluation on how to achieve such integration.

Having generated a personalized patient care plan taking into account the patient's personal lifestyle, the illustrative embodiments further provide mechanism for assisting and controlling the monitoring of a patient's adherence to the personalized care plan as well as assist health professionals, assessors, automated assessment systems, and the like, in performing actions and initiating communications to maintain ongoing treatment and care of the patient. Such mechanisms may involve evaluating the lifestyle information for the patient, the personalized care plan with its associated care plan actions, and determining appropriate monitoring actions/communications to be performed, timing of monitoring actions/communications, communication modes to be utilized, content of such communications, and the like, so as to maximize a positive response from the patient. Examples of such monitoring actions may be interrogating health monitoring devices and/or applications associated with the patient, e.g., wearable devices such as a FitBit™, pedometer, GPS device, applications running on a patient's smart phone or other computing device, or the like, initiating a reminder communication to be sent to the patient to remind them to perform an action in accordance with their personalized patient care plan, scheduling a doctor's appointment for the patient and informing them of the appointment, initiating a call to the patient's telephone to discuss their progress, or any other action that a human or automated assessment system may perform to assist with the monitoring of the patient's adherence to the patient's personalized patient care plan.

The particular monitoring actions to be employed are matched to the specific personalized patient care plan that is associated with the patient. That is, for each patient care plan action, there may be a set of one or more possible monitoring actions that may be associated with that type of patient care plan action. Selection from amongst the one or more possible monitoring actions may be performed based on an analysis of the patient's lifestyle information to determine the most appropriate monitoring action that will not interfere with the patient's lifestyle and will most likely result in a positive response from the patient. For example, if it is determined that the patient's lifestyle is such that the patient eats breakfast at 8:30 a.m. and one of the patient care plan actions is to eat oatmeal for breakfast three times a week, then a monitoring action may be selected that involves texting the patient with a message at 8:25 a.m., with the message having content that states "consider eating oatmeal for breakfast today." Other options may be to call the patient or send an electronic mail message but the patient's lifestyle information indicates that the patient is not a "morning person" and thus, is unlikely to respond well to calls in the morning and is generally in a rush to go to work since the patient eats breakfast at 8:30 a.m. and needs to be at the office by 9:30 a.m. indicating little time for checking electronic mail.

As with the personalized patient care plan, the monitoring plan and its monitoring actions, as well as their timing, may be personalized to the personalized patient care plan and the specific patient's lifestyle information. For example, if the patient works in a manufacturing environment where noise levels are high, it is unlikely that the patient will want to conduct a telephone conversation with a human assessor and is more likely to be responsive to textual communications. Thus, during working hours, monitoring actions may be restricted to textual communications, such as instant messaging or electronic mail. Similarly, if the patient works in a hospital, school, or other location where disturbances are to be minimized, communications may not be made during times of the day where the patient is likely to be present in such locations. Furthermore, as another example, if it is known that this particular patient weighs himself and takes his blood sugar measurements each morning at approximately 9:00 a.m., then a monitoring action may be to send a request to the electronic scale and/or blood sugar analysis mechanism to request the results of that day's measurements.

Thus, monitoring plans and corresponding monitoring actions are selected based on the patient's personalized patient care plan, the patient actions specified in the personalized patient care plan, and the lifestyle information for the particular patient. It should be appreciated that as the patient care plan changes over time, the monitoring plan also changes to match the changes to the patient care plan. Hence, in embodiments where the patient's personalized patient care plan is dynamically modified, such as in the case of dynamic changes based on weather, temperature, availability of facilities or resources, etc., the monitoring plan may likewise be dynamically modified.

In an even further aspect of the illustrative embodiments, the generation of the personalized care plan, and thus, the patient actions and monitoring actions of an assessor, may further take into consideration historical analysis of both the present patient and other similar patients with regard to previously prescribed patient care plans associated with these patients and their relative success/failure at adhering to these previously prescribed patient care plans and/or individual patient care plan actions that are part of these previously prescribed patient care plans. That is, historical analysis of patient information is performed across multiple patients to determine which care plans patients previously were able to adhere to, which care plans, and individual patient actions or tasks within patient care plans, resulted in successful outcomes for the patients, which resulted in unsuccessful outcomes for the patients, and generates a prediction as to the best patient care plans, patient actions or tasks, etc. to be given to future patients having similar attributes. This will result in patient care plans having tasks/actions for both the patient and the assessor that are tailored to the particular patient, as mentioned above, but in which previous success of other similar patients is taken into account when generating the personalized patient care plan. This historical analysis can be performed in the aggregate over a plurality of patients and/or on an individual basis based on what this particular patient has shown success, or lack thereof, with in the past.

For example, if it is determined that diabetic patients that are female, in the age range of 40-45, and are smokers tend to have negative results when their patient care plan involves strong cardiac exercise for 30 minutes a day (i.e., the patient tends to fail to complete this task), then future prescribed patient care plans may adjust based on this historical analysis. For example, the future patient care plans may reduce the requirement or substitute the requirement of the care plan, e.g., replace the patient action with one that requires mild cardiac exercise for 30 minutes a day. Alternatively, if it determined that diabetic patients that are female, in the age range of 40-45, and are smokers tend have positive results when their patient care plan involves drinking coffee and eating oatmeal for breakfast, then this may be added to future care plans for similar patients. Thus, adjustment of future patient care plans is made based on historical analysis of similar patient care plans and the patient's own history indicating positive results and adherence to previous patient care plans, e.g., if this particular patient has a history of failing to perform stressful exercise based patient actions in the past, then future patient care plans for this patient may be modified to not include stressful exercised based patient actions.

It should be appreciated that this historical evaluation may be performed at any point during the process of personalizing a patient care plan as previously described above. Thus, for example, in one illustrative embodiment, the historical analysis may be performed when generating the generalized patient care plan so as to identify the general goals and corresponding general patient care plan actions that previously have been most likely achieved by the current and other patients. In addition, either in the same or other illustrative embodiments, the historical analysis may be performed when personalizing the generic patient care plans based on the patient's lifestyle information. That is, historical analysis may be performed based on the patient's previous personalized patient care plans to determine what types of physical exercise actions the patient has previously been able to adhere to, which they have not been able to adhere to, or the like. In cases where similar patient care plan actions have not been previously prescribed for this patient, patient care plan information for similar patients, such as in a cohort of patients having similar demographics and medical data, may be analyzed to identify the patient actions that similar patients have been able to adhere to and utilize those as a basis for generating personalized patient actions in the personalized patient care plan for the present patient. Such actions may be personalized to the current patient's lifestyle in the manner previously described above. For example, assume that the general patient care plan calls for 30 minutes of stressful exercise which the patient has not been previously prescribed to perform, but similar patients have been able to adhere to 30 minutes of brisk walking a day and thus, this patient action is used as a basis for generating the present patient's general patient care plan. This action may then be personalized to the particular patient's lifestyle by generating specific personalized patient care plan actions for performing brisk walking at 8:00 a.m., along Hyde Street, for 25 minutes and then 5 minutes of stair walking at work on weekdays due to the patient working in a multi-story building.

In yet a further aspect of the illustrative embodiments, mechanisms are provided for dynamically adjusting or modifying personalized patient care plans based on a determined level of adherence to the personalized patient care plan, as determined from the monitoring actions performed and discussed above. That is, the patient's adherence to their personalized patient care plan is monitored and determinations are made as to whether the patient meets the goals set forth in the personalized patient care plan and/or performs the patient actions in the personalized patient care plan. If the patient does not meet the requirements of one or more goals in the patient care plan, an alternative goal determination logic is employed to determine an alternative goal that the patient is more likely to be able to accomplish. This determination may be made based on the patient's actual progress towards attaining the original goal, the importance and type of the goal to the overall personalized patient care plan, e.g., adjustments to medication may not be able to be made depending on the particular care plan, and a predetermined inter-changeability of the goals. In some cases, one goal may be adjusted in one direction, or by a first adjustment metric, and another in a different direction, or by a second adjustment metric, so as to balance the patient's ability to achieve a missed goal with an alternative goal while maintaining overall results that are to be generated, e.g., physical activity goal may be reduced while dietary goals may be increased so that the balance achieves the same overall effect. In this way, the patient's personalized patient care plan is further optimized for the particular patient based on the achievability of the goals for that particular patient.

In addition to finding alternative goals for a personalized patient care plan, alternative patient actions, and thus corresponding monitoring actions, may be identified for patient actions in the patient care plan that the patient has not been able to adhere to. In some illustrative embodiments, the determination of alternative care plan actions for performing the alternative goals may be based on a historical analysis of patient actions in other patient care plans that the patient and/or similar patients have undergone. This historical analysis may identify other similar patient actions that achieved similar results to the patient actions that the patient is found to not be able to achieve in the patient's current personalized patient care plan.

Thus, in general, as can be seen from the above description and examples, the mechanisms of the illustrative embodiments combine information about a patient's medical condition, medical history, lifestyle information, geographical location(s), facilities located in these geographical locations(s), products and services available in these geographical location(s), desired goals of the care plan, and other lifestyle information, and personalizes the patient care plan to the patient's particular medical condition, particular lifestyle, and available facilities and resources to provide a specific personalized patient care plan for this specific patient that is not widely applicable to generalized categories of patients.

This information may further be used to personalize the assessment activities to be performed by the assessment system/personnel and influence the timing, communication modes, and monitoring actions performed. That is, based on the particular care plan goals and care plan actions that are part of the patient's care plan, these goals/actions may be paired with monitoring actions to be taken by an assessor, e.g., a medical professional, other individual whose duty it is to monitor and interface with patients to ensure that they are following a prescribed care plan, or automated system. The monitoring actions may likewise be personalized based on the patient's lifestyle information, geographical information, available products and services in the patient's geographical area(s) of interest (e.g., home, work, etc.), and the like. The assessment tasks may be automatically or semi-automatically performed so as to gather information for monitoring the patient's adherence to the personalized patient care plan and either automatically or semi-automatically adjust the personalized patient care plan accordingly, send notifications to the patient, notify the doctor, or perform some other desired actions for maximizing the probability that the patient will maintain adherence to the personalized patient care plan.

It should be appreciated that the personalized patient care plans, and the personalized patient care plan actions (patient actions performed by the patient and monitoring actions performed by the assessor), may be dynamically adjusted based on the patient's current environmental conditions, changes in schedule, determined deviations from the care plan, and other dynamic conditions that may interfere or otherwise require modification, either temporarily or permanently, of the patient's personalized patient care plan. As noted above, such factors as weather conditions, temperature conditions, resource availability (e.g., gym is closed), and the like may require temporary modifications to a patient's personalized patient care plan. Other factors, such as the patient moving to a new location, obtaining a new place of employment, or the like, may require more permanent modifications to the patient's personalized patient care plan. Such factors may be identified and corresponding modifications initiated taking into account the new temporary/permanent lifestyle changes of the patient.

In some illustrative embodiments, the analysis of the various patient information for generating of a personalized care plan, modification of personalized care plans, determining appropriate actions to perform, sending communications and selecting communication modes, and the like, may be performed utilizing a hierarchical system of clinical rules defined based on standardized guidelines from health care providers, health care payment providers, best practices determined by subject matter experts, e.g., physicians and other medical personnel, the general knowledge of subject matter experts, and the like. In some embodiments, the clinical rules may be generated based on natural language processing of natural language text defining these guidelines, best practices, and other knowledge of subject matter experts. A graphical user interface may be provided for facilitating creation of the clinical rules utilizing an object oriented engine user interface elements. The graphical user interface permits the creation of such clinical rules without having to have expert medical knowledge. The clinical rules may be applied to a patient registry comprising electronic medical records, demographics information, lifestyle information, and the like, to classify patients into various cohorts based on their characteristics. These cohorts may be correlated to personalized care plans, actions or requirements to be part of personalized care plans, communication modes to utilize, and the like. Moreover, the clinical rules may be applied to patient information to determined care opportunities and what actions to be performed to improve the care provided to patients.

From the above general overview of the mechanisms of the illustrative embodiments, it is clear that the illustrative embodiments are implemented in a computing system environment and thus, the present invention may be implemented as a data processing system, a method implemented in a data processing system, and/or a computer program product that, when executed by one or more processors of one or more computing devices, causes the processor(s) to perform operations as described herein with regard to one or more of the illustrative embodiments. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As shown in the figures, and described hereafter, one or more computing devices comprising a distributed data processing system, may be specifically configured to implement a personalized patient care plan system in accordance with one or more of the illustrative embodiments. The configuring of the computing device(s) may comprise the providing of application specific hardware, firmware, or the like to facilitate the performance of the operations and generation of the outputs described herein with regard to the illustrative embodiments. The configuring of the computing device(s) may also, or alternatively, comprise the providing of software applications stored in one or more storage devices and loaded into memory of a computing device for causing one or more hardware processors of the computing device to execute the software applications that configure the processors to perform the operations and generate the outputs described herein with regard to the illustrative embodiments. Moreover, any combination of application specific hardware, firmware, software applications executed on hardware, or the like, may be used without departing from the spirit and scope of the illustrative embodiments.

It should be appreciated that once the computing device is configured in one of these ways, the computing device becomes a specialized computing device specifically configured to implement the mechanisms of one or more of the illustrative embodiments and is not a general purpose computing device. Moreover, as described hereafter, the implementation of the mechanisms of the illustrative embodiments improves the functionality of the computing device(s) and provides a useful and concrete result that facilitates creation, monitoring, and adjusting personalized patient care plans based on personalized lifestyle information and assessment of patient adherence to the personalized patient care plan.

As mentioned above, the mechanisms of the illustrative embodiments may be implemented in many different types of data processing systems, both stand-alone and distributed. Some illustrative embodiments implement the mechanisms described herein in a cloud computing environment. It should be understood in advance that although a detailed description on cloud computing is included herein, implementation of the teachings recited herein are not limited to a cloud computing environment. Rather, embodiments of the present invention are capable of being implemented in conjunction with any other type of computing environment now known or later developed. For convenience, the Detailed Description includes the following definitions which have been derived from the "Draft NIST Working Definition of Cloud Computing" by Peter Mell and Tim Grance, dated Oct. 7, 2009.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models. Characteristics of a cloud model are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service models of a cloud model are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment models of a cloud model are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes. A node in a cloud computing network is a computing device, including, but not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like. A cloud computing node is capable of being implemented and/or performing any of the functionality set forth hereinabove.

Personalized Care Plan Generation and Monitoring

FIG. 1 is a block diagram illustrating a cloud computing system 100 for providing software as a service, where a server provides applications and stores data for multiple clients in databases according to one example embodiment of the invention. The networked system 100 includes a server 102 and a client computer 132. The server 102 and client 132 are connected to each other via a network 130, and may be connected to other computers via the network 130. In general, the network 130 may be a telecommunications network and/or a wide area network (WAN). In a particular embodiment, the network 130 is the Internet.

The server 102 generally includes a processor 104 connected via a bus 115 to a memory 106, a network interface device 124, a storage 108, an input device 126, and an output device 128. The server 102 is generally under the control of an operating system 107. Examples of operating systems include UNIX, versions of the Microsoft Windows™ operating system, and distributions of the Linux™ operating system. More generally, any operating system supporting the functions disclosed herein may be used. The processor 104 is included to be representative of a single CPU, multiple CPUs, a single CPU having multiple processing cores, and the like. Similarly, the memory 106 may be a random access memory. While the memory 106 is shown as a single identity, it should be understood that the memory 106 may comprise a plurality of modules, and that the memory 106 may exist at multiple levels, from high speed registers and caches to lower speed but larger DRAM chips. The network interface device 124 may be any type of network communications device allowing the server 102 to communicate with other computers via the network 130.

The storage 108 may be a persistent storage device. Although the storage 108 is shown as a single unit, the storage 108 may be a combination of fixed and/or removable storage devices, such as fixed disc drives, solid state drives, floppy disc drives, tape drives, removable memory cards or optical storage. The memory 106 and the storage 108 may be part of one virtual address space spanning multiple primary and secondary storage devices.

As shown, the storage 108 of the server contains a plurality of databases. In this particular drawing, four databases are shown, although any number of databases may be stored in the storage 108 of server 102. Storage 108 is shown as containing databases numbered 118, 120, and 122, each corresponding to different types of patient related data, e.g., electronic medical records (EMRs) and demographic information, lifestyle information, treatment guidelines, personalized patient care plans, and the like, for facilitating the operations of the illustrative embodiments with regard to personalized patient care plan creation, monitoring, and modification. Storage 108 is also shown containing metadata repository 125, which stores identification information, pointers, system policies, and any other relevant information that describes the data stored in the various databases and facilitates processing and accessing the databases.

The input device 126 may be any device for providing input to the server 102. For example, a keyboard and/or a mouse may be used. The output device 128 may be any device for providing output to a user of the server 102. For example, the output device 108 may be any conventional display screen or set of speakers. Although shown separately from the input device 126, the output device 128 and input device 126 may be combined. For example, a display screen with an integrated touch-screen may be used.

As shown, the memory 106 of the server 102 includes a personalized patient care plan application 110 configured to provide a plurality of services to users via the network 130. As shown, the memory 106 of server 102 also contains a database management system (DBMS) 112 configured to manage a plurality of databases contained in the storage 108 of the server 102. The memory 106 of server 102 also contains a web server 114, which performs traditional web service functions, and may also provide application server functions (e.g. a J2EE application server) as runtime environments for different applications, such as the personalized patient care plan application 110.

As shown, client computer 132 contains a processor 134, memory 136, operating system 138, storage 142, network interface 144, input device 146, and output device 148, according to an embodiment of the invention. The description and functionality of these components is the same as the equivalent components described in reference to server 102. As shown, the memory 136 of client computer 132 also contains web browser 140, which is used to access services provided by server 102 in some embodiments.

The particular description in FIG. 1 is for illustrative purposes only and it should be understood that the invention is not limited to specific described embodiments, and any combination is contemplated to implement and practice the invention. Although FIG. 1 depicts a single server 102, embodiments of the invention contemplate any number of servers for providing the services and functionality described herein. Furthermore, although depicted together in server 102 in FIG. 1, the services and functions of the personalized patient care plan application 110 may be housed in separate physical servers, or separate virtual servers within the same server. The personalized patient care plan application 110, in some embodiments, may be deployed in multiple instances in a computing cluster. As is known to those of ordinary skill in the art, the modules performing their respective functions for the personalized patient care plan application 110 may be housed in the same server, on different servers, or any combination thereof. The items in storage, such as metadata repository 125, databases 118, 120, and 122, may also be stored in the same server, on different servers, or in any combination thereof, and may also reside on the same or different servers as the application modules.

Figure 2:
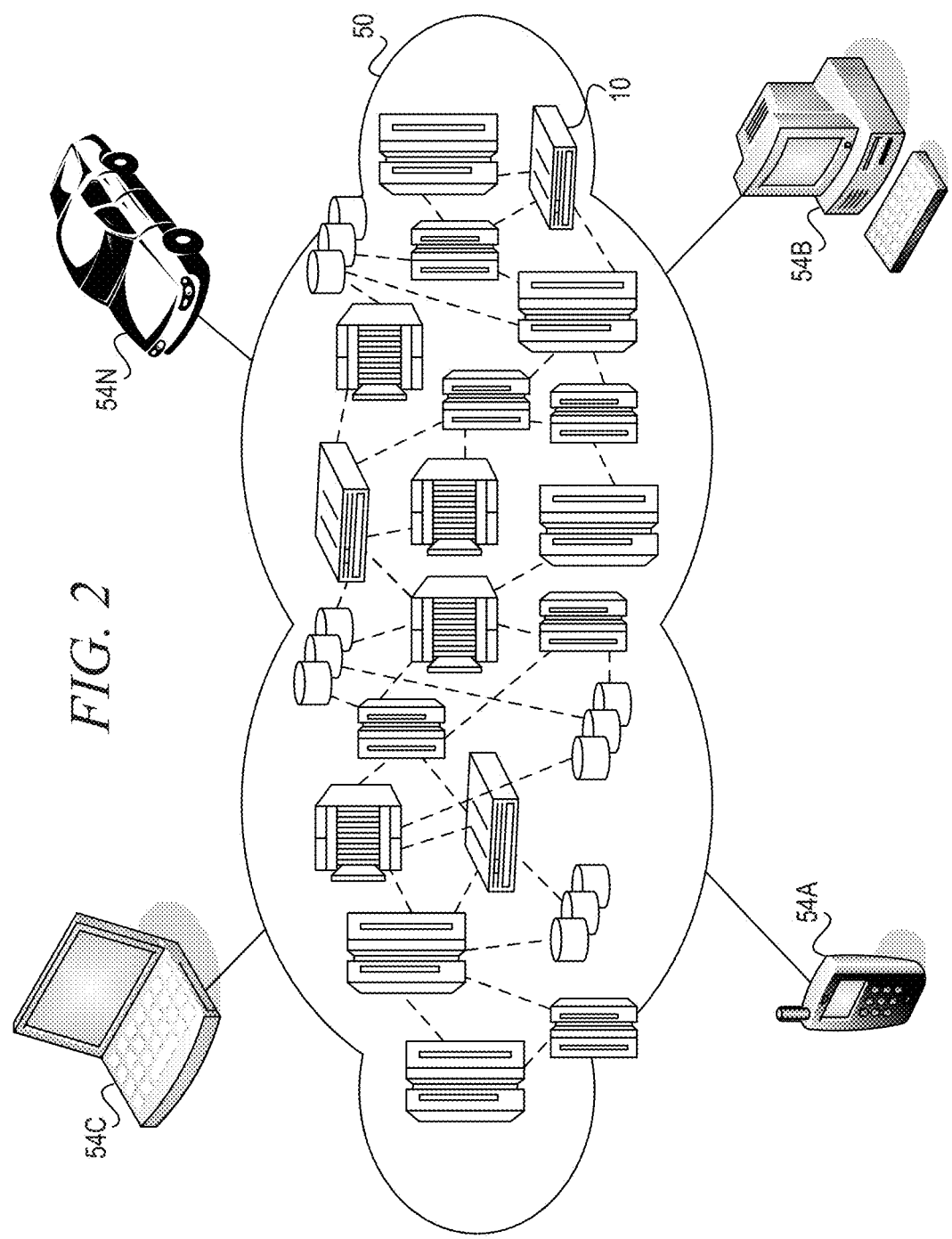
FIG. 2 is another perspective of an illustrative cloud computing environment in which aspects of the illustrative embodiments may be implemented.

Referring now to FIG. 2, another perspective of an illustrative cloud computing environment 250 is depicted. As shown, cloud computing environment 250 comprises one or more cloud computing nodes 210, which may include servers such as server 102 in FIG. 1, with which local computing devices used by cloud consumers, such as, for example, personal digital assistant (PDA) or cellular telephone 254A, desktop computer 254B, laptop computer 254D, and/or automobile computer system 254N may communicate. Nodes 210 may communicate with one another. A computing node 210 may have the same attributes as server 102 and client computer 132, each of which may be computing nodes 210 in a cloud computing environment. They may be grouped (not shown) physically or virtually, in one or more networks, such as Private, Community, Public, or Hybrid clouds as described hereinabove, or a combination thereof. This allows cloud computing environment 250 to offer infrastructure, platforms and/or software as services for which a cloud consumer does not need to maintain resources on a local computing device. It is understood that the types of computing devices 254A-N shown in FIG. 2 are intended to be illustrative only and that computing nodes 210 and cloud computing environment 250 can communicate with any type of computerized device over any type of network and/or network addressable connection (e.g., using a web browser).

Figure 3:
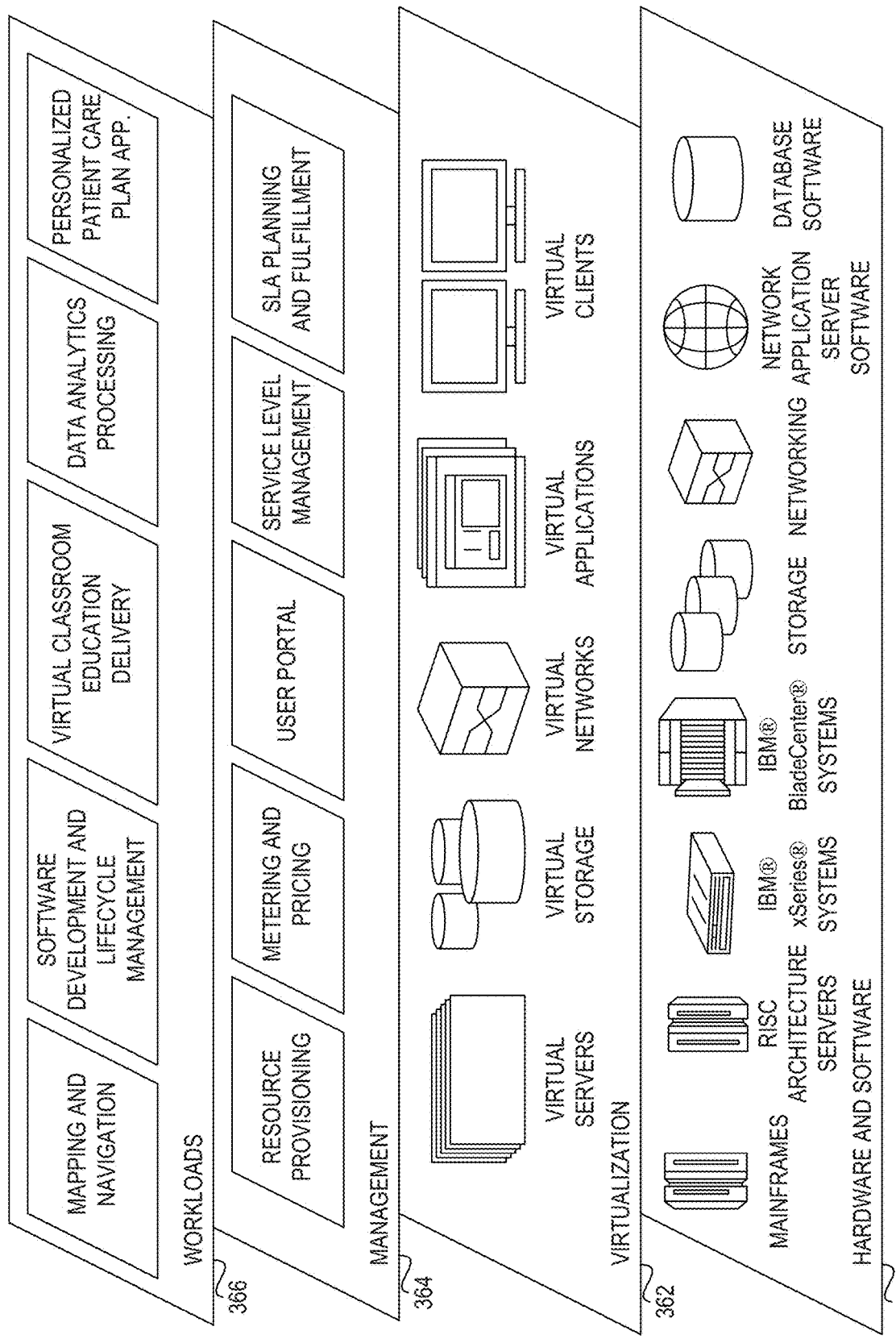
FIG. 3 is an example diagram illustrating a set of functional abstraction layers provided by a cloud computing environment in accordance with one illustrative embodiment.

Referring now to FIG. 3, a set of functional abstraction layers provided by cloud computing environment 250 (FIG. 2) is shown. It should be understood in advance that the components, layers, and functions shown in FIG. 3 are intended to be illustrative only and embodiments of the invention are not limited thereto. As depicted, the following layers and corresponding functions are provided.

The hardware and software layer 360 includes hardware and software components. Examples of hardware components include mainframes, in one example IBM™ zSeries™ systems; RISC (Reduced Instruction Set Computer) architecture based servers, in one example IBM pSeries™ systems; IBM xSeries™ systems; IBM BladeCenter™ systems; storage devices; networks and networking components. Examples of software components include network application server software, in one example IBM Web Sphere™ application server software; and database software, in one example IBM DB2™ database software. (IBM, zSeries, pSeries, xSeries, BladeCenter, WebSphere, and DB2 are trademarks of International Business Machines Corporation registered in many jurisdictions worldwide.).

The virtualization layer 362 provides an abstraction layer from which the following examples of virtual entities may be provided: virtual servers; virtual storage; virtual networks, including virtual private networks; virtual applications and operating systems; and virtual clients. In one example, management layer 364 may provide the functions described below. Resource provisioning provides dynamic procurement of computing resources and other resources that are utilized to perform tasks within the cloud computing environment. Metering and Pricing provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal provides access to the cloud computing environment for consumers and system administrators. Service level management provides cloud computing resource allocation and management such that required service levels are met. Service Level Agreement (SLA) planning and fulfillment provide prearrangement for, and procurement of, cloud computing resources for which a future requirement is anticipated in accordance with an SLA.

Workloads layer 366 provides examples of functionality for which the cloud computing environment may be utilized. Examples of workloads and functions which may be provided from this layer include: mapping and navigation; software development and lifecycle management; virtual classroom education delivery; data analytics processing; transaction processing; and, in accordance with the mechanisms of the illustrative embodiments, a personalized patient care plan creation and monitoring functionality.

Figure 4:
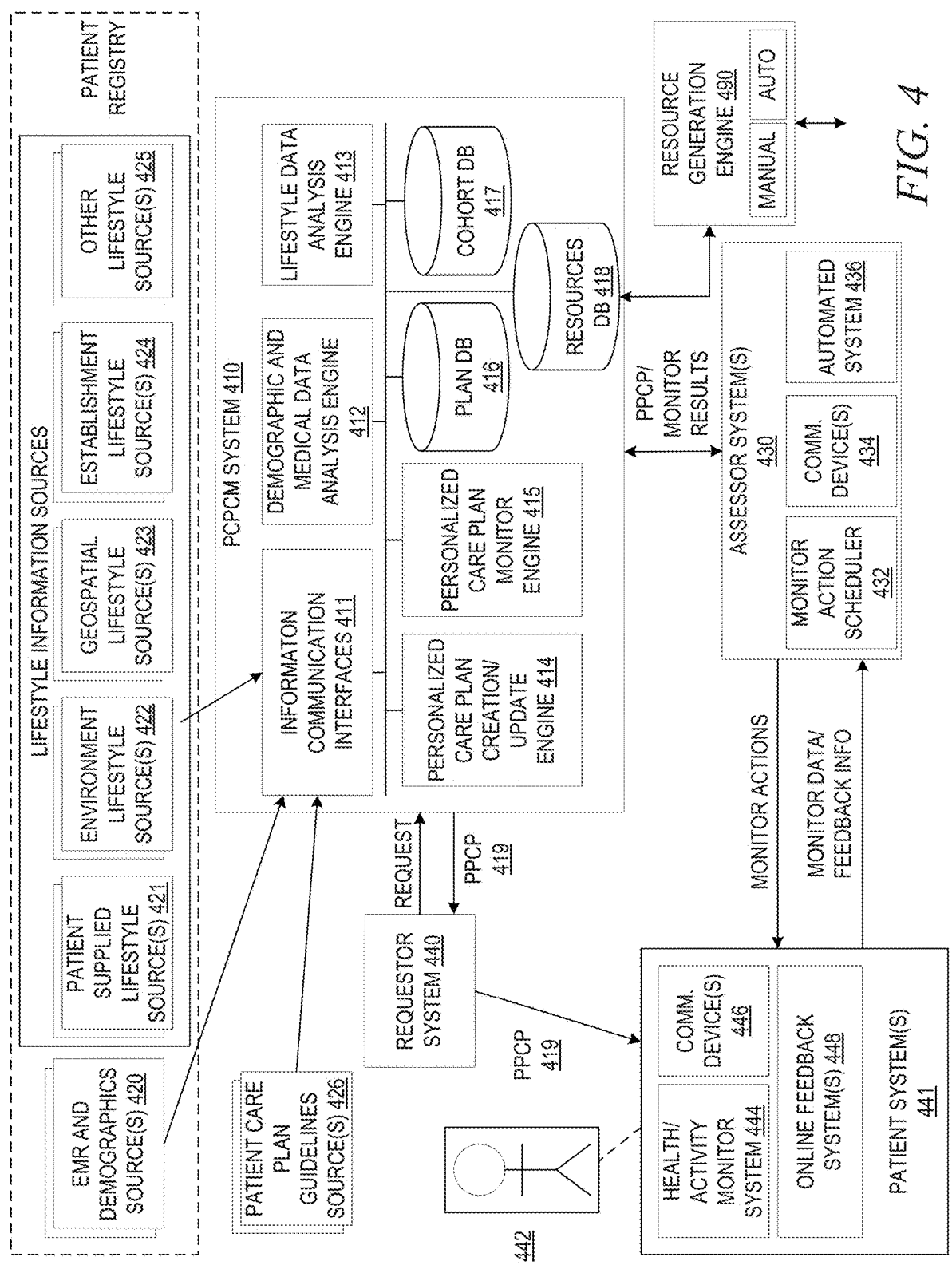
FIG. 4 is an example block diagram illustrating the primary operational elements of such a personalized patient care plan creation and monitoring system in accordance with one illustrative embodiment.

As discussed above, the illustrative embodiments provide a personalized patient care plan creation and monitoring system which may be implemented in various types of data processing systems. FIG. 4 is an example block diagram illustrating the primary operational elements of such a personalized patient care plan creation and monitoring system in accordance with one illustrative embodiment. The operational elements shown in FIG. 4 may be implemented as specialized hardware elements, software executing on hardware elements, or any combination of specialized hardware elements and software executing on hardware elements without departing from the spirit and scope of the present invention.

As shown in FIG. 4, a personalized patient care plan creation and monitoring (PCPCM) system 410 comprises information source interfaces 411, demographic and medical data analysis engine 412, lifestyle data analysis engine 413, personalized care plan creation/update engine 414, and personalized care plan monitor engine 415. In addition, the PCPCM system 410 maintains a personalized patient care plan database 416 that stores data corresponding to the personalized patient care plans generated for various patients and a patient cohort database 417 that stores cohort association information for various patients having similar characteristics, e.g., demographics and/or medical data. Entries in the personalized patient care plan database 416 may be associated with entries in the patient cohort database 417.

A personalization resources storage 418 provides resources utilized by the personalized care plan creation/update engine 414 for identify and correlate demographic, medical, lifestyle information, and general patient care plan information associated with a patient into a series of personalized patient care plan actions and corresponding monitor actions for an assessor. The personalization resources storage 418 may comprise systems of rules, patterns, equations, algorithms, and various other types of logic that codify or otherwise implement functions for selecting and deciding how to personalize a general set of goals and actions in a general patient care plan to a personalized patient care plan. These rules, patterns, equations, algorithms, and the like, may be developed over time by subject matter experts, automatically identified by automated systems, such as natural language processing systems, or the like. For example, such automated and manual based mechanisms may be provided as part of a resource generating engine 419 described in greater detail hereafter.

The rules, patterns, equations, algorithms, etc., may be applied to the large set of demographic, medical, and lifestyle information obtained for the patient to obtain an automatically generated personalized patient care plan which may then be presented to a subject matter expert, such as a doctor, nurse, other medical professional, or the like, for confirmation before prescribing the personalized patient care plan to the patient. It should be appreciated that the resources 418 may further be utilized by the personalized care plan monitor engine 415 when monitoring adherence to a personalized patient care plan and determining modifications to the personalize patient care plan based on determined levels of adherence, as discussed hereafter. Moreover, the resources 418 may be used to determine appropriate actions for interacting with patients, care providers, payment providers, and the like. In some illustrative embodiments, the resources 418 may be used to associate patients in a patient registry, which may comprise EMR and demographics courses 420, lifestyle information sources, and the like, with particular patient cohorts, where a patient cohort is a grouping of patients having the same or similar characteristics.

The information source interfaces 411 provides a data communication interface through which patient data may be obtained from various sources including electronic medical records (EMRs) data source 420, patient supplied lifestyle data source 421, environment lifestyle information source 422, geospatial lifestyle information source 423, establishment lifestyle information source 424, and other various lifestyle information data sources 425. Moreover, the interfaces 411 comprise interfaces for obtaining patient care plan guidelines information from source 426. The EMR data source 420 may comprise various sources of electronic medical records including individual doctor medical practice systems, hospital computing systems, medical lab computing systems, personal patient devices for monitoring health of the patient, dietary information, and/or activity information of the patient, or any other source of medical data that represents a particular patient's current and historical medical condition. The EMR data source 420 may further comprise data representing the patient demographics since such information is typically gathered by providers of such medical data.

The patient supplied lifestyle data source 421 may be a database and/or computing system that gathers and stores information from the patient indicating the patient's response to questionnaires, presented either physically and then entered through a data entry process or presented electronically and gathered automatically, directed to the patient's lifestyle, preferences, and the like. For example, questions in the questionnaire may ask questions about the patient's personal daily schedule, home and work environment conditions, family information, preferences regarding food types, exercise types, times of the day for performing actions, and the like. This information is gathered directly from the patient but may not cover all aspects of the patient's lifestyle. This lifestyle information may be augmented by other lifestyle information gathered from other sources which may be third-party lifestyle information sources. These third-party lifestyle information may comprise information from commercial and governmental computing systems, databases, and the like, that characterize the patient's environment, availability to resources (e.g., products/services/facilities), etc.

In the depicted example, third-party lifestyle information sources comprise environment lifestyle information source 422, geospatial lifestyle information source 423, establishment lifestyle information source 424, and other various lifestyle information data sources 425. Examples of environment lifestyle information source 422 comprise weather information services, air quality information services, traffic information services, crime information services, governmental information services regarding public utilities, or any other environment lifestyle information source 424. As one example, a third-party geospatial lifestyle information source 423 may comprise a global positioning system (GPS) source that identifies the patient's associated locations, e.g., home, work, etc., and identifies establishments around those locations that provide resources that are of interest to the patient's lifestyle and potentially of interest in generating a patient care plan. For example, as mentioned above, specialty grocery stores, vitamin stores, pharmacies, restaurants, gyms, walking paths, parks, recreational areas, community pools, and the like, may be identified based on a GPS system and its associated databases of information.

The information from the geospatial lifestyle information source 423 may be used to request or lookup establishment information in the establishment lifestyle information source 424. For example, if the geospatial lifestyle information source 423 identifies an establishment type and specific identity of a particular establishment, this information may be used to request or lookup other third-party lifestyle information for the establishment in the establishment lifestyle information source 424, e.g., the establishment's website, an industry based website, blogs, commercial establishment information repository, or the like, to retrieve specific information about the identified establishment, e.g., menu items, nutrition information, hours of operation, and the like. Similarly, other third-party lifestyle information source 425 may provide information for correlation with patient care plan actions/tasks including hours of operations, products/services provided, distance from the patient's locations, and the like.

The lifestyle information obtained from the lifestyle information sources 421-425 may be combined with EMR and demographics information for a patient to generate a patient registry record of a patient registry. The patient registry may comprise information for a plurality of patients which may be operated on by the PCPCM system 410 to identify personalized patient care plans for patients, associated patients with patient cohorts, identify potential opportunities for improving care of patients in accordance with clinical rules applied to the patient information in the patient registry records, and the like.

The patient care plan guidelines source 426 provides information regarding the preferred treatments for various medical conditions or maladies in association with patient characteristics. These guidelines are generally associated with demographic and medical information about patients and provide general guidelines as to who qualifies for a treatment, or patient care plan, and who does not based on their medical information and demographic information. The patient care plan guidelines provide an initial basis for determining a general patient care plan for a patient which may then be personalized to the particular patient based on the lifestyle information specific to that particular patient. The patient care plan guidelines from the patient care plan guidelines sources 426 may be provided in a natural language text form which may be processed by natural language processing mechanisms of a resource generation engine 490 to generate clinical rules for determining actions to be performed, communications to be sent, portions of personal care plans to be applied to a patient, or the like. These automated mechanisms may be used in addition to, or in replacement of, manual processes of subject matter experts for generating clinical rules as part of the resources database 418.

The PCPCM system 410 may receive a request to generate a personalized patient care plan for a particular patient, such as from a physician's computing system, a patient computing system, or the like, which initiates the processes of the PCPCM system 410 including retrieving information about the specified patient from the EMR sources 420. The EMR sources 420 provide patient demographic and medical data, gathered from questionnaires, electronic medical records, and the like, to the medical data analysis engine 412 which analyzes the received data and extracts the necessary data for generating patient care plan from the demographic and medical data received. This information is then used as a basis for submitting a request to the patient care plan guidelines source 426 to retrieve patient care plan guidelines for the patient's specific demographics and medical data, e.g., the patient is a 40 year old female diagnosed with type 2 diabetes and thus, corresponding patient care plan guidelines for this combination of patient demographics and medical condition are retrieved from the patient care plan guidelines source 426. Alternatively, the patient care plan guidelines from source 426 may be previously ingested and converted to applicable clinical rules, either through an automated process, manual process, or combination of manual and automated processes. These clinical rules that codify the patient care plan guidelines may be stored in the resources database 418, for example.

The retrieved patient care plan guidelines and/or clinical rules are used along with the demographics and medical data for the patient to generate a baseline patient care plan based on an initial diagnosis of the patient's medical condition, one or more categorizations of the patient based on the collected demographic and medical data, the established patient care plan guidelines, and goals to be achieved by the patient care plan, such as may be specified in the established patient care plan guidelines and/or patient medical data. These operations are performed by the PCPCM system 410 utilizing the resources 418 which provide the clinical rules, logic, equations, algorithms and other logic for evaluating patient information and correlating that information with a patient care plan that comprises patient actions to be performed by the patient and monitoring actions to be performed by the assessor. It should be appreciated that based on the demographic information about the patient and the patient's medical data, only a general patient care plan is generated at this point.

The resulting general patient care plan generated by the personalized care plan creation/update engine 414 is then personalized based on the lifestyle information for the patient obtained via the lifestyle data analysis engine 413 convert the general patient care plan to a personalized patient care plan for the specific patient based on their own unique combination of lifestyle information. The lifestyle data analysis engine 413 obtains the lifestyle information from the various sources 421-425 and performs analysis to generate lifestyle inferences from the lifestyle data. Again, resources may be provided in the resources storage 418 for providing logic, algorithms, clinical rules, patterns, etc., for drawing these inferences from the received lifestyle information. For example, from schedule data for the patient, geospatial lifestyle information, environment lifestyle information, and the like for the patient, it may be determined, based on clinical rules, patterns, algorithms, and the like, that the patient has a sedentary occupation, works in a multi-story building that has a gym, lives in an area with access to parks and walking paths, and the like. As one example, the lifestyle information may indicate that the patient's occupation is a lawyer. From that information, a lookup of the occupation in an occupation database provided in the resources 418 may indicate characteristics of the occupation including characteristics of "stressful", "sedentary", and "long hours" which provides lifestyle inferences about the patient that can be utilized by rules in the resources 418 implemented by the personalized care plan creation/update engine 414 to personalize the general patient actions in the general patient care plan to the particular patient. Various analysis of lifestyle information may be used to extract such inferences from the data which can then be used to personalize a general patient care plan.

As mentioned above, lifestyle information data is obtained from various sources 421-425 to obtain an overall representation of the lifestyle of the patient. These third-party lifestyle information sources 422-425 may provide lifestyle information that is combined with lifestyle information provided by the patient himself/herself 421 for analysis to identify the types of personalized care plan actions to be used with the patient's care plan, the timing of the actions, and the types and timing of patient care plan monitoring and management actions to be performed by an assessor, e.g., a human assessor, automated assessment system, or a combination of human and automated assessment mechanisms. Thus, the selection of patient care plan actions (i.e. patient actions and monitoring actions) is based on the general patient care plan goals, the general patient care plan actions to be performed, and the personalization of these general patient care plan actions to the specific lifestyle of the patient.

Various lifestyle information analysis logic is provided in the lifestyle data analysis engine 413 to evaluate and classify the patient's lifestyle in accordance with a number of defined lifestyle categories. For example, the patient's lifestyle may be categorized according to level of physical activity, level of availability to healthy food sources, quality of home and work environment (lighting, air quality, quietness, safety, etc.), level of access to exercise facilities, various qualitative aspects of the patient's home and work life, and the like. From these categories, a more specific patient care plan is generated to achieve the goals and actions of the generic patient care plan. Non-limiting examples of ways in which general patient care plans may be personalized based on lifestyle information have been provided above. Such personalization may be performed by the personalized care plan creation/update engine 414.

It should be appreciated that the lifestyle information and/or resources 418 may comprise various reference resources from which the mechanisms of the PCPCM system 410 may obtain information for making decisions as to how to personalize the patient care plan actions (patient actions and monitoring actions). Such reference resources may comprise drug information repositories, food nutrition repositories, exercise information repositories, medical procedure repositories, and the like. The "reference" resources differ from other lifestyle information sources in that these "reference" resources tend to be universal for all patients. Such reference resources may be utilized, for example, to assist in determining drug affects on other lifestyle characteristics (e.g., drugs that make one lethargic, prone to disorientation, or the like), selecting foods whose nutritional content falls within the desired goals of a patient care plan, selecting exercises that generate a desired level of activity within a given period of time, and the like.

It should be appreciated that in addition to the evaluation of the patient's demographic, medical, and lifestyle information, the personalized care plan creation/update engine 414 may evaluate the historical personalized care plan information for a patient and for other similar patients to determine appropriate patient actions to include in a personalized care plan. For example, the personalized care plan creation/update engine 414 may look to a history of personalized care plans created for this patient, as may be maintained in the personalized patient care plan database 416 in association with an identifier of the patient, to determine what patient actions the patient was able to successfully complete in previously prescribed personalized patient care plans and use this information to select those same patient actions for a current personalized patient care plan should the current personalized patient care plan have similar goals, general patient actions, and the like that the previously successful patient actions would satisfy. Thus, when selecting personalized patient actions to include in the personalized patient care plan, different weightings may be applied to patient actions based on whether or not they were previously prescribed to this patient, whether or not they were previously successfully completed by the patient in previously prescribed personalized patient care plans, and a level of successful or non-successful completion of the patient action in previously prescribed personalized patient care plans. A highest ranking patient action, amongst the possible patient actions, may then be selected for inclusion in the personalized patient care plan.

In addition, the personalized care plan creation/update engine 414 may retrieve information from the patient cohort database 417 to classify the patient into a patient cohort. The patient cohort is a grouping of patients that have similar characteristics, e.g., similar demographics, similar medical diagnoses, etc. Patient cohorts may be generated using any known or later developed grouping mechanism. One example mechanism may be using a clustering algorithm that clusters patients based on key characteristics of the patient, e.g., age, gender, race, medical diagnosis, etc. As another example, rules in the resources database 418 may be defined for application to patient information in the EMR and demographics sources 420 and lifestyle information sources for identifying patients that have specified characteristics, e.g., patients that have diabetes and are in the age range of 18-45.

With regard to the illustrative embodiments, the present patient may be grouped into a patient cohort and the other members of the patient cohort may be evaluated to identify patient actions that the other members were able to successfully complete as part of their individual personalized patient care plans. These patient actions may then be provided for use in generating the personalized patient care plan for the present patient, with appropriate weightings applied to rank these patient actions relative to other patient actions for purposes of selection as discussed above.

Thus, the PCPCM system 410 provides the various mechanisms for providing actual personalized patient care plans based not only on a categorization of the patient based on their medical diagnosis and demographic information, but also based on their own specific lifestyle information and lifestyle information obtained from third-party sources. In addition, the PCPCM system 410 further provides the mechanisms for generating, as part of the personalized patient care plan, monitoring actions to be performed by an assessor in monitoring the patient's performance of the patient actions of the personalized patient care plan. That is, based on the creation of the series of patient actions to be performed by the patient over a designated period of time, e.g., daily, weekly, monthly, etc., corresponding monitoring actions are identified by the personalized care plan monitor engine 415 using the resources 418. The resources 418 may comprise rules, logic, patterns, algorithms, etc. that match monitoring actions to types of patient actions. Based on timing information for the patient actions, preferences specified by the patient in the patient supplied lifestyle information 421, and the like, these monitoring actions may be scheduled as part of the personalized patient care plan monitor, e.g., every day the patient wakes at 7:00 a.m. and eats breakfast at 7:30 a.m., therefore schedule a monitoring action at 7:25 a.m. to send a text message to the patient's communication device to inform the patient that they should eat bran flakes for breakfast on Monday, Wednesday, and Friday of the week. It should be appreciated that not every patient action needs to have a corresponding monitoring action and that monitoring actions may be schedule for only a subset of the patient actions which are determined to be of most value in assisting the patient with adherence to the personalized patient care plan.

Thus, the resulting personalized patient care plan comprises patient actions to be performed by the patient, and corresponding monitoring actions to be performed by the assessor. Having generated a personalized patient care plan (PPCP) taking into account the patient's personal lifestyle, the PCPCM system 410 outputs the personalized patient care plan 419 to the requestor system 440 for use by the patient 442 in performing the patient actions of the personalized patient care plan. In addition, as noted above, the personalized patient care plan 419 further comprises monitoring actions that are to be performed by an assessor via assessor systems 430, which may be a human being utilizing communications and/or computing equipment 432-436 to perform their monitoring actions, an automated system 436 that automatically performs monitoring actions, or a combination of human and automated systems. The personalized patient care plan 419 is output to the assessor system(s) 430 such that the assessor may utilize the monitoring actions in the personalized patient care plan 419 to monitor and evaluate the patient's performance of the patient actions.

In monitoring the patient 442 and the patient's adherence to the personalized patient care plan 419, the assessor system(s) 430 may obtain feedback information from various patient systems 441 including a health/activity monitor system 444, communication device(s) 446, online feedback system(s) 448, or the like. Examples of health/activity monitor system 444 include wearable devices, such as a FitBit™, iFit™ Fitness Tracker, pedometers, medical equipment with data connectivity to one or more networks via wired or wireless data communication links, or the like. Examples of communication device(s) 446 may include smart phones with applications for communication via data networks to log health and activity data for the patient 442, conventional phones through which a human or automated mechanism places calls to the patient 442, or the like. Examples of online feedback system(s) 448 include websites for tracking a patient's medical condition including online food logs, weight monitoring services, and other health and activity monitoring systems. Any systems that facilitate monitoring and/or communication with an assessor may be used as part of the patient system(s) 441 without departing from the spirit and scope of the illustrative embodiments.

Examples of monitoring actions performed by the assessor system(s) 430 may include interrogating the health/activity monitoring devices and/or applications executing on the communication devices 446 or online feedback system(s) 448 associated with the patient, and initiating a reminder communication to be sent to the patient's communication device 446 via the assessor communication device 434 to remind the patient 442 to perform an action in accordance with their personalized patient care plan 419, scheduling a doctor's appointment for the patient and informing them of the appointment, initiating a call to the patient's communication device 446 to discuss their progress, or any other action that a human or automated assessment system 436 may perform to assist with the monitoring of the patient's adherence to the patients' personalized patient care plan 419. Moreover, results of the monitoring may be returned to the PCPCM system 410 for use in modifying the personalized patient care plan 419 based on the patient's determined level of adherence to the personalized patient care plan 419.

In response to monitoring results and feedback gathered by the assessor system(s) 430, and provided back to the PCPCM system 410, the personalized care plan creation/update engine 414 may dynamically adjust or modify the personalized patient care plan 419 based on a determined level of adherence to the personalized patient care plan 419. That is, the patient's adherence to their personalized patient care plan 419 is monitored via the assessor system(s) 430 and the patient system(s) 441, and determinations are made as to whether the patient meets the goals set forth in the personalized patient care plan 419 and/or performs the patient actions in the personalized patient care plan 419. If the patient does not meet the requirements of one or more goals in the patient care plan 419, an alternative goal determination logic of the personalized care plan creation/update engine 414 is employed to determine an alternative goal that the patient is more likely to be able to accomplish. This determination may be made based on the patient's actual progress towards attaining the original goal, the importance and type of the goal to the overall personalized patient care plan, e.g., adjustments to medication may not be able to be made depending on the particular care plan, and a pre-determined inter-changeability of the goals. These determinations may be made in a similar manner as previously described above with regard to the original generation of the personalized patient care plan utilizing the resources 418 and the like, with the adherence feedback and monitoring data being used as additional lifestyle information for influencing the selection of patient actions and corresponding monitoring actions.

In some cases, one goal may be adjusted in one direction and another in a different direction so as to balance the patient's ability to achieve a missed goal with an alternative goal while maintaining overall results that are to be generated, e.g., physical activity goal may be reduced while dietary goals may be increased so that the balance achieves the same overall effect. In some illustrative embodiments, the determination of alternative patient actions for performing the alternative goals may be based on a historical analysis of patient actions in other patient care plans that the patient and/or similar patients in the patient's cohort have undergone. This historical analysis may identify other similar patient actions that achieved similar results to the patient actions that the patient is found to not be able to achieve in the patient's current personalized patient care plan. Such historical analysis may be performed in a similar manner as previously described above but with a focus on patient actions that were not achieved by the patient 442 in the PPCP 419.

It should be appreciated that the patient systems may further comprise systems for identifying the current location, environmental conditions, changes in a schedule, and the like, for use by the assessor systems 430 in providing feedback to the PCPCM system 410 to adjust the PPCP 419 for the patient's current location and environment. That is, the PPCP 419 may be dynamically adjusted based on the patient's current environmental conditions, changes in schedule, determined deviations from the care plan, and other dynamic conditions that may interfere or otherwise require modification, either temporarily or permanently, of the patient's personalized patient care plan. As noted above, such factors as weather conditions, temperature conditions, resource availability (e.g., gym is closed), and the like may require temporary modifications to a patient's personalized patient care plan. Other factors, such as the patient moving to a new location, obtaining a new place of employment, or the like, may require more permanent modifications to the patient's personalized patient care plan. Such factors may be identified and corresponding modifications initiated taking into account the new temporary/permanent lifestyle changes of the patient.

Figure 5:
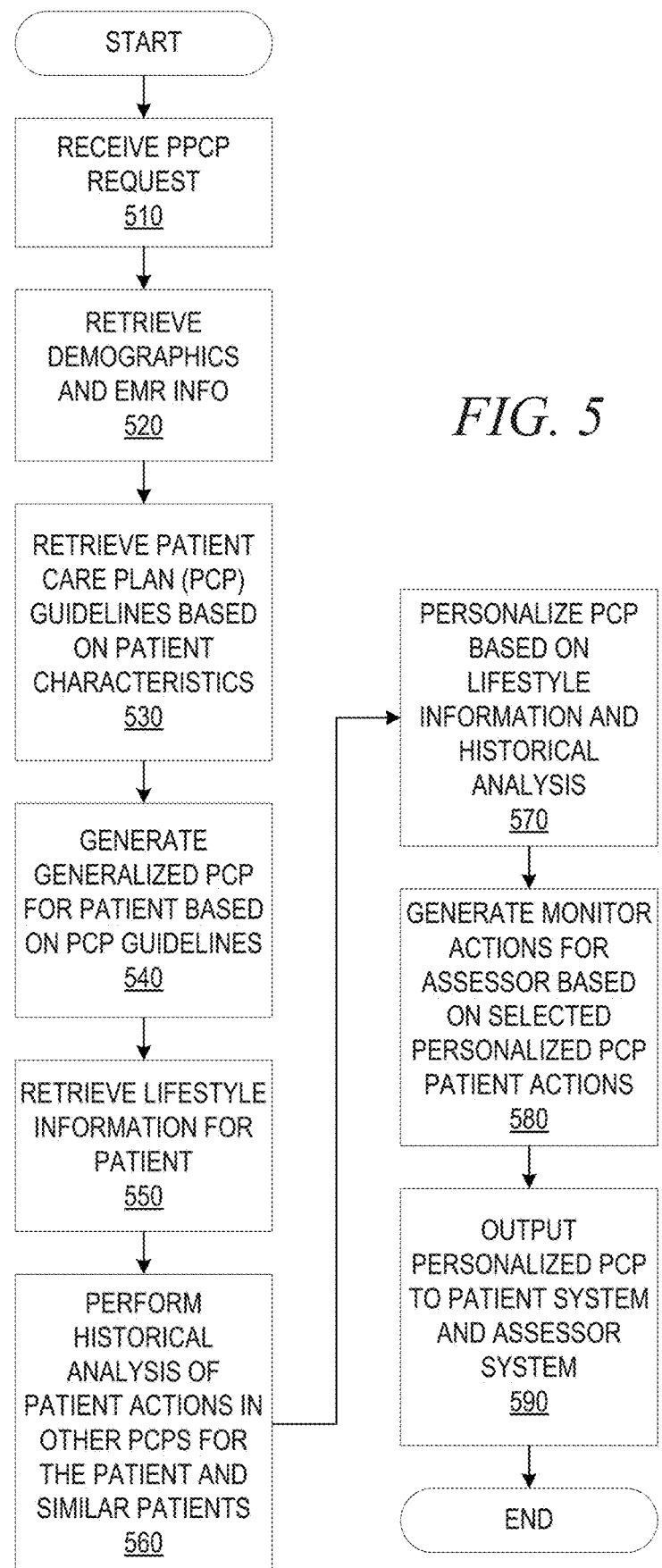
FIG. 5 is a flowchart outlining an example operation for creating a personalized patient care plan in accordance with one illustrative embodiment.

FIG. 5 is a flowchart outlining an example operation for creating a personalized patient care plan in accordance with one illustrative embodiment. As shown in FIG. 5, the operation comprises receiving a request (Personalized Patient Care Plan (PPCP) request) for the creation of a personalized patient care plan specifically identifying a patient for which the personalized patient care plan is to be created (step 510). EMR and demographic information is retrieved for the patient (step 520) and used to retrieve one or more patient care plan guidelines corresponding to the patient's characteristics (step 530). A generalized patient care plan (PCP) is generated for the patient based on the retrieved PCP guidelines and the patient's demographics and medical information (step 540).

Patient specific lifestyle information is retrieved for the patient from a plurality of different lifestyle information sources (step 550). Moreover, in some illustrative embodiments, a historical analysis is performed on patient actions in previously prescribed PCPs for this patient and similar patients (such as patients in a same cohort) to identify patient actions that are ones that the patient is likely to be able to adhere to and weight them more heavily during a selection process (step 560). A personalized PCP is generated based on the generalized PCP as a basis which is then customized and personalized to the specific patient using the retrieved lifestyle information, the historical analysis results identifying patient actions that are likely to be adhered to by this patient, and established rules, patterns, algorithms, logic, etc., for generating personalized patient actions and combining them in a serial manner to generate a sequence of patient actions and goals that together constitute the patient's side of the personalized patient care plan (step 570). Based on the selected patient actions in the personalized patient care plan, corresponding monitor actions for all or a subset of the patient actions are generated using monitoring action rules, patterns, algorithms, logic, or the like (step 580). The monitoring actions are combined with the patient actions in the personalized PCP (PPCP) which is then output to the patient system(s) and assessor system(s) for implementation and monitoring of the PPCP (step 590). The operation then ends.

Figure 6:
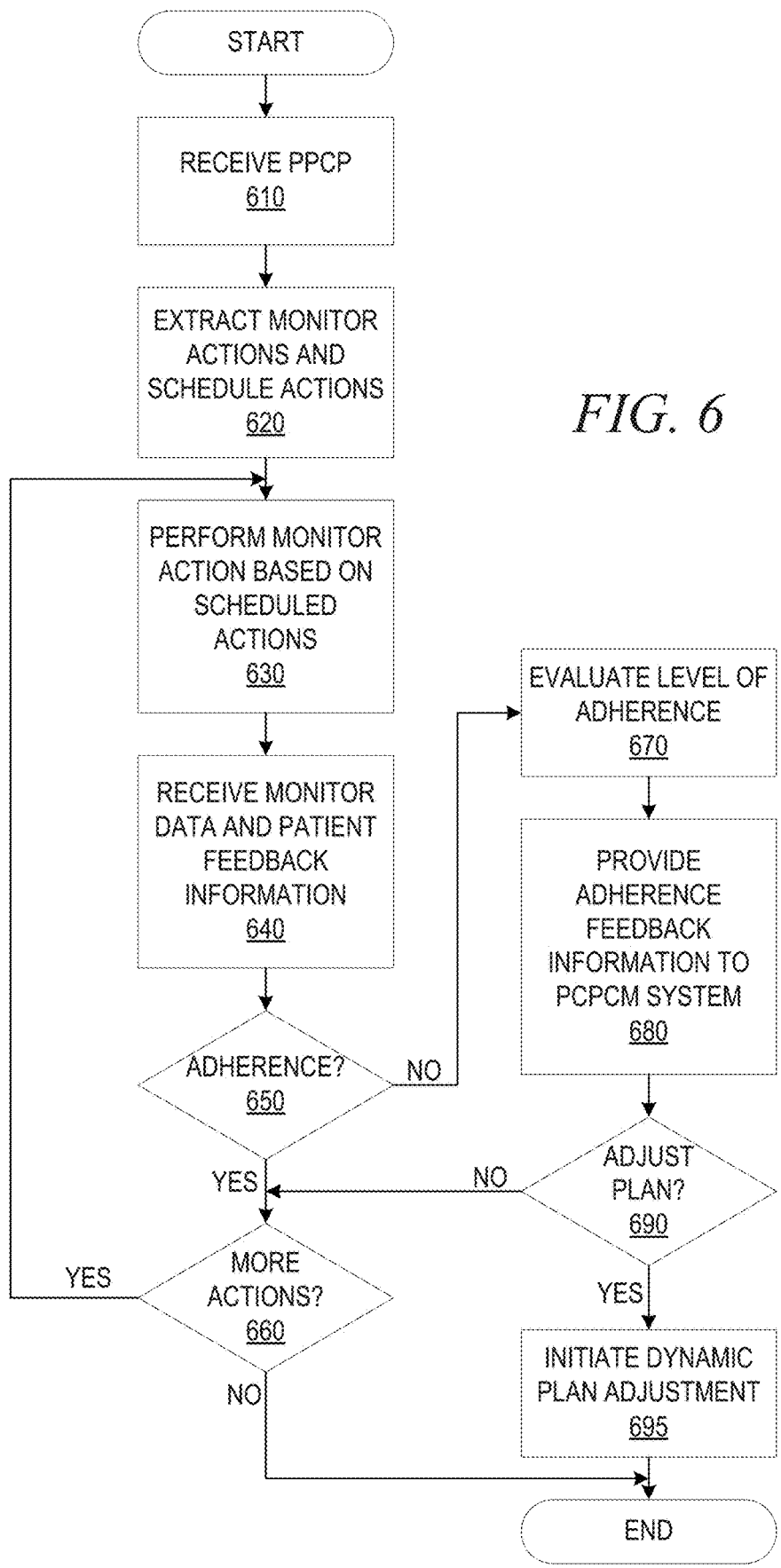
FIG. 6 is a flowchart outlining an example operation for monitoring a patient's performance with regard to a prescribed personalized patient care plan in accordance with one illustrative embodiment.

FIG. 6 is a flowchart outlining an example operation for monitoring a patient's performance with regard to a prescribed personalized patient care plan in accordance with one illustrative embodiment. As shown in FIG. 6, the operation starts by receiving a PPCP (step 610) from which monitor actions are extracted and scheduled by an assessor system (step 620). A next monitor action in the schedule of monitor actions with regard to this patient is performed based on the schedule (step 630). It should be appreciated that the performance of such monitor actions may be automated, may be performed by a human, or may be a semi-automatic process in which different aspects of the monitor action are performed by an automated system and by a human.

In response to the monitor action being performed, monitor data and patient feedback information are received (step 640). For example, this may involve interrogating a health/activity monitoring device associated with the patient and receiving the corresponding data as a result. As another example, this may involve a human assessor calling the patient, asking the patient some questions about the patient's adherence to the PPCP, and then performing data entry to enter the monitor data and patient feedback information into the assessor system. In still another example, this may involve the patient logging onto an online system and inputting monitor data into the system which then reports the information to the assessor system, e.g., a patient entering blood sugar measurement data, weight data, symptom data, or the like. Manny different ways of obtaining monitor data and patient feedback data may be utilized depending on the desired implementation of the illustrative embodiments.

Based on the monitor data and patient feedback information received, a determination is made by the assessor system as to whether the patient is adhering to the patient action required in the PPCP (step 650). If the patient action in the PPCP is being adhered to, then a determination is made as to whether more patient actions in the PPCP to be checked (step 660). If so, the operation returns to step 630. If there are no more patient actions to be checked, then the operation terminates.

If the patient action is not being adhered to, as may be determined from a comparison of the patient's monitor data and feedback to the requirements of the patient action in the PPCP, then an evaluation of the level of adherence is performed (step 670). Adherence feedback information is provided to the PCPCM system (step 680) and a determination is made as to whether the level of adherence is such that it warrants an adjustment of the patient actions in the PPCP (step 690). This determination may take into account various factors including the nature and importance of the patient action to the overall goal of the PPCP, e.g., taking medication may be considered much more important that walking for 30 minutes a day, a number of times this patient action has not been adhered to over a specified period of time, e.g., patient fails to walk for 30 minutes for 3 days in the past 5 days, an amount of the patient action that was actually achieved, e.g., the patient walked for 20 minutes but not 30 minutes, and the like. Based on a determined level of adherence and the nature and importance of the patient action, the assessor system determines whether an adjustment of the PPCP is needed (step 690).

If an adjustment is needed, then the dynamic plan adjustment operations of the PCPCM system 410 are initiated by a request from the assessor system (step 695). If an adjustment is not needed, then the operation continues to step 660 where it is determined whether more patient actions in the PPCP need to be evaluated. If so, the operation returns to step 630, otherwise the operation terminates.

Figure 7:
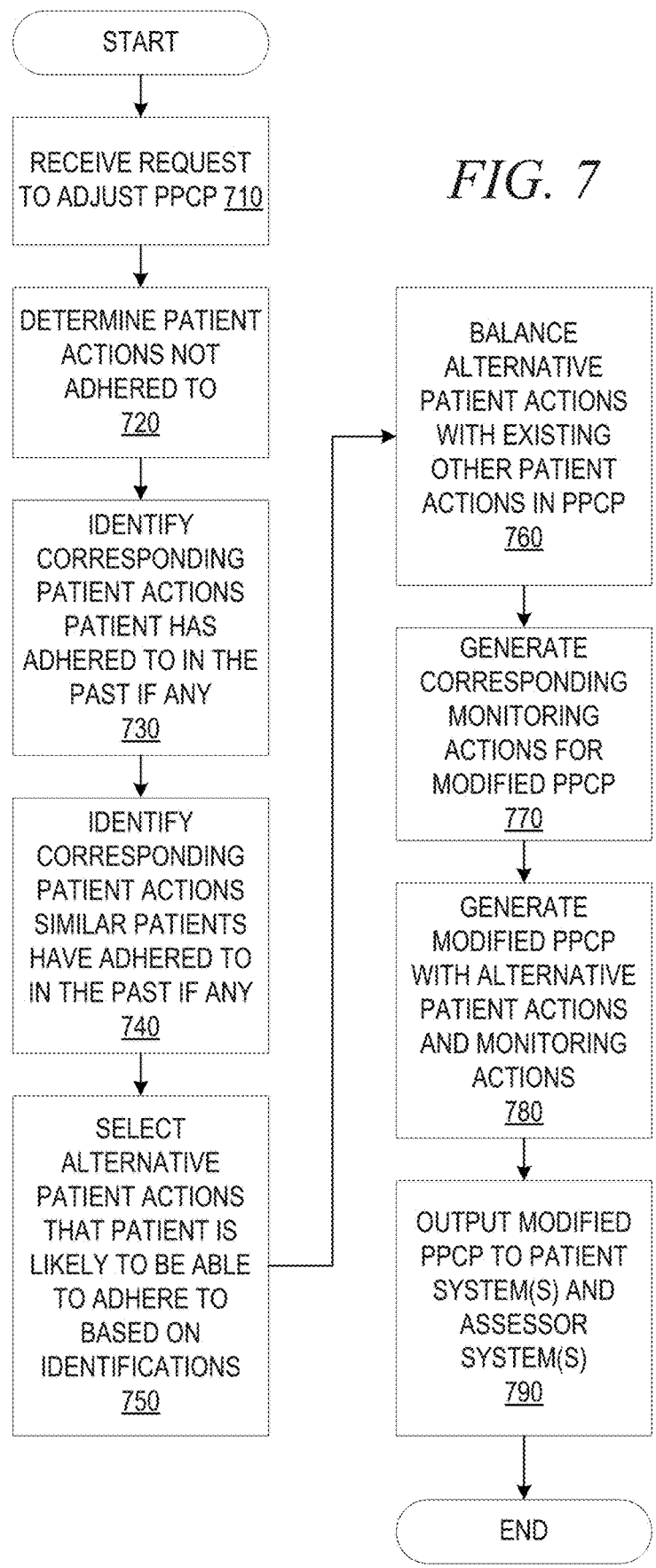
FIG. 7 is a flowchart outlining an example operation for adjusting a personalized patient health care plan based on an evaluation of a patient's adherence to a prescribed personalized patient health care plan in accordance with one illustrative embodiment.

FIG. 7 is a flowchart outlining an example operation for adjusting a personalized patient health care plan based on an evaluation of a patient's adherence to a prescribed personalized patient health care plan in accordance with one illustrative embodiment. As shown in FIG. 7, the operation starts by receiving a request to adjust the PPCP for a patient, such as from the assessor system (step 710). The patient actions not adhered to are determined (step 720) and corresponding patient actions that the patient has adhered to in the past (if any) are identified (step 730). Corresponding patient actions in similar patient PPCPs that the similar patients have adhered to in the past are also identified (step 740).

Alternative patient actions that the patient is likely to be able to adhere to are selected based on the identification in steps 730 and 740 (step 750). The alternative patient actions are balanced with existing patient actions in the PPCP (step 760). This balancing may comprise adjusting other patient actions based on the alternative patient actions so as to achieve the same overall goals of the patient care plan, e.g., adjusting nutrition based patient actions based on changes to exercise or medication based patient actions.

Based on the modified patient actions, corresponding monitoring actions for the modified PPCP are generated (step 770) and a modified PPCP with the alternative patient actions and monitoring actions is generated (step 780). The modified PPCP is output to the patient system(s) and assessor system(s) (step 790) and the operation terminates.

Thus, the illustrative embodiments provide mechanisms for personalizing a patient care plan for a specific patient's own unique set of lifestyle characteristics such that the patient care plan is not generally applicable to a plurality of patients but is specific for the one patient. Information from various lifestyle information sources may be used along with patient care plan guidelines, demographic information, medical information, various resources, and the like, to generate a personalization of a more generic patient care plan that meets the desired goals for addressing a patient's medical condition. The personalization of the patient care plan may take into consideration patient actions that are successfully and unsuccessfully performed by the patient in other patient care plans, and by other similar patients with regard to their own personalized patient care plans. This may be done on a historical basis as well. Furthermore, the mechanisms of the illustrative embodiments provide monitoring actions for monitoring the patient's adherence to the personalized patient care plan and initiation of modifications to the personalized patient care plan when such adherence meets pre-defined criteria indicative of a need for a modification in the patient care plan.

Generation of Clinical Rules for Application to Patient Information

As noted above, the resources database 418 may comprise rules, logic, equations, and the like that are applied by the one or more of the demographic and medical data analysis engine 412, lifestyle data analysis engine 413, and personalized care plan creation/update engine 414 for evaluating patient information from EMR and demographics sources 420 and patient lifestyle information sources 427 to perform various operations. For example, clinical rules may be applied by the demographic and medical data analysis engine 412 and lifestyle data analysis engine 413 to determine cohort membership of the corresponding patient and store such information in the cohort database 417. Based on the classification of the patient into one or more cohorts, corresponding personalized care plan actions, requirements, and the like, may be associated with the patient to generate a personalized care plan and actions to be performed by an assessor. Moreover, application of such rules may be used to perform other actions such as identifying patients that represent care opportunities for providing improved care to patients, communicating with patients, identifying patients of a medical practice that may be candidates for assisting medical personnel in achieving care goals, and the like.

The rules may be generated by resource generation engine 490 using a manual, automatic, or semi-automatic operation and corresponding tools for performing such operations. Although shown in FIG. 4 as separate from the PCPCM system 410, it should be appreciated that the resource generating engine 490 may be integrated in PCPCM system 410 in some illustrative embodiments. In some illustrative embodiments, the resource generation engine 490 may provide user interfaces to users of client computing devices for their use in defining rules, equations, and/or logic for evaluating patient information. In one illustrative embodiment, these user interfaces comprise graphical user interfaces with object oriented representations of rule elements that may be dragged and dropped, user interfaces for selection of rule elements from a pre-determined listing, user interface elements for free-form text entry, and the like.

As noted above, in some illustrative embodiments, automated tools may be used either alone or with manual intervention to generate resources for the resources database 418, such as clinical rules, equations, and/or logic to be applied to patient information. These tools may be created by users utilizing a traditional graphical user interface (GUI), or they may use cognitive computing concepts to assist the user with creating or modifying rules. Cognitive computing techniques used to build rules might include natural language processing or speech-to-text algorithms and systems for taking natural language input, parsing the input, extracting key features from the natural language input, associating these key features with corresponding concepts and values, and generating a structured output that essentially converts the non-structured natural language input to structured information that may be used to generate results/responses. One example of a cognitive based mechanism that may be employed for performing such analysis, extracting features, and generating structured information is the IBM Watson™ cognitive system available from International Business Machines (IBM) Corporation of Armonk, N.Y.

For example, natural language processing may evaluate a patient care plan guideline from source 426 that states "Medication A is safe for adult male patients younger than 65 years of age and having type 2 diabetes without amputation." From this information, structured data may be specified for defining a clinical rule such as the result being administering medication A and the corresponding structured characteristics being male, 18-65, type 2 diabetes, no amputation. These structured characteristics may then be automatically combined into a rule specifying the characteristics required to be present or not present for the corresponding result to be applicable, e.g., the corresponding action to be applicable, corresponding personalized care plan element to be added to the patient's personalized care plan, categorization of the patient in a particular cohort, or any other result that is appropriate for the particular implementation which can be triggered as a result of the conditions/criteria of the rule being satisfied.

The rules themselves may be specified in a structured manner as a set of conditions/criteria specifying characteristics of the patient that must be present (AND requirements), those that may be present (OR requirements), and/or those that must not be present (AND NOT requirements) for the corresponding result to be applicable to the particular patient. The characteristics themselves may take many different forms including demographic information, lifestyle information, medical information, source information, and the like. The characteristics may be specified in terms of date ranges, values, data source identifies, medical codes, combinations of characteristics of the same or different types, or the like.

The rules may be nested or otherwise configured in a hierarchical manner such that if one rule is satisfied by the patient information, this may trigger additional rules to be applied until a final determination as to the action, communication, classification into a cohort, or other result is generated. This configuration sets forth one or more cascading sets of rules such that one rule triggers another rule to be evaluated. For example, a first rule may look to a first subset of patient information to determine if the patient is within a specified age range, is a particular gender, and has been diagnosed with a particular medical malady. If all of these criteria are satisfied, then this may trigger a second rule that looks to lifestyle information of the patient to determine where the patient lives and if the patient lives in a specified geographical area, as well as the patient's amount of physical activity as determined from the patient's occupation and hobbies or interests. This information may be classified and compared to the criteria of the second rule to determine if the criteria of the second rule are satisfied, e.g., lives is north America and has a sedentary lifestyle, which would then trigger the corresponding result, e.g., add exercise to the patient care plan, initiate a communication to promote a gym membership, or the like.

In accordance with some illustrative embodiments, the rules may be categorized into three main types of rules:

demographic rules, medical code rules, and lifestyle information rules. Demographic rules specify one or more conditions or criteria associated with patient demographics, e.g., age, gender, geographical location (e.g., portions of the residence address), occupation, and the like. Medical code rules specify one or more conditions or criteria associated with medical codes that define symptoms, diagnoses, treatments, medical procedures, and the like, associated with the patient. Such medical codes may be specified in the medical history of the patient set forth in the patient registry entries for the patient, a current medical record entry, lab results, and the like. Lifestyle information rules specify one or more conditions or criteria associated with lifestyle patient supplied, environmental, geospatial, establishment, or other lifestyle information as discussed above. It should be appreciated that rules, of the same or different types, may be chained together to generate complex rule ontologies having hierarchical or tree-like structures in which cascading sets of rules are provided. Moreover, some rules may bridge more than one type such that a single rule may look at two or more of demographics, medical codes, and lifestyle information.

In some illustrative embodiments, the rules may be generally thought of as comprising conditions/criteria specified in three different categories, i.e. "AND" criteria, "OR" criteria, and "AND NOT" criteria. The "AND" criteria specify one or more criteria, all of which must be present in order for the rule to be triggered, where triggering a rule means that the criteria of the rule has been satisfied and the result of the rule is applicable to the patient information. The "OR" criteria specify one or more criteria where at least one of the "OR" criteria must be present in order for the rule to be triggered. The "AND NOT" criteria specify one or more criteria where none of the "AND NOT" criteria can be present for the rule to be triggered.

In some illustrative embodiments, an "Any X" qualifier may be applied to the different categories of criteria. What is meant by an "Any X" qualifier is that rather than requiring all of the "AND" criteria to be present, none of the "AND NOT" criteria to be present, and at least one of the "OR" criteria to be present, a number of criteria may be specified as the "X" value and thus, override the default operation of the "AND", "OR," and "AND NOT" criteria. Or, alternatively, the X may specify a number of instances of the corresponding criteria that must be present in the patient information. For example, an X value of 2 may be set for the "AND" criteria meaning that the patient information must include at least 2 of the "AND" criteria or at least two instances of the "AND" criteria (where these 2 instances may be for the same "AND" criteria, e.g., 2 instances of a medical code of type 2 diabetes). Moreover, an "Any X" qualifier may be applied to the "OR" criteria that states that at least X number of the "OR" criteria must be present in the patient information, or at least X instances of at least one of the "OR" criteria must be present in the patient information. If the required number of criteria or instances is not met, then the rule is not triggered.

Moreover, an "Any X" qualifier associated with the "AND NOT" criteria may specify that the patient information must have at least X number of the "AND NOT" criteria to be eliminated from further consideration as triggering the rule. As a default operation, with the "AND NOT" criteria, if a patient's information indicates that the patient has any one of the criteria specified as an "AND NOT" criteria, then the patient is eliminated from further consideration for triggering the rule. However, by applying an "Any X" qualifier, this default operation may be modified to require more than one of the criteria to be present or more than one instances of one or more of the criteria to be present before the patient is disqualified for potentially triggering the rule.

By specifying all three categories of criteria, complex rules are generated that may be applied to patient information to identify specific types of patients for application of the result of the rules. Furthermore, by specifying a rule ontology of a hierarchical or tree-like arrangement, complex evaluations of patient information may be achieved.

Figure 8:
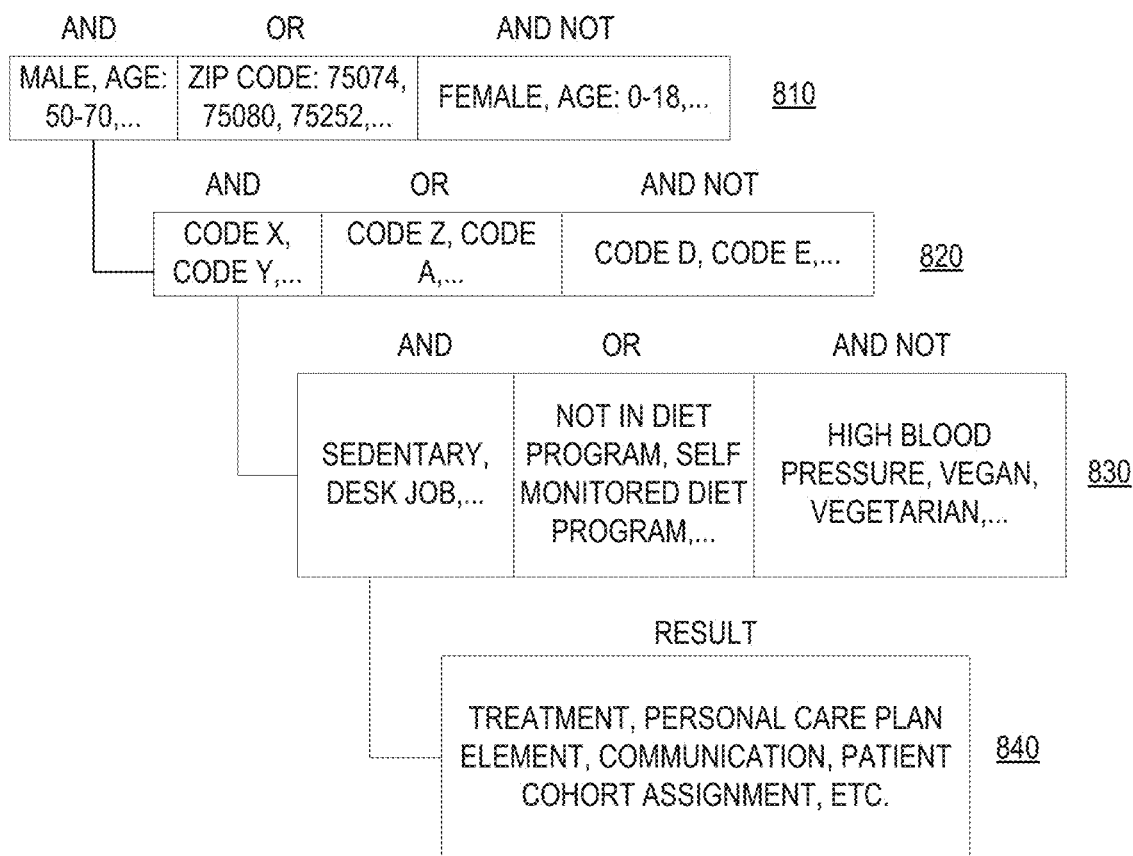
FIG. 8 is an example diagram of an example hierarchical set of rules in accordance with one illustrative embodiment.

FIG. 8 is an example diagram of an example hierarchical set of rules in accordance with one illustrative embodiment. As shown in FIG. 8, a nested hierarchical arrangement is provided comprising rules 810-830. The triggering of a rule 810, for example, causes a subsequent rule 820 to be evaluated to determine if it is triggered, which in turn causes a subsequent rule 830 to be evaluated. Each rule's criteria may be evaluated against patient information in a patient registry and/or obtained from other lifestyle and third party information sources. In the example shown in FIG. 8, the rules utilize the AND, OR, and AND NOT format previously mentioned above with the corresponding example criteria being shown in the corresponding boxes of the rule 810-830.

In the depicted example, rule 810 is an example of a demographics rule that uses criteria directed to the demographics of patient information. Rule 820 is an example of a medical code rule that uses criteria that is directed to the presence or absence of medical codes within the patient information. Rule 830 is an example of a rule that combines both lifestyle information and medical information in a single rule. For example, lifestyle information may indicate that the patient is sedentary, has a desk job, is not in a diet program or is in a self-monitored diet program, is or is not a vegan or vegetarian, and the like. Medical information from the patient's EMRs and the like, may indicate that the patient has or does not have high blood pressure, as well as other medical conditions. It should be appreciated that the criteria specified in the rules may include spatial and or temporal qualifiers as well, although not explicitly shown in FIG. 8. For example, a rule's criteria may specify that the patient has medical code X and also has medical code Y within 1 year of the time the patient was diagnosed with medical code X.

As shown in FIG. 8, the result generated from the triggering of rule 810 is to evaluate rule 820. Similarly, the result generated from triggering rule 820 is to evaluate rule 830. If all of the rules 810-830 are triggered, the final result 840 of rule 830 is performed. This final result 840 may comprise some recommendation for treatment, an addition of a personal care plan element to the patient's personal care plan, initiating a communication with the patient or medical personnel, assignment of the patient to a particular patient cohort, or other suitable operation based on the particular implementation. If any of the rules in the hierarchy do not trigger, then the subsequent evaluations are not performed, i.e. the results of triggering the rule are not followed. It should be appreciated that the resources database 418 may comprise a complex set of rules of these types in various hierarchies or tree-structures for application to patient information.

Figure 9B:
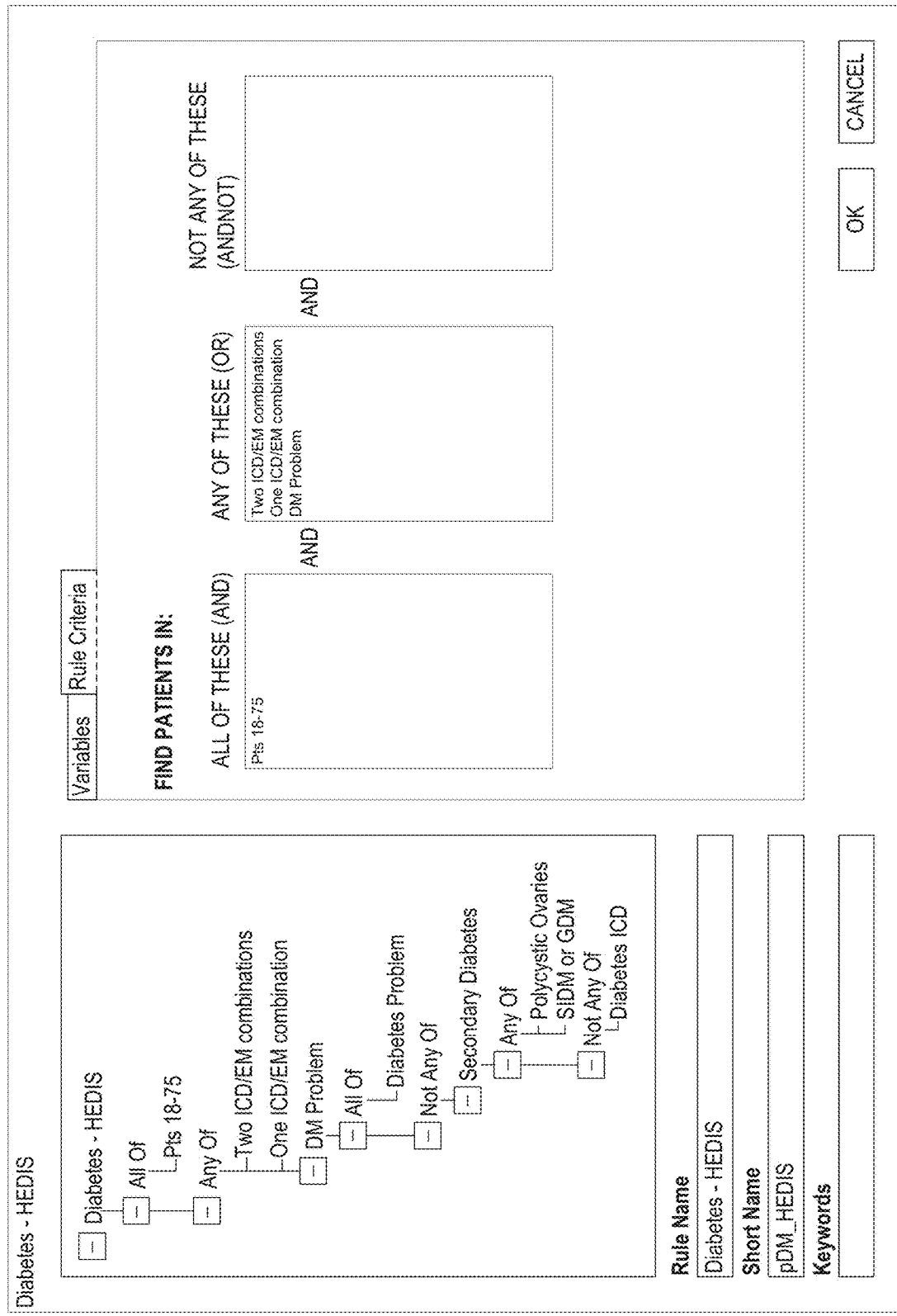

FIGS. 9A-9C are diagrams illustrating example graphical user interfaces for rule generation in accordance with one illustrative embodiment. The graphical user interfaces (GUIs) shown in FIGS. 9A-9C may be presented by the resource generation engine 490 to a user via the user's client computing device and one or more data networks and may be used by the user to define one or more rules for application to patient information, such as patient information in the patient registry.

FIG. 9A illustrates an example GUI for defining various medical codes that are recognizable by the mechanisms of the illustrative embodiments and used in the various rules of the illustrative embodiments. In FIG. 9A, medical codes indicating a diagnosis of diabetes are entered into a list of codes. In this example GUI, these codes are used by rules to identify diabetic patients when a matching code is found within the patient's medical record. Matching codes are then subjected to further selection criteria described within the rules engine, as shown in FIG. 9C described hereafter.

FIG. 9B illustrates an example GUI for defining a rule for identifying patients that are part of a cohort of patients. As shown in FIG. 9B, the GUI comprises a field for specifying a rule name, e.g., "Diabetes—HEDIS", and a field for the short name of the rule which may be used to reference the rule in other rules, where HEDIS refers to the Healthcare Effectiveness Data and Information Set tool. The rule comprises an AND set of criteria, e.g., patients aged 18-75, an OR set of criteria, e.g., Two ICD/EM combinations or one ICD/EM combination and a DM Problem, and a ANDNOT set of criteria (none shown in the depicted example). The rule hierarchy is shown in the top left portion of the GUI. Various rules may be generated using this GUI and hierarchical combinations of rules may be generated through references to the short names of other rules. The hierarchies may be depicted in the top left portion of the GUI during generation. In this GUI example shown in FIG. 9B, the user has selected the rule at the top of the tree. The tree shows the hierarchy of the entire rule, while the lists depicted on the right side of the screen show the details for the top level of the hierarchy. The user can edit the rules and move them around in the hierarchy using the tree or by manipulating items on the detailed view displayed on the right hand side of the screen. Users can use the tree or the detailed view to add/edit/delete rules from the rule hierarchy. Users can also drag/drop or cut/copy/paste individual rules or an entire rule hierarchy from another rule.

FIG. 9C illustrates an example GUI for adding a medical code based rule referenced by the rule shown in FIG. 9B. In this example, the user has selected a code rule in the hierarchy "Two ICD9/EM combinations" that searches for instances of the list of diabetes codes depicted in FIG. 9A. When a user selects the code rule in the tree or double-clicks it in the detailed view, the detailed view changes to show details about the code rule. The detailed view shown in FIG. 9C depicts the criteria for the code based rule. This rule requires a two instances of diabetes codes entered on the same date as an office visit. Applicable office visit codes are identified within the ENC-27 code table (not shown, but similar to FIG. 9A). In this case, the medical code rule GUI comprises a title field for defining the title of the medical code rule, a code table field that specifies the medical code table that comprises the medical code information referenced by the medical code rule, e.g., the medical code table data structure defined using the GUI of FIG. 9A. Various tabs and corresponding fields are provided that permit the definition of the particular medical codes, combinations of medical codes, and requirements associated with these medical codes to satisfy the criteria of the medical code based rule shown in FIG. 9C.

FIG. 9D illustrates an example GUI for assembling rule relationships in accordance with one illustrative embodiment. In this example, multiple rules are defined as a starting point for another rule. In the example shown, only patients that match the criteria specified by both "sDM_A1C_INVERSE" rule AND the "sDM_A1C_VH" rules will be considered. The GUI allows the user to add or remove related rules as needed. Patients that match both of these rules will be matched against criteria for the "sDM_A1C_UNC" rule, which contains additional code rule and other criteria to identify diabetic patients with uncontrolled HBA1C levels.

Figure 9E:
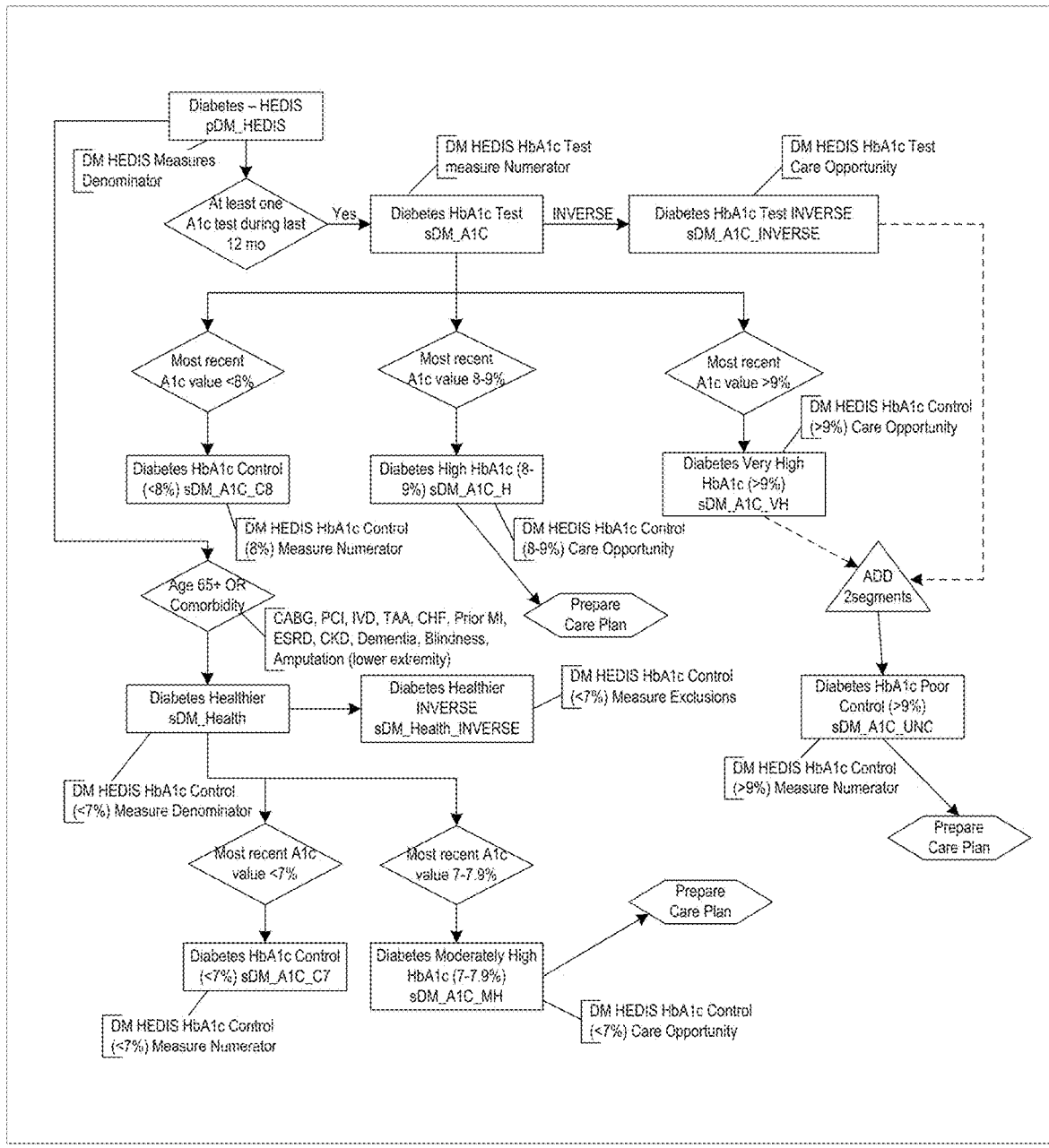
FIG. 9E represents an example rule flow illustrating the application of a rule in accordance with one illustrative embodiment.

FIG. 9E represents an example rule flow illustrating the application of a rule in accordance with one illustrative embodiment. This is the high-level logical flow for the rules depicted by the GUI shown in FIGS. 9A-9D. This diagram also shows how the registry rules are used to flow into a care plan for a patient.

The resulting rules may be stored in the resources database 418 and used by one or more of the analysis engines 412, 413 and personalized care plan monitor engine 415 to generate personalized care plans for patients, initiate communications with patients and/or medical personnel, associate patients with patient cohorts in cohort database 417, which may in turn be associated with particular patient care plans, communications, or other actions, or the like. In some illustrative embodiments, the rules may be used to identify patients that represent care opportunities, where a care opportunity is a patient whose condition or medical care is not sufficient to manage the patient's health or where modifications to the medical care may likely improve the patient's medical condition or management of their medical condition. The identification of care opportunities may be a basis for initiating other operations, such as instigating communication with the patient in accordance with communication workflows, identifying the patient as a candidate for improving medical personnel goal attainment, initiating the application of a medical campaign to the patient, or the like.

It should be appreciated that the rules may be stored in the resources database 418 in various sets or ontologies directed to performing different types of operations. For example, one set of rules may be directed to identifying patient cohorts with which patients may be associated. A second set of rules may be directed to selecting patients for which a communication workflow should be applied to try to have the patient perform a compliance operation, e.g., schedule a doctor's appointment, submit to a particular test or medical procedure, fill a prescription, take medication, or the like.

In some illustrative embodiments, different sets of rules are established for determining whether patients are in compliance with their associated patient care plans or that the medical conditions are believed to be "under control" due to the patient and medical personnel performing the necessary actions to manage the medical condition. For example, the rules will be evaluated to identify the patient as either "in compliance", "non-compliant", or "excluded." Excluded patients are identified by a set of exclusion rules that define conditions that excuse a patient from normal clinical guidelines. For example, rules identifying patients due for a mammogram will include "EXCLUDE" rules in order to excuse those patients whose medical history includes a dual-mastectomy or active breast cancer so that they are considered compliant. Those excluded patients may be addressed under other rules that address different medical guidance specific to their condition.

A rule, or rules, may specify criteria for considering the patient to be in compliance with their treatment. If the rule, or set of rules, triggers, then the patient is considered compliant. If not, the patient is considered non-compliant, unless some other criteria is met to indicate that the patient is "excluded." Thus, based on the application of rules such as those discussed above, it may be determined that treatment A, from a set of treatments A-D, is to be associated with the patient. A separate set of rules may be applied to the patient information after treatment A has been prescribed, to determine if the patient is in compliance with their treatment or not. Those patients that are determined to be non-compliant are considered care opportunities for which additional actions may be triggered. For example, enrolling the patient in a campaign, performing an outreach operation by initiating a communication with the patient, generating or modifying the patient care plan, such as described above, or the like.

Variable Clinical Rules and Caching of Medical Codes for Application to Patient Information In some illustrative embodiments, the clinical rules (or simply "rules" as used herein) generated may be applicable to a variable set of input elements obtained from a variety of different information sources. As noted above, the patient's EMRs, demographic information, lifestyle information, and the like, may be obtained from a variety of sources. EMR information may comprise information from medical service providers about medical services and procedures performed, medical diagnosis information from medical personnel coded in electronic medical records, lab test results, medication information from electronic medical records, pharmacy computing systems, or the like, allergy information from medical records, immunization information, social history information as may be obtained from questionnaires presented by medical personnel (e.g., information about siblings, sexual history, notes about home life, abuse, etc.), reconciliation information from medical records (e.g., records of encounters with the patient after a medical service is provided), medical billing information, insurance claims information, encounter information (e.g., office visits completed), appointment information, medical problem information (e.g., smoker), and the like. The patient information in the EMRs may include patient identifiers, medical codes, event dates, status information, various medical values, birthday information, gender, race, ethnicity, insurance provider information, employment information, and the like, which may be compiled from various sources. Thus, with a large number of potential sources of information, it can be seen that many instances of information in these various sources may map to a similar variable, e.g., many instances of medical codes in various sources may be indicative of a single medical condition or medical problem associated with the patient, e.g., patient is a smoker, patient has high blood pressure, etc.

The variable set represents characteristics of the patient, as specified in patient information of the patient registry obtained from a variety of sources, that correspond to a particular variable input to the clinical rules, but which does not in itself eliminate the patient from further consideration as triggering the clinical rule. That is, just because a patient characteristic is present in the variable set does not mean that the patient necessarily is considered to have a particular variable value associated with it, e.g., just because the patient has a medical code in the variable set indicating that the patient is a previous smoker, does not mean that the patient is an active smoker. The variable set may comprise multiple instances of a characteristic, e.g., multiple instances of a patient's Low Density Lipoprotein (LDL) and/or High Density Lipoprotein (HDL) cholesterol values being recorded in the patient's EMR over time. The variable set may comprise multiple variables from a plurality of sources that all feed into a single variable used by the clinical rules. The variable set, or listing, may be evaluated to determine the confidence of a value for the ultimate variable that the listing is associated with. Alternatively, the listing may be searched for any instance that meets a criteria of a rule such that if at least one instance within the listing satisfies a criteria of the rule, then that part of the rule is satisfied for the evaluation of the patient information.

The variable set or listing (hereafter referred to as a "variable listing") operates to cache patient information specific to a particular input variable for evaluation by the rules. For example, in the case of a medical code rule, the variable listing may cache or store a list of each instance of different medical codes found in various sources that are associated with the variable with which the variable listing is associated. As one example, a variable listing may be associated with a variable of "smoker" which indicates whether the patient is a smoker or not. These medical codes may be of various types depending upon the source from which they are obtained. For example, a first medical code from a first source may indicate a previous smoker, a second medical code from a second source may also indicate a previous smoker, a third medical code from a third source may indicate that the patient does not smoke cigars, a fourth medical code from a fourth source may indicate that the patient has purchased or used a smoking habit suppression product, such as a gum or patch. The combination of these medical codes provide information from various sources that together give a picture or evidence as to the proper value for the variable associated with the variable listing, e.g., whether the patient is likely a smoker or not.

Variable list analysis logic may analyze the variable list to determine what the appropriate value is for the variable associated with the variable list. The various medical codes, patient information, and the like, are processed using cognitive processes to determine an appropriate value for the variable. For example, if the a variable list is associated with the variable "smoker" and there are 20 instances of medical codes or patient information entries present in the variable list, a simple majority evaluation may be used to indicate whether the majority of instances are indicative of the patient being a smoker. Of course, weighted evaluations may be utilized as well, where instances from certain sources, types of sources (EMRs, lifestyle information sources, etc.), certain medical codes, and the like, are weighted more or less heavily. From the analysis, the variable list entries may be collected to evaluate the ultimate variable.

Alternatively, or in addition, the variable list may be maintained as a cache of patient information associated with a variable. In this way, when a rule needs to evaluate a patient's information with regard to a particular variable, the analysis can be performed with regard to the cached information in the variable listing rather than having to access the patient information in the patient registry and extract the information from the patient registry, which may be time consuming. For example, a rule may specify as an "AND NOT" criteria, that the patient is not a smoker, or does not smoke cigars, or is not a previous smoker. As a result, the rule may be applied to cached patient information in the variable list associated with the variable "smoker" and the cached patient information may be analyzed to identify whether any of the cached patient information meets the criteria set forth in the rule or an aggregation of the cached patient information, or a subset of the patient information, meets the criteria set forth in the rule. If so, then the patient may be eliminated from further consideration. If not, then the patient may be considered as potentially triggering the rule as long as the other criteria of the rule is met.

In such an embodiment, the variable listing cache of patient information is progressively and dynamically updated as new patient information is received from the various sources. The variable listing cache of patient information may be maintained as subsequent rules are applied against the patient information. When a rule is to be evaluated, a determination is first made as to whether a variable listing exists for a variable that is referenced by the rule. If so, then this variable listing is analyzed and the criteria of the rule referencing the variable are evaluated against the variable listing. If a variable listing does not exist for the variable, then the standard mechanisms described above for accessing patient information from the patient registry is utilized.

In some illustrative embodiments, the variable listing stores instances of patient information that may represent the same type of indication, but as separate instances. For example, if the patient has multiple LDL cholesterol test results provided in their patient information of the patient registry, and cached in a LDL cholesterol variable listing. In this example, each test result value may indicate a value greater than 180, which is indicative of a high LDL level. A rule may state that there must be at least 2 instances of high LDL and by looking to the LDL cholesterol variable listing and evaluating the values stored in the variable listing against a high LDL level criterion, the rule may indicate that the patient information satisfies this portion of the rule.

Figure 10:
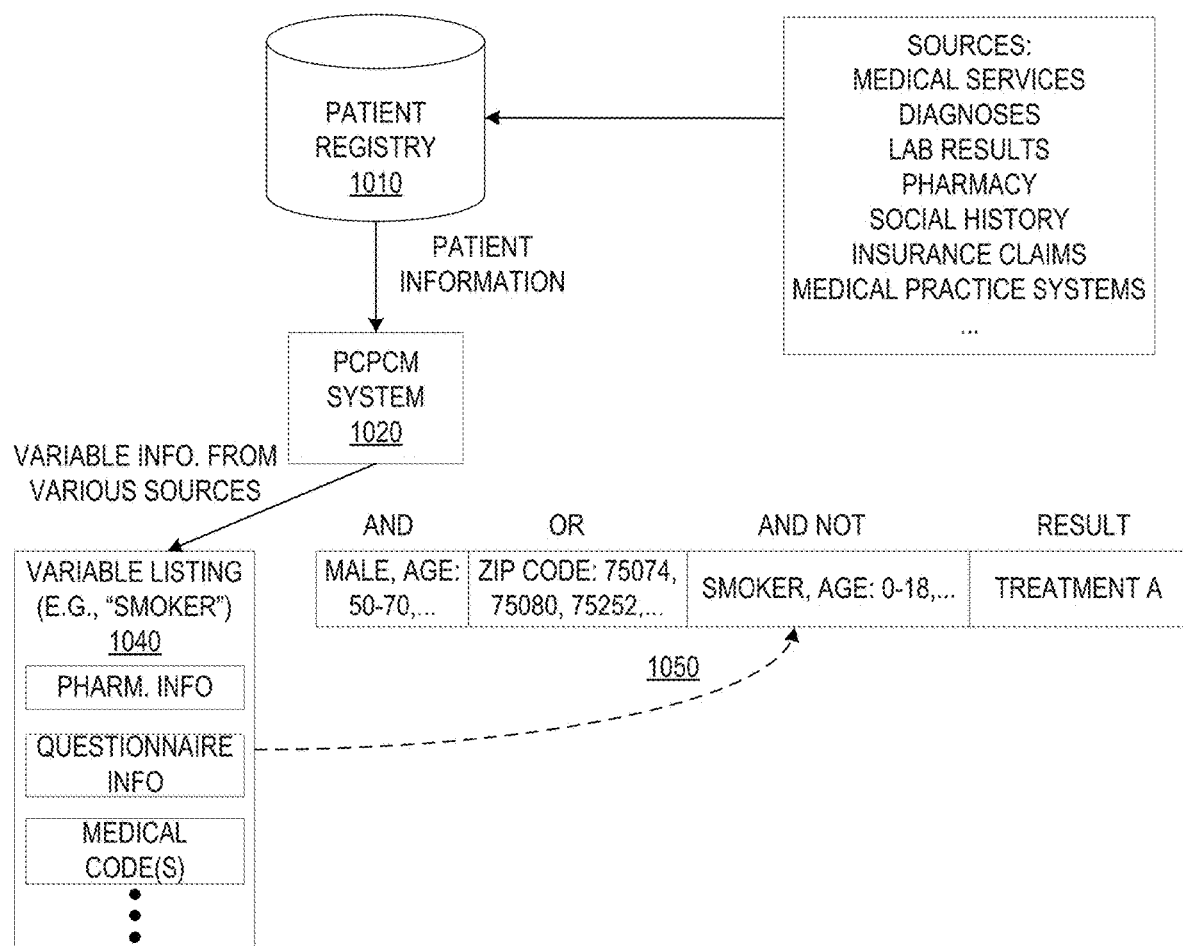
FIG. 10 is an example diagram illustrating a use of a variable listing input to a clinical rule in accordance with one illustrative embodiment.

FIG. 10 is an example diagram illustrating a use of a variable listing input to a clinical rule in accordance with one illustrative embodiment. As shown in FIG. 10, patient information from a patient register 1010 is input to the PCPCM system 1020, such as PCPCM system 410 in FIG. 4, which analyzes the patient information, such as by way of analysis engines 412 and 413, for example. The analysis extracts patient information of interest which may be correlated with one or more variables 1030 and cached in corresponding variable listing data structures 1040 associated with the variables. These variable listing data structures 1040 may be stored in a resources database, such as resources database 418, for example, and indexed by the variable 1030 name, e.g., "smoker", or other variable 1030 identifier for subsequent lookup and retrieval.

When evaluating a patient's information from a patient registry by applying rules from the resources database, the corresponding variable listing data structures 1040 for the patient may be retrieved from the resources database and maintained in a memory or other quick access memory, such as a cache memory, for quick access. Variable listing data structures 1040 to which a rule 1050 applies are retrieved based on the variables referenced in the criteria of the rule 1050. The entries in the variable listing data structures 1040 may be analyzed to determine if corresponding criteria associated of the rule 1050 are satisfied by one or more of the entries in the corresponding variable listing data structures 1040 or a value of the variable 1030 generated based on analysis of the entries in the corresponding variable listing data structure 1040.

Thus, in addition to the rule structures previously described above, mechanisms are provided for caching patient information for variables such that a single variable may have multiple instances of patient information relevant to the variable cached in a variable listing for quick retrieval and applicability of rules. These variable listing data structures may be maintained in a cache for quick access by large sets of rules. In this way, the application of the rules to the patient information is made more efficient by increasing the speed by which the application of the rules is performed.
Clinical Condition Based Cohort Identification and Evaluation As mentioned above, the rules and resources of resources database 418 in the PCPCM system 410 may be used to identify cohorts of patients as well as initiate various operations such as creating personal care plans, elements of personal care plans, initiate communications, and the like. In one illustrative embodiment, the PCPCM system 410 may be extended to incorporate, or work in conjunction with, a clinical condition based cohort identification and evaluation system, hereafter simply referred to as a "cohort system." The cohort system operates to identify different types of cohorts of patients, based on the application of cohort rules in the resources database 418, as discussed above. The cohort system identifies groupings, or cohorts, of patients based on common combinations of patient information, such as patient registry information obtained from the various sources 420-425 described previously. For example, a patient may be analyzed by the cohort system, by applying cohort rules that identify patients that are to be considered members of a specified cohort, and determining if the patient triggers the rules and thus, is a member of the specified cohort.

For example, one or more cohort rules may be established for identifying patients as patients that are type 2 diabetes patients. Thus, all patients in the patient registry that have medical codes or other patient information indicating that the patient is a type 2 diabetes patient will be classified in a type 2 diabetes patient cohort. Identifiers of the patients that are members of a cohort may be stored in a cohort data structure in the cohort database 417. It should be appreciated that the granularity of the cohort may be various levels and a patient may be a member of more than one cohort. For example, a first cohort may comprise type 2 diabetes patients. A second cohort may comprise type 2 diabetes patients that also have a foot amputation. A third cohort may comprise type 2 diabetes patients that also have a foot amputation, are female, and live in the southern Florida geographical area.

In some illustrative embodiments, cohorts are analyzed to identify "meaningful" combinations of patient registry information. A meaningful combination of patient registry information may comprise, for example, patient registry information that is common to patients associated with a positive outcome. That is, the cohort system, in addition to identifying a patient cohort, may comprise analysis mechanisms that analyze the patient information to identify successful outcomes, e.g., patients that kept their doctor appointments, patients that reported reduction in symptoms, or the like, for patients of a particular type or having a particular medical malady, e.g., type 2 diabetes patients, and determining combinations of patient profile information that are common amongst these patients. The definition of a successful outcome is implementation specific and may be defined by a subject matter expert and provided as a configuration parameter for the analysis mechanisms. In general, a successful outcome is a behavior, action, or activity that medical personnel and organizations want patients to engage in so as to maximize the health of the patient or manage a condition of the patient, or an improvement in a medical condition of the patient. Such successful outcomes in most cases bring the patient into compliance with the patient's prescribed personalized patient care plan or other guidelines for treatment of the patient.

A cohort, or "sub-cohort", of patients within the specified cohort is generated centered about common characteristics, common interactions, and the like, of the patients determined to have successful outcomes. The successful outcome cohort, or successful outcome sub-cohort, is generated so as to indicate the patient profile information that is most likely going to result in the corresponding successful outcome. The common characteristics, interactions, etc., of the patient information may specify not only commonalities of the patients themselves, but also commonalities of interactions performed by assessors, automated mechanisms, and the like, to influence the patient so as to achieve the successful output, e.g., communications sent to the patient, personal interactions with medical personnel or medical condition assessors, assignment of personal care plans, or portions of personal care plans, to the patient, medications prescribed, therapies or treatments applied to the patient, or the like. Thus, for example, it may be determined that within a type 2 diabetes cohort, a sub-cohort that has successfully kept their annual foot exam appointments with their doctor are female patients aged 40-50 and that received an email and a follow-up call from a medical assessor to remind the patient to have their annual foot exam.

From the identification of the successful outcome cohorts or sub-cohorts, actions to perform, communications to send, personalized care plan or elements of personalized care plans that may be assigned to a patient, or the like may be identified for application to other patients that are members of the super-cohort or other cohort with which the successful outcome cohort or sub-cohort is associated. For example, if it is determined that female patients aged 40-50 that received an email and a follow-up call from a medical assessor kept their foot exam appointments or made foot exam appointments, then this same email and follow-up call communication protocol may be applied to other female patients in the super-cohort of type 2 diabetes female patients aged 40-50 that may live in other areas other than southern Florida, or other type 2 diabetes patients in general.

Figure 11:
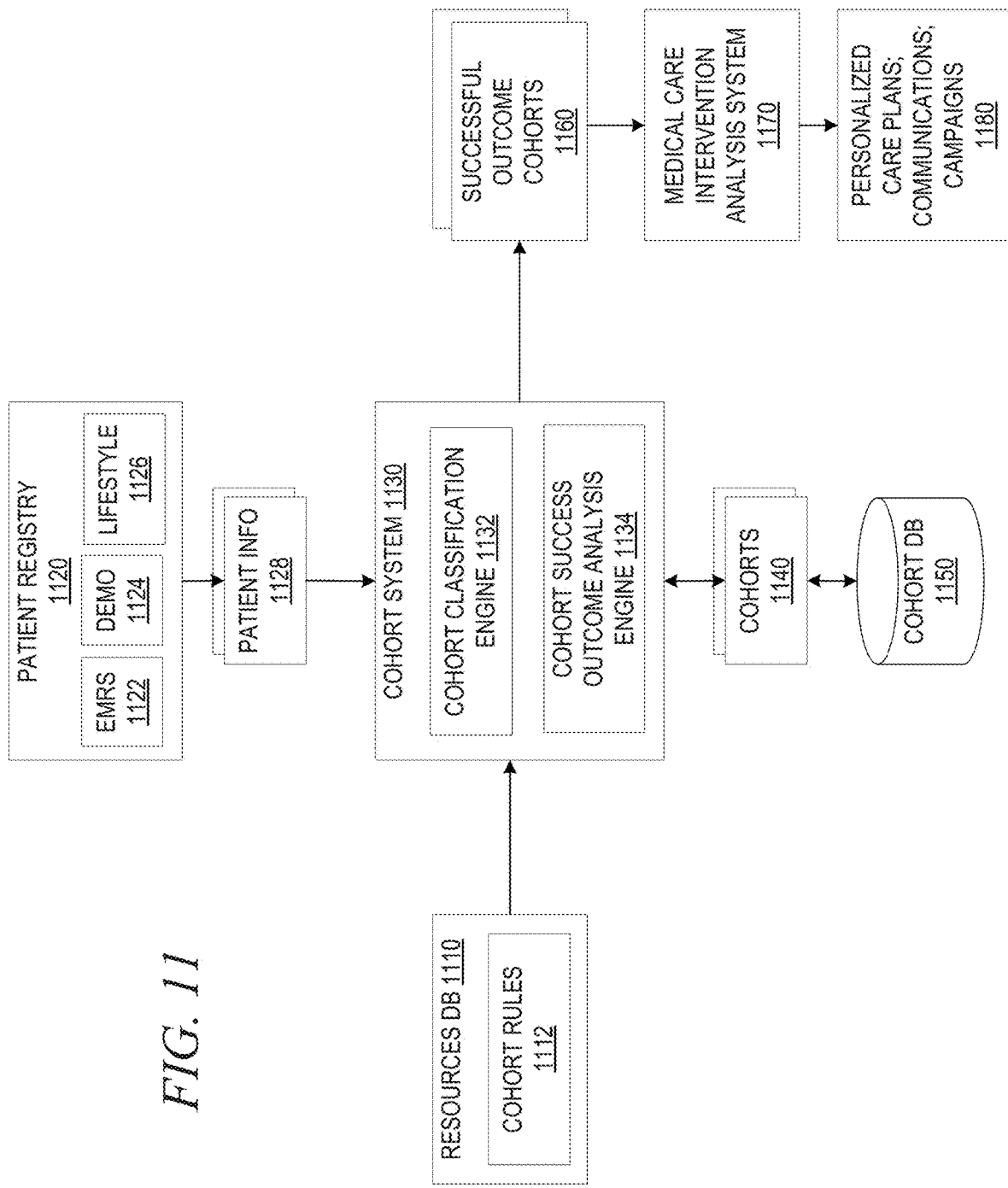
FIG. 11 is an example block diagram of primary operational elements for identifying successful outcome cohorts in accordance with one illustrative embodiment.

FIG. 11 is an example block diagram of primary operational elements for identifying successful outcome cohorts in accordance with one illustrative embodiment. As shown in FIG. 11, the primary operational elements include a resources database 1110 comprising, among other resources, one or more sets of cohort rules 1112 for use in defining various cohorts of patients of interest based on the patient information obtained from a patient registry 1120 comprising electronic medical records 1122, demographic information 1124, and lifestyle information 1126 for a plurality of patients. The resources database 1110 may be similar to resources database 418 in FIG. 4, for example. Moreover, the patient registry 1120 may comprise patient information obtained from the various patient information sources 420-425 in FIG. 4.

A cohort system 1130 is provided that includes patient cohort classification engine 1132 and successful outcome cohort analysis engine 1134, among other logic not explicitly shown. Any operations described as being performed by the cohort system 1130 that are not directly attributed to either the patient cohort classification engine 1132 or successful outcome cohort analysis engine 1134 may be performed by other logic provided in the cohort system 1130. The patient cohort classification engine 1132 applies cohort rules 1112 to patient information 1128 obtained from the patient register 1120 to identify one or more cohorts 1140 and the particular patients whose patient information 1128 indicates that the patient is a member of the one or more cohorts 1140. The identified cohorts 1140 and their membership identifiers, i.e. identifiers of patients (e.g., patient IDs) that are members of the respective cohorts, are stored in cohort data structures in the cohort database 1150. The cohort database 1150 may be similar to cohort database 417 in FIG. 4, for example.

The successful outcome cohort engine 1134 analyzes patient information for patients that are members of cohorts 1140 to identify successful outcome cohorts 1160, i.e. cohorts or sub-cohorts of patients that have had successful outcomes as defined by configuration information defining successful outcomes as provided to the successful outcome cohort engine 1134. Configuration information used to configure the successful outcome cohort engine 1134 may identify successful outcomes for various types of patient cohorts 1140. Thus, for example, for a cohort associated with type 2 diabetes patients, a successful outcome may be defined as the patient completing their annual foot exam. For another cohort, associated with bladder cancer patients, a successful outcome may be defined as scheduling their 6 month follow-up physician appointments. Various types of successful outcomes may be pre-defined and used to configure the successful outcome cohort engine 1134. The configuration information may be used to analyze the patient information for specified corresponding cohorts 1140 retrieved from the cohort database 1150 to determine which patients in each of the cohorts are determined to have had successful outcomes and define a successful outcome cohort, or sub-cohort.

Thus, for example, the successful outcome cohort engine 1134 may retrieve a cohort 1140 for type 2 diabetes patients. The successful outcome cohort engine 1134 may then analyze the patient information 1128 retrieved from patient registry 1120 for each of the patients that are members of the type 2 diabetes patients cohort 1140. For those that have patient information that indicates a successful outcome of completing their annual foot exam, these patients are associated with another cohort referred to as a successful outcome cohort 1160. In a sense, this successful outcome cohort 1160 is a sub-cohort that is comprised of a subset of the members of the type 2 diabetes cohort 1140.

The successful outcome cohort(s) 1160 may be provided to a medical care intervention analysis system 1170. The medical care intervention analysis system 1170, while shown as a separate system from cohort system 1130, may be integrated with cohort system 1130 in some illustrative embodiments. Moreover, the medical care intervention analysis system 1170 may be part of an extension of the PCPCM system 410 in FIG. 4 in some illustrative embodiments. The medical care intervention analysis system 1170 analyzes the patient information for the patients that are part of the same successful outcome cohort 1160 to identify commonalities amongst the characteristics in the patient information. For example, commonalities may include demographic information, actions performed, communications sent to the patients, temporal characteristics of communications/actions performed, and the like. A measure of prevalence of the commonalities is calculated for each of the commonalities identified and the prevalence measures may be compared to one or more threshold values to select commonalities that should be used as a basis for recommending interventions for other patients having similar characteristics.

For example, the medical care intervention analysis system 1170 may analyze patient information for patients of a successful outcome cohort 1160 associated with type 2 diabetes patients. It may be determined that 35% of these patients were contacted by electronic mail, using a specified script or content form X, and then a follow-up automated phone call was made 3 days later using a specified script Y. It may also be determined that 10% of these patients were contacted only by the automated phone call, but using a script Z. Another 25% may have received only the electronic mail message using script or content form X. Still a further 25% scheduled their foot exam at their previous doctor's visit and no follow-up was required. Another 5% may not be able to be identified as having any discernible commonality of communications sent to them. Moreover, other commonalities, such as geographical region, gender, age, etc., may be evaluated and used to identify classifications of patients.

Assuming a threshold value of 30%, in this example, the only communication option that meets the threshold criteria as indicative of an influential intervention with the patient that assisted in helping the patient to achieve a successful outcome is the communication protocol comprising the electronic mail message with script X followed-up by an automated phone call 3 days later using the specified script Y. This information may be associated with the cohort 1140 that is the original basis for the creation of the successful outcome cohort 1160 and/or the successful outcome cohort 1160 itself. This information may further be provided to one or more intervention systems 180, such as the PCPCM system 410 in FIG. 4, a communications system, a campaign system, such as an advertising campaign, or the like, to initiate or at least recommend the corresponding intervention actions deemed to be common to the successful outcome cohort 1160 members at the predetermined threshold value level or higher.

Using this information, the PCPCM system 410 or other logic may analyze patient information from the patient registry 1120 to identify patients that are not in compliance with their associated personalized patient care plans. For example, the personalized care plan monitor engine 415 may analyze the patient information to identify whether a patient is in compliance or not. If the patient is not in compliance, then the patient is considered to represent a care opportunity, or "care op." Such care op patients may be classified into one or more cohorts 1140 and the corresponding successful cohort intervention actions may be recommended for assisting the patient in coming into compliance with their personalized care plan. The patient identifier for the patient that is not in compliance as well as information about the recommended intervention operation to be executed to bring the patient into compliance, may be sent to the one or more intervention systems 180 to cause corresponding intervention operations, e.g., phone calls, electronic mail messages, text messages, modifications to personalized care plans, initiating of a campaign, or the like, to be performed.

It should be appreciated that the identification of the intervention operation to be performed may be based on the nature of the non-compliance of the patient. For example, if the patient has failed to schedule an appointment with the doctor, then a first intervention operation associated with patients who successfully scheduled an appointment with their doctor, and have similar characteristics to the patient that is determined to be non-compliant, may be selected for use. If the patient has failed to obtain a test from a lab, then a second intervention operation associated with patients that successfully had the test performed at the lab, and have similar characteristics to the non-compliant patient, may be selected for use. Thus, the particular intervention action is based on the type of non-compliance, the similarity of characteristics of the non-compliant patient with the characteristics of patients that had a successful outcome, and the commonality of the characteristics of the patients that had a successful outcome.

Figure 12:
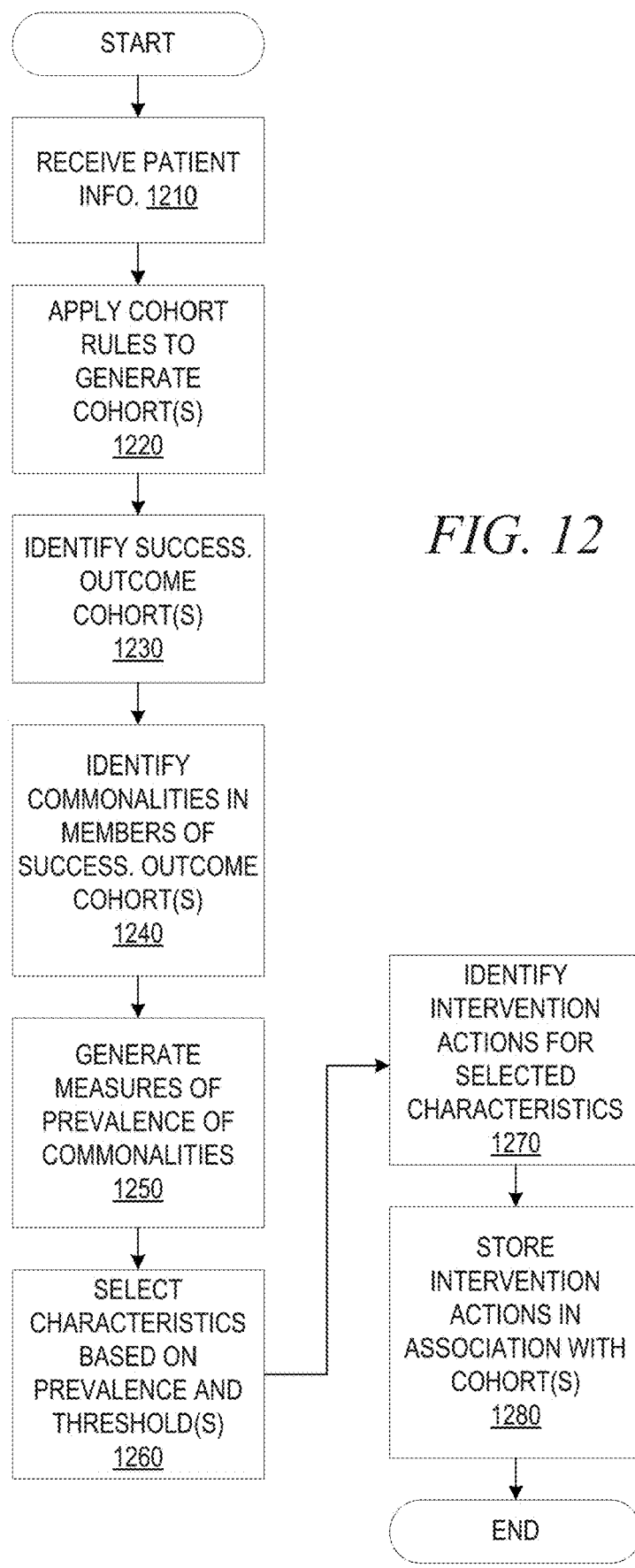
FIG. 12 is a flowchart outlining an example operation for identifying successful outcome cohorts in accordance with one illustrative embodiment.

FIG. 12 is a flowchart outlining an example operation for identifying successful outcome cohorts in accordance with one illustrative embodiment. As shown in FIG. 12, the operation starts by receiving patient information from a patient registry (step 1210) and applying cohort rules to the patient information to generate one or more cohorts of patients (step 1220). The patient cohorts are analyzed to identify successful outcome sub-cohorts for each of the one or more cohorts based on configured information indicating what a successful outcome is in the context of the cohort (step 1230). It should be appreciated that there may be multiple successful outcome sub-cohorts for each cohort based on the particular successful outcome configuration information, e.g., for the same cohort, there may be multiple different outcomes considered to be successful such as scheduling a doctor appointment, getting a particular test performed, reducing LDL cholesterol levels by a certain amount, etc.

The successful outcome sub-cohorts are analyzed to identify commonalities between characteristics in the patient information for the patients that are members of the successful outcome sub-cohorts (step 1240). A measure of prevalence of the common characteristics among the members of the successful outcome sub-cohort is generated and compared to a threshold value (step 1250). Characteristics whose prevalence meets or exceeds the threshold value are selected as representative of the members of the successful outcome sub-cohort (step 1260) and corresponding intervention actions are identified in these characteristics (step 1270). The intervention actions are stored in association with the cohort and/or successful outcome sub-cohort for later use in recommending intervention actions for non-compliant patients having similar characteristics (step 1280). The operation then terminates.

Figure 13:
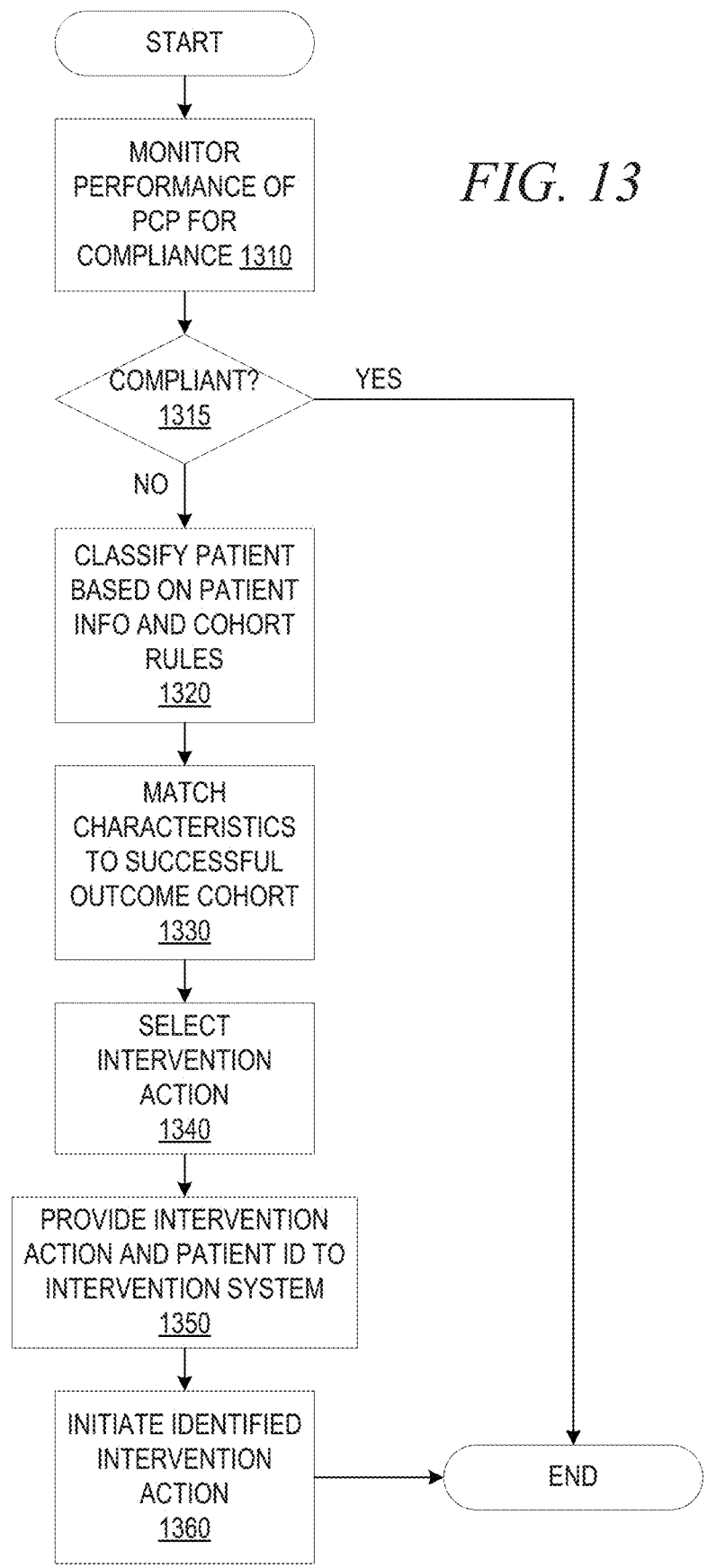
FIG. 13 is a flowchart outlining an example operation for applying an intervention action to a non-compliant patient in accordance with previously identified successful outcome sub-cohorts in accordance with one illustrative embodiment.

FIG. 13 is a flowchart outlining an example operation for applying an intervention action to a non-compliant patient in accordance with previously identified successful outcome sub-cohorts in accordance with one illustrative embodiment. As shown in FIG. 13, the operation starts by monitoring performance of a patient's personal care plan to determine compliance (or adherence) or non-compliance (or non-adherence) (step 1310). This may be done in a similar manner as described above with regard to FIG. 6, for example. If the patient is determined to be in compliance (step 1315), then the operation terminates. If the patient is determined to not be in compliance, then the patient's information is analyzed and cohort rules are applied to classify the patient into a patient cohort (step 1320).

The characteristics of the patient information are matched to a successful outcome sub-cohort associated with the patient cohort (step 1330). This matching may be based on the particular type of non-compliance identified. Moreover, this matching may be based on characteristics of the patient, e.g., gender, age, geographical location, etc. For example, the patient may be determined to be non-compliant with regard to scheduling their annual foot exam for type 2 diabetes patients. Moreover, the patient may be determined to be a 45 year old female. The patient cohort may be a cohort for type 2 diabetes patients having various successful outcome sub-cohorts, one of which is for patients that successfully scheduled their annual foot exam, that are female, and are aged 40-50. Based on the patient's non-compliance and personal characteristics, the patient is matched to the sub-cohort for patients that successfully scheduled their annual foot exam, are female, and are aged 40-50.

A corresponding intervention action associated with the successful outcome sub-cohort is selected (step 1340). As noted above, this intervention action may take many different forms depending on the implementation. In some illustrative embodiments, these intervention actions may be classified into types of campaigns, types of outreach or communication with the patient, and types of care plans or care plan elements. As will be described hereafter, in some illustrative embodiments, this intervention action may comprise one or more communications and/or a sequence of communications, selected based on the identification of the communications and/or sequence of communications that was determined to be associated with patients that are members of a corresponding successful outcome sub-cohort.

The intervention action and an identifier of the patient are provided to an intervention system (step 1350). The intervention system initiates the identified intervention action with regard to the particular patient (step 1360) and then the operation terminates. For example, the intervention system may comprise an automated electronic mail system that automatically generates electronic mail messages and sends them to electronic mail addresses associated with patients. The electronic mail messages may have predefined scripts or templates which are populated with patient information for the patient. As another example, automated telephone call systems may be utilized that automatically make telephone calls to telephone numbers associated with patients and play a pre-recorded script, possibly integrated with some patient information such as a name, physician name, etc. that is audibly output using a text-to-speech type mechanism. In some cases, the intervention system may be a human operator that manually performs actions in accordance with the intervention action. The intervention system may be separate from the other elements of the invention and in fact may be provided by a third party vendor in some cases.

Thus, in addition to the other mechanisms described above for generating and monitoring personal care plans for patients, the mechanisms of the illustrative embodiments may further apply rules to patient information to identify patient cohorts. The mechanisms of the illustrative embodiments may further identify, within these patient cohorts, other cohorts, or sub-cohorts, that are associated with patients that have had successful outcomes. The patient information for these patients having successful outcomes may be analyzed to identify commonalities that may have lead to the successful outcome. Corresponding intervention actions may be identified and associated with the cohort and/or sub-cohort. These intervention actions may then be recommended, or automatically initiate, in response to a non-compliant patient being identified and correlating the patient information of the non-compliant patient with the commonalities of the patients having had successful outcomes. In this way, intervention actions are performed to increase the likelihood that the patient will come into compliance with their personalized care plan or other health management guidelines.

Communication with Patients Based on Historical Analysis

As mentioned above, the illustrative embodiments provide mechanisms for generating personalized patient care plans, monitoring a patient's adherence or compliance with a personalized patient care plan, and determining appropriate intervention actions to take to increase the likelihood that the patient will become compliant or adhere to the personalized patient care plan if the patient becomes non-compliant or does not adhere to the patient care plan ascribed to them. In determining appropriate intervention actions to perform, if the intervention action involves a communication with the patient, which most often it will, it is desirable to communicate with the patient in a mode that is most likely going to result in the patient performing a compliance action or event so as to generate a successful outcome. A compliance action or event is one that brings the patient into compliance with the prescribed personalized patient care plan, or in greater compliance if not complete compliance with the prescribed personalized patient care plan.

As noted above, one way to identify this best mode of communication is to look at a successful outcome cohort with which the patient has similar characteristics, to identify the intervention actions (e.g., communications) associated with the successful outcome cohort, e.g., female patients aged 40-50 that are type 2 diabetics that have successfully completed their annual foot exam were contacted by electronic mail 30 days before their annual due date for their exam, with a follow-up automated phone call 3 days later. This information may be used either alone or in combination with other analysis of the patient's personal communication history, specified consents or preferences for communication, and other pattern analysis of patients having similar characteristics to that of a patient in question, to identify the best mode, or sequence of modes, for communicating with the patient that have a highest probability or likelihood of causing the patient to engage in a compliance action or event.

In some illustrative embodiments, the mechanisms of the illustrative embodiments analyze the patient's personal patient information to identify instances in the patient's history where communications were made to the patient which resulted in a subsequent compliance action or event, e.g., an email reminder message sent to the patient followed by the patient scheduling an appointment within a predetermined period of time from the date/time of the email reminder message. These instances may indicate particular communication types or particular communication workflows, as described hereafter. Instances where communications were made that did not result in a compliance action or event may also be identified as well. A measure may be calculated for each communication type, combination of communication types, communication workflows, or the like, with regard to how often the communication(s) or workflow resulted in a subsequent compliance action or event within a predetermined period of time, indicative of the subsequent compliance action or event being attributable to the corresponding communication(s) or workflow. Positive instances (where a compliance action/event occurred within the predetermined time period) may increase this measure while negative instances (where a compliance action/event did not occur within the predetermined time period) may decrease this measure. Moreover, the type of compliance action or event may be identified with regard to each measure so as to identify which communication type(s) or workflows worked best for this particular patient for influencing the patient to perform a particular compliance action or event. That is, these measures may be compared to each other to determine which communication(s) are best for which types of compliance actions/events desired.

In addition, this information may be correlated with specific preferences and consents specified in the patient information. For example, only communication modes (or types) for which the patient has given a consent to be communicated with may be considered. For those communication modes, the corresponding best modes of communication as determined from the patient's history of communications in the patient information may be selected. For example, if, for a particular type of compliance action/event desired, the best modes of communication based on the patient's history indicate electronic mail and text messaging, but the patient has only given consent to be contacted by electronic mail, then only electronic mail may be utilized even if text messaging is determined to be the relative better mode to result in the compliance action/event. Such selection may further be based on the patient's specified preferences. Thus, if the patient, in the above example, consented to both electronic mail messaging and text messaging, but has indicated a preference for text messaging, then text messaging may be selected for use in communicating with the patient to elicit the compliance action/event.

It should be appreciated that the identification of communication mode(s) to utilize for eliciting a compliance action/event from a patient may comprise identifying a sequence or pattern of communication mode(s) as well as timing of communication mode(s) and content of communications. These may be specified in communication workflows as discussed below, or as sequences or patterns of communication mode(s) occurring prior to a compliance action/event occurring within a specified time period of a communication. Thus, for example, a patient's history in the patient information may indicate that the patient received an electronic mail message followed by a text message 3 days later, and followed by a phone call 2 days after the text message. This pattern or sequence of communication mode(s) may be identified in the patient information and used as a basis for potential selection for use in eliciting a compliance action or event from the patient in a current or future situation where the patient is determined to be non-compliant.

In some illustrative embodiments, the identification of the best communication mode(s) to use to elicit a desired compliance action/event may be performed in the aggregate over a plurality of patients having similar characteristics. That is, as noted above, rules may be applied to the patient's information to categorize the patient into a patient cohort with other patients having similar characteristics, e.g., demographics, medical codes, lifestyle information, and/or the like. The patients in a same cohort as the non-compliant patient may have their patient information analyzed, in a similar manner to that of the non-compliant patient, to identify instances of communications, or sequences/patterns of communications, that have a corresponding compliance action/event within a predetermined time period of the communication(s). Again, measures may be calculated for each of the communications, or patterns/sequences of communications, and for each type of compliance action/event. These measures may be aggregated across all of the patients in the same cohort and a selected communication, or sequence/pattern of communications, may be selected for each type of compliance action/event for the cohort. This information may then be used to recommend communication mode(s) to be used with the non-compliant patient to elicit the desired compliance action/event.

It should be appreciated that in some cases, such analysis of similar patients in the same cohort may be performed with regard to successful outcome cohorts, or sub-cohorts, as opposed to the entire original cohort. That is, since these patients have already been determined to generate successful outcomes, they are more likely to indicate the best communication mode(s) for other patients having similar characteristics. Moreover, the selection of a successful outcome cohort to use may be based on the desired compliance action/event, e.g., if the desired compliance action/event is the patient scheduling their annual foot exam, then a successful outcome cohort associated with patients that have successfully scheduled their annual foot exam may be used as a basis for identifying the best communication mode(s) to utilize when interacting with a non-compliant patient having similar characteristics.

For example, the non-compliant patient may be classified into a cohort for type 2 diabetes patients that are female, aged 40-50. From within this cohort, a successful outcome cohort is defined that represents type 2 diabetes patients that are female, aged 40-50, and that have completed their annual foot exam, which it is assumed is the compliance action/event sought from the non-compliant patient. The non-complaint patient's information is analyzed as well as the patient information for patients in the successful outcome cohort to identify the best communication mode(s) identified in the non-compliant patient's information and those of similar patients in the successful outcome cohort, such as in the manner previously described above. The best communication mode(s) selected for the non-compliant patient and for the successful outcome cohort may be compared through a weighted comparison and a selection of a communication mode, or sequence/pattern of communication modes, is made. The weighting may be implementation specific. For example, in one implementation, a higher weight may be given to the communication mode(s) associated with the non-compliant patient's information as opposed to the successful outcome cohort patients, or vice versa. This weight may be applied to the corresponding measures for the communication modes, or sequence/pattern of communication modes, to generate a weighted success value for each of the communication modes, of sequence/pattern of communication modes, and a highest weighted success value communication mode or sequence/pattern is selected.

In addition to the communication modes, the illustrative embodiments may identify the more/less successful communication content for the individual non-compliant patient and/or aggregate set of patients having similar characteristics to the non-compliant patient. For example, in embodiments where the communications utilize pre-defined templates or scripts, identifiers of the templates or scripts may be maintained in the patient information along with other communication mode information. These identifiers may be used in a similar manner to the identifiers of the communication modes to identify which templates/scripts, and thus, content, of communications are more/less successful in eliciting a compliance action/event from the patient. The templates/scripts may be associated, such as via metadata associated with the template/script, with different types of personality type or emotional characteristics which may be used to identify the types of content that are more/less successful with the particular patient or group of patients. For example, the word choice in a template/script may be considered "forceful" or "friendly" or "urgent" and the patient's history information may indicate that the patient does not respond well to "forceful" communications but responds more readily to "friendly" communications. Therefore, if one wishes to elicit a compliance action/event from the patient, it is more likely to occur if a friendly content communication is utilized. This information may be combined with the selected communication mode(s) to determine a best mode and content for the communication(s) to bring the non-compliant patient into compliance.

It should be appreciated that the evaluation of content of communications is not limited to implementations where templates/scripts are utilized. To the contrary, natural language processing of the content of previous communications may be performed and keywords or key phrases may be extracted and correlated with emotional or personality characteristics so as to generate metadata associated with the communication instance. This information may be included in the patient information in association with the communication instance information so as to provide an indicator of content in the communication which can be analyzed in the manner discussed above.

Thus, illustrative embodiments are provided that include mechanisms for identifying one or more communication modes for communicating with a patient based on individual non-compliant patient information and/or aggregate analysis over a plurality of patients having similar characteristics, with regard to a history of responsiveness to different modes of communication. In addition to the patient information already discussed above, the patient information for a particular patient may include communication log data structures for tracking communications initiated with the patient including dates/times, types of communications, identifiers of particular scripts or templates used for the communications, content metadata, initiators of the communications, whether the communication resulted in a successful contact with the patient or not, and whether a subsequent compliance action or event occurred. The communication log data structures may be analyzed by the mechanisms of the illustrative embodiments to identify which modes of communication, and which types of content, are more successful with the particular non-compliant patient than others. This information may be used along with other patient information for the patient, such as communication mode preferences, communication mode consents, and the like, to select a communication mode that is most likely going to result in a compliance action or event. In some cases, while the patient may prefer one mode of communication, if the communication log data structures indicate that the patient is non-responsive to that mode of communication, an alternative mode of communication may be selected based on the communication log data structures, or "communication logs." As mentioned above, this analysis may be done in the aggregate over a plurality of patients having similar characteristics to the non-compliant patient, such as patients in a same cohort as the non-compliant patient or in a successful outcome cohort associated with the cohort in which the non-compliant patient is classified.

In some illustrative embodiments, the communication logs may store identifiers of communication workflows. A communication workflow is a set of one or more communications of the same or different communication modes and/or content, temporal information about the one or more communications, and content information specifying the type of content of the particular one or more communications, e.g., metadata indicating personality or emotional characteristics of the content. For example, a communication workflow may comprise a first email having content matching template A being sent at 7 pm on a Wednesday, an automated telephone call using script Q being made at 6 pm five days later, and a text message being sent two days later at 3 pm using a template Z. Communication workflows may be pre-defined and associated with an identifier. Thus, for example, there may be 10 different communication workflows with identifiers 1-10 and the communication logs may store this identifier in the communication log for a patient as part of the patient's information. The communication workflows may be associated with success/failure indicators indicating whether the communication workflow resulted in a responsive communication from the patient, e.g., the patient picking up the telephone, the patient replying to an electronic mail message, a read receipt from the patient being received, the patient clicking on a hyperlink in the communication or a graphical user interface element, or any other suitable indication that the patient received the communication. This information may also be correlated with patient information indicating the patient's actions thereafter with regard to scheduling an appointment with their physician, obtaining a lab test, filling a prescription for medication at a pharmacy, or any other compliance action or event.

It should be appreciated that the communication workflows identify combinations of communication modes and a temporal aspect of communication regarding an ordering of communication modes, a timing of communications, a number of times each communication mode is to be utilized, and the like. In some cases, the patient information may not specify an identifier of a specific pre-defined communication workflow. In such cases, sequence or patterns of communications modes and content may be identified through pattern analysis of the patient information. Thus, for example, an instance of an email at one date and time, followed by a phone call 2 days later, followed by a text message 3 days later, followed by a doctor's appointment being scheduled 30 days later represents a pattern of communications. Logic may be provided for identifying such patterns in patient information using temporal boundaries, e.g., communications that are within specific time frames of one another, triggering actions/events such as the compliance action/event, and the like, as basis for identifying these patterns. Hence, an ad hoc sequence or pattern identifier is provided that can identify sequences/patterns of communications without pre-defined communication workflows. These ad hoc sequences/patterns may be used either alone or in combination with communication workflow identifiers to select a best communication mode or sequence/pattern of communication modes to use to elicit the compliance action/event from the non-compliant patient. Thus, the illustrative embodiments may perform a complex evaluation to determine what particular combinations of communication modes, and what temporal sequence, to utilize for particular types of patients based on historical analysis of both individual non-compliant patient and the aggregate of similar patients.

Figure 14:
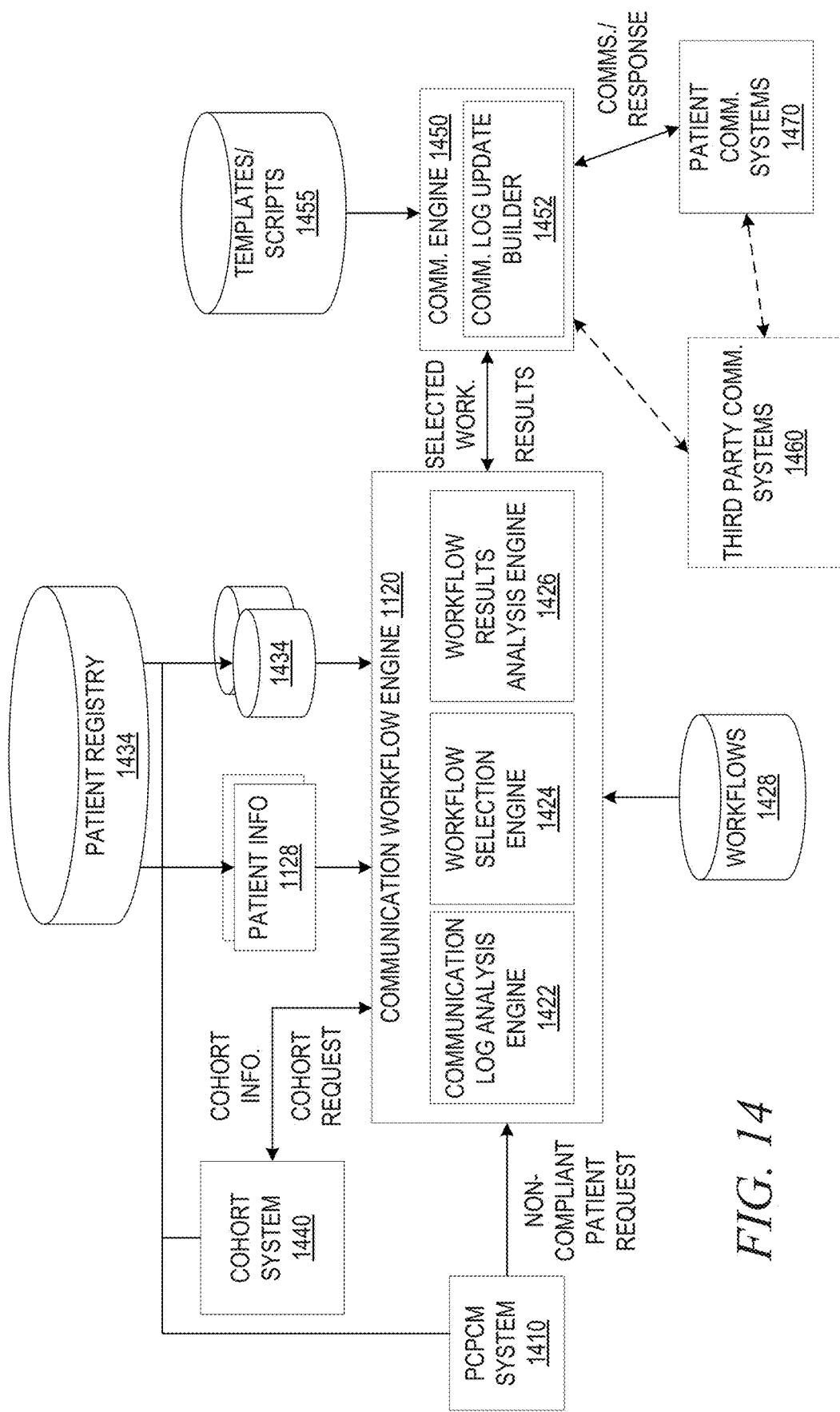
FIG. 14 is an example block diagram of the primary operational elements for selecting an optimum or best communication mode or sequence/pattern of communication modes in accordance with one illustrative embodiment.

FIG. 14 is an example block diagram of the primary operational elements for selecting an optimum or best communication mode or sequence/pattern of communication modes in accordance with one illustrative embodiment. The example shown in FIG. 14 assumes a communication workflow based implementation for purposes of illustration. However, as noted above, the illustrative embodiments do not require pre-defined communication workflows to be utilized and may in fact operate on ad hoc communication sequences/patterns identified in patient information based on pattern analysis or the like. FIG. 14 is only intended to be one example implementation and those of ordinary skill in the art will recognize that many modifications may be made to the depicted example without departing from the spirit and scope of the present invention.

As shown in FIG. 14, the primary operational elements comprise the PCPCM system 1410, a communication workflow engine 1420, a patient registry 1430, a cohort system 1440 (shown as a separate system but as noted above, may be integrated with the PCPCM system 1410 depending on the implementation), a communications engine 1450, and patient communication systems 1470. The PCPCM 1410, patient registry 1430, and cohort system 1440 all operates in the manner previously described above. In addition, these elements interface with the communication workflow engine 1420 to facilitate operations for selecting one or more communication modes for contacting a non-compliant patient to elicit a compliance action/event. In particular, the PCPCM system 1410 provides information regarding non-compliant patients to the communication workflow engine 1420, the cohort system 1440 provides information regarding cohort association with regard to a non-compliant patient, and the patient registry 1430 provides patient information 1432 and communication logs 1434 for the non-compliant patient and other patients, such as those in an associated cohort, to the communication workflow engine 1420 for use in selecting a communication workflow to use to communicate with the non-compliant patient.

Moreover, the communication workflow engine 1420 interfaces with communication engine 1450 to facilitate the sending of communications, in accordance with a selected communication workflow, to patient communication systems 1470 and receive responses back from the patient systems 1470. In addition, the communication engine 1450 provides information back to the communication workflow engine 1420 to update communication logs 1434 associated with patient information 1432 in the patient register 1430.

In operation, the PCPCM system 1410 may identify a non-compliant patient, e.g., a patient that is not following their prescribed patient care plan, has failed to keep an appointment, or any other event that causes the patient to not be in compliance with prescribed treatments for curing or managing their medical condition. The PCPCM system 1410 may send a request message to the communication workflow engine 1420 indicating the identifier of the non-compliant patient and the nature of the failure to comply, e.g., an identifier of the type of compliance action/event that is desired from the non-compliant patient. The communication workflow engine 1420 sends a request for patient information 1432 and communication log information 1434 to the registry 1430 as well as a request for cohort information from the cohort system 1440. The patient registry 1430 provides the patient information 1432 and communication logs 1434. The cohort system 1440 provides information as to the cohorts associated with the non-compliant patient identified in the request message from the PCPCM system 1410. The communication workflow engine 1420 sends a request to the patient registry 1430 for patient information 1432 and communication logs 1434 for patients in the cohorts associated with the non-compliant patient.

The communication log analysis engine 1422 of the communication workflow engine 1420 analyzes the communication logs 1434 of the non-compliant patient and the patients in the associated cohorts to identify instances of communication workflows and their associated success/failure conditions with regard to the particular type of compliance action/event desired as specified in the request message from the PCPCM system 1410. Measures of success/failure of the various communication workflows are calculated, possibly weighting different success/failure values for different communication workflows depending on the implementation. For example, weights may be applied based on preferences, consents, or other information in the non-compliant patient's patient information to prefer some communication modes and/or communication workflows over others. In some cases, greater weight is given to communications or sequences/patterns that are more recent as opposed to those that are more temporally remote from the present date/time. Other weighting schemes may likewise be used, such as default weights set according to subject matter expert determinations, or the like.

The workflow selection engine 1424 selects a communication workflow based on the calculated success/failure measures, retrieves the corresponding communication workflow from the workflows database 1428, and provides the selected communication workflow to the communications engine 1450. The selected communication workflow is used by the communication engine 1450 to retrieve corresponding templates/scripts for the communications in the communication workflow from the templates/script database 1455. The retrieved templates/scripts are optionally customized based on patient information 1432 for the non-compliant patient to generate one or more communications to be sent to patient communication systems 1470 associated with the non-compliant patient using communication information (telephone numbers, email addresses, text message identifiers, etc.) specified in the patient's information 1432. These communications are sent using the particular communication mode(s) specified in the selected communication workflow at the specified times indicated in the selected communication workflow. Alternatively, these communications may be performed by third party communication providers 1460, such as companies that specialized in large scale automated calls, electronic mail distributions, text messaging, or the like.

The communication engine 1450 monitors the communications for results and communication log update building logic 1452 builds a communication log update based on the results. For example, the monitoring of the communications may indicate whether the results of the communications with the patient communication systems 1470 may indicate a hang-up on the call, busy signal, answering machine pickup, auto-responder email response, email delivery failure, read receipt received, response text, user selecting a graphical user interface element (such as a virtual button or the like), or any other response that can be provided in response to a particular type of communication. This information may be added to a communication log update data structure that is provided back to the communication workflow engine 1420 in response to the workflow being completed.

The workflow results analysis engine 1426 analyzes the communication log update data structure to identify communication log updates to be applied to the communication logs 1434 of the non-compliant patient. For example, the workflow results analysis engine 1426 may analyze the various responses captured by the communication log update builder logic 1452 and determines whether these represent success/failure of the particular communication mode, communication content, and/or sequence/pattern of communications. The communication logs 1434 are then updated with the identifier of the communication workflow utilized, the date/time of the communication workflow selection and/or completion, and the success/failure of the communication workflow. Of course, this could also be done on an individual communication mode basis as well. In this way, the communication logs 1434 of the non-compliant patient are updated to reflect the most recent communication workflow attempt and thereby influence future communication workflow selections.

The PCPCM system 1410 may continue to monitor the patient registry 1420 to determine if updates to the patient information 1432 indicate a compliance action/event occurring within a specified time period of the most recent communication workflow selection/completion. The time period may be a predetermined time period which is a default or which his specific to the type of compliance action/event. If such a compliance action/event is identified, then the patient may be evaluated to be in compliance. If such a compliance action/event is not identified, then the patient may continue to be considered non-compliant and the operation to select another communication workflow may be performed again to again try to attempt to bring the patient into compliance.

Figure 15:
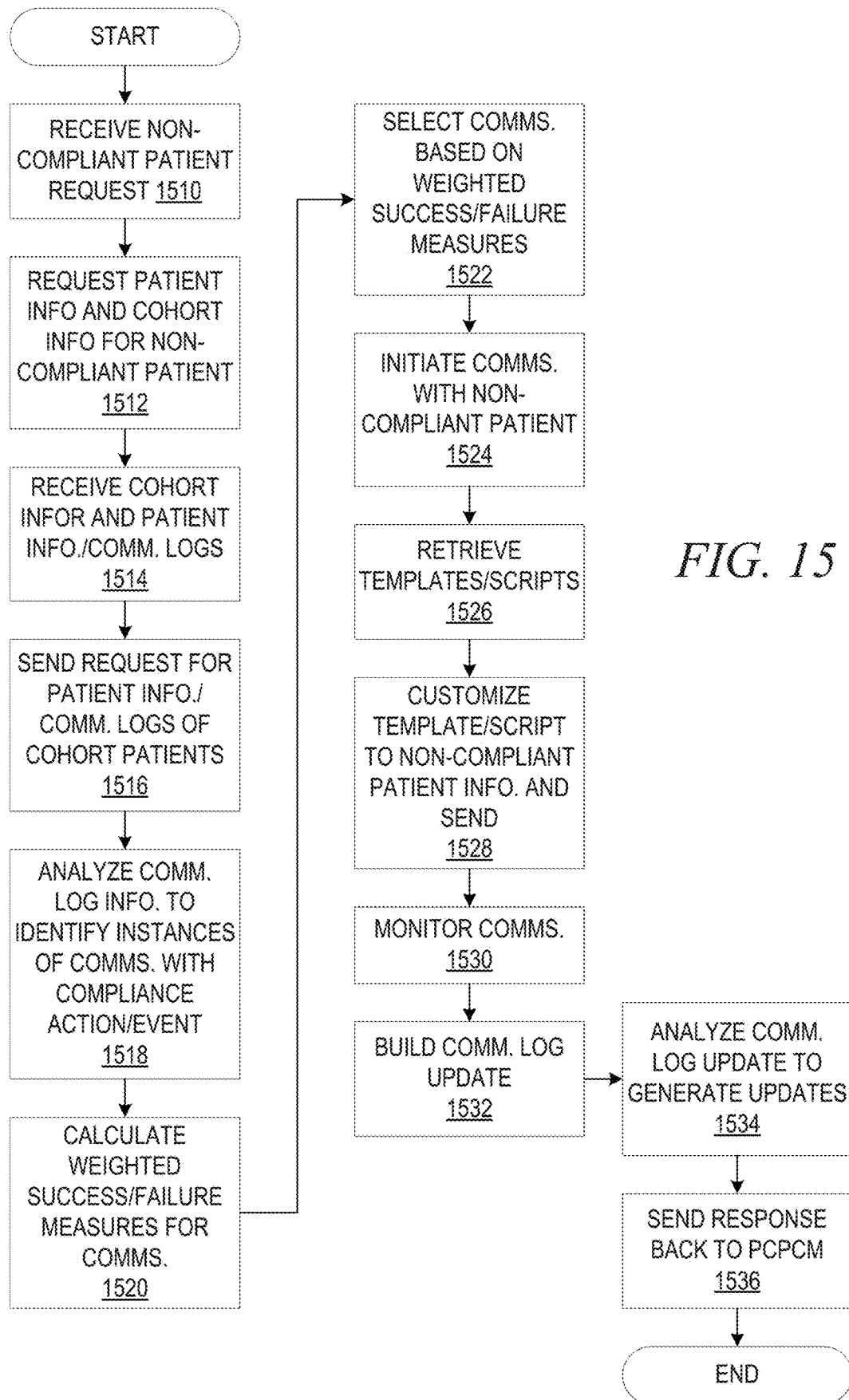
FIG. 15 is a flowchart outlining an example operation for selecting a best mode or sequence/pattern of communication modes in accordance with one illustrative embodiment.

FIG. 15 is a flowchart outlining an example operation for selecting a best mode or sequence/pattern of communication modes in accordance with one illustrative embodiment. The operation outlined in FIG. 15 may be performed, for example, by a communication workflow engine, such as communication workflow engine 1420 in FIG. 14, for example.

The communication workflow engine receives a request message identifying a non-compliant patient and a desired compliance action/event (step 1510). The communication workflow engine sends requests for patient information and cohort information to the patient registry and cohort systems (step 1512). The communication workflow engine receives the cohort information and patient information/communication logs for the non-compliant patient (step 1514) and sends a request for patient information and communication log information for patients in the identified cohorts (step 1516).

The communication log information is analyzed to identify instances of communications of sequences/patterns of communications associated with the compliance action/event sought as specified in the request message (step 1518). Weighted success/failure measures are calculated for the various communications or sequence/patterns of communications (step 1520). A communication or sequence/pattern of communications is selected based on the weighted success/failure measures (step 1522). The selected communication(s) are then used as a basis for initiating communications with the non-compliant patient (step 1524).

Corresponding templates/scripts are retrieved from a template/script database (step 1526) and optionally customized based on patient information for the non-compliant patient to generate one or more communications to be sent to communication systems associated with the non-compliant patient using communication information (telephone numbers, email addresses, text message identifiers, etc.) specified in the patient's information (step 1528).

The communications sent as part of the selected communication(s) are monitored to determine if the patient responds to the communications (step 1530). A communication log update is built based on the monitoring of the responses, if any, to indicate the success/failure of the communications (step 1532). This communication log update is analyzed to generate an update to the communication log for the non-compliant patient (step 1534) and a response is sent back to the PCPCM system indicating whether the patient responded or not (step 1536). The operation then terminates.

It should be appreciated that the PCPCM system may further monitor the patient information in the patient register 1430 to determine if there is any subsequent compliance action/event performed by the non-compliant patient to determine if the patient has come into compliance. If so, the patient may be re-classified as being a compliant patient. If not, then the process above may be repeated as the patient is still non-compliant. However, since the communication logs have been updated, the measures of success/failure may be adjusted so as to be less likely to select the same modes of communication or sequence/pattern of communications, communication workflow, and/or content of communications for subsequent communication operations.

Thus, the illustrative embodiments further provide mechanisms for selecting communication modes, sequences or patterns of communication modes, and communication content for communicating with non-compliant patients to attempt to bring them in compliance with their personalized patient care plans, treatments, or the like. The illustrative embodiments may look at the communication history of the non-compliant patient and patients having similar characteristics. Moreover, weighted calculations of success/failure of previous communications may be used to calculated values for selection of communication modes to be used. Furthermore, the selection may be based on the particular type of compliance action/event desired to be elicited from the non-compliant patient.

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output or I/O devices (including but not limited to keyboards, displays, pointing devices, etc.) can be coupled to the system either directly or through intervening I/O controllers. Network adapters may also be coupled to the system to enable the data processing system to become coupled to other data processing systems or remote printers or storage devices through intervening private or public networks. Modems, cable modems and Ethernet cards are just a few of the currently available types of network adapters.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system comprising a processor and a memory, for monitoring treatment of patients, comprising:

executing, by the data processing system, instructions loaded into the memory to configure the data processing system to implement a cohort classification engine, a cohort successful outcome analysis engine, and a cohort rules database, and a medical care intervention analysis system;

generating, by the data processing system, a patient registry comprising a plurality of patient registry records, each patient registry record being associated with a corresponding patient and comprising attributes specifying personal and medical information about the corresponding patient;

generating, by the cohort classification engine executing on the data processing system, a cohort of corresponding patients by executing cohort rides from the cohort rules database on attributes of corresponding patients specified in the patient registry records, wherein the cohort rules specify one or more trigger attributes indicating patient attributes of patients that are considered to be members of a corresponding cohort and generating the cohort comprises, for each corresponding patient and for each cohort rule, adding the corresponding patient to a cohort corresponding to the cohort rule in response to trigger attributes of the cohort rule being triggered by the attributes of those corresponding patients;

analyzing, by the cohort successful outcome analysis engine executing on the data processing system, the medical information in the patient registry records of the patient registry corresponding to patients classified in the cohort, to identify a successful outcome sub-cohort, wherein the successful outcome sub-cohort comprises one or more of the corresponding patients classified into the cohort whose medical information indicates a successful outcome based on a configuration parameter of the cohort successful outcome analysis engine specifying criteria indicating a successful outcome, wherein a successful outcome is a behavior, action, or activity that a corresponding patient engages in that brings the corresponding patient into compliance with a personalized patient care plan assigned to the corresponding patient;

determining, by the medical care intervention analysis system executing on the data processing system, at least one patient management operation for a current patient classified in the cohort, based on at least one of the successful outcomes associated with corresponding patients in the sub-cohort, wherein the at least one patient management operation comprises transmitting one or more communications to one or more patient communication devices associated with the current patient in accordance with a communication campaign associated with the successful outcome; and transmitting, by a communications system associated with the data processing system, the one or more communications to the one or more patient communication devices associated with the current patient, wherein determining at least one patient management operation comprises:
  analyzing the successful outcomes associated with corresponding patients in the sub-cohort to identify different patient management operations associated with the successful outcomes and corresponding numbers of corresponding patients in the sub-cohort with which each different patient management operation is associated;
  determining, for each patient management operation, a measure of prevalence of the patient management operation in the sub-cohort based on results of the analysis;
  comparing the measure of prevalence for each patient management operation to a threshold prevalence value; and
  determining the at least one patient management operation based on results of the comparison, wherein only patient management operations having a corresponding measure of prevalence that has a predetermined relationship to the threshold prevalence value are selected to be part of the at least one patient management operation.

2. The method of claim 1, wherein generating the cohort of corresponding patients based on attributes of the patient registry records associated with corresponding patients comprises identifying patients having a similar medical condition specified in the attributes of the patient registry records as being part of a same cohort.

3. The method of claim 1, wherein the attributes of the patient registry records comprise medical codes corresponding to one or more of a medical diagnosis, medical symptoms, or medical treatment.

4. The method of claim 1, wherein a patient identified in a patient registry record of the patient registry is a member of more than one cohort of one or more cohorts.

5. The method of claim 1, wherein analyzing the medical information to identify a successful outcome cohort comprises identifying an instance of a treatment in the medical information followed by information in the patient registry record indicating the presence of a pre-defined desired result.

6. The method of claim 5, wherein the pre-defined desired result is one of a corresponding patient performing a pre-defined action solicited by the instance of the treatment or a medical condition of the corresponding patient improving.

7. The method of claim 5, wherein the pre-defined desired result is an action or behavior of the corresponding patient that causes the corresponding patient to be in compliance with a predefined personalized patient care plan associated with the corresponding patient.

8. The method of claim 1, wherein determining at least one patient management operation for the current patient based on the successful outcomes associated with corresponding patients in the sub-cohort comprises determining the at least one patient management operation based on a subset of one or more characteristics common to patients associated with the sub-cohort for which the at least one patient management operation was performed.

9. The method of claim 1, wherein the one or more communications comprises a sequence of communications to send to the patient at specified time intervals between communications.

10. A computer program product comprising a non-transitory computer readable medium having a computer readable program stored therein, wherein the computer readable program, when executed on a computing device, causes the computing device to:
  execute instructions loaded into the memory to configure the computing device to implement a cohort classification engine, a cohort successful outcome analysis engine, and a cohort rules database, and a medical care intervention analysis system;
  generate a patient registry comprising a plurality of patient registry records, each patient registry record being associated with a corresponding patient and comprising attributes specifying personal and medical information about the corresponding patient;
  generate, by the cohort classification engine, a cohort of corresponding patients by executing cohort rules from the cohort rules database on attributes of corresponding patients specified in the patient registry records, wherein the cohort rules specify one or more trigger attributes indicating patient attributes of patients that are considered to be members of a corresponding cohort and generating the cohort comprises, for each corresponding patient and for each cohort rule, adding the corresponding patient to a cohort corresponding to the cohort rule in response to trigger attributes of the cohort rule being triggered by the attributes of those corresponding patients;

analyze, by the cohort successful outcome analysis engine, the medical information in the patient registry records of the patient registry corresponding to patients classified in the cohort, to identify a successful outcome sub-cohort, wherein the successful outcome sub-cohort comprises one or more of the corresponding patients classified into the cohort whose medical information indicates a successful outcome based on a configuration parameter of the cohort successful outcome analysis engine specifying criteria indicating a successful outcome, wherein a successful outcome is a behavior; action, or activity that a corresponding patient engages in that brings the corresponding patient into compliance with a personalized patient care plan assigned to the corresponding patient;

determine, by the medical care intervention analysis system, at least one patient management operation for a current patient classified in the cohort, based on at least one of the successful outcomes associated with corresponding patients in the sub-cohort, wherein the at least one patient management operation comprises transmitting one or more communications to one or more patient communication devices associated with the current patient in accordance with a communication campaign associated with the successful outcome; and transmit, by a communications system, the one or more communications to the one or more patient communication devices associated with the current patient, wherein determining at least one patient management operation comprises:

analyzing the successful outcomes associated with corresponding patients in the sub-cohort to identify different patient management operations associated with the successful outcomes and corresponding numbers of corresponding patients in the sub-cohort with which each different patient management operation is associated;

determining, for each patient management operation, a measure of prevalence of the patient management operation in the sub-cohort based on results of the analysis;

comparing the measure of prevalence for each patient management operation to a threshold prevalence value; and determining the at least one patient management operation based on results of the comparison, wherein only patient management operations having a corresponding measure of prevalence that has a predetermined relationship to the threshold prevalence value are selected to be part of the at least one patient management operation.

11. The computer program product of claim 10, wherein the computer readable program causes the computing device to generate the cohort of corresponding patients based on attributes of the patient registry records associated with corresponding patients at least by identifying patients having a similar medical condition specified in the attributes of the patient registry records as being part of a same cohort.

12. The computer program product of claim 10, wherein the attributes of the patient registry records comprise medical codes corresponding to one or more of a medical diagnosis, medical symptoms, or medical treatment.

13. The computer program product of claim 10, wherein a patient identified in a patient registry record of the patient registry is a member of more than one cohort of one or more cohorts.

14. The computer program product of claim 10, wherein the computer readable program causes the computing device to analyze the medical information to identify a successful outcome cohort at least by identifying an instance of a treatment in the medical information followed by information in the patient registry record indicating the presence of a pre-defined desired result.

15. The computer program product of claim 14, wherein the pre-defined desired result is one of a corresponding patient performing a pre-defined action solicited by the instance of the treatment or a medical condition of the corresponding patient improving.

16. The computer program product of claim 14, wherein the pre-defined desired result is an action or behavior of the corresponding patient that causes the corresponding patient to be in compliance with a predefined personalized patient care plan associated with the corresponding patient.

17. The computer program product of claim 10, wherein the computer readable program causes the computing device to determine at least one patient management operation for the current patient based on the successful outcomes associated with corresponding patients in the sub-cohort at least by determining the at least one patient management operation based on a subset of one or more characteristics common to patients associated with the sub-cohort for which the at least one patient management operation was performed.

18. An apparatus comprising:
a processor; and
a memory coupled to the processor, wherein the memory comprises instructions which, when executed by the processor, cause the processor to:
execute instructions loaded into the memory to configure the processor to implement a cohort classification engine, a cohort successful outcome analysis engine, and a cohort rules database, and a medical care intervention analysis system;
generate a patient registry comprising a plurality of patient registry records, each patient registry record being associated with a corresponding patient and comprising attributes specifying personal and medical information about the corresponding patient;
generate, by the cohort classification engine, a cohort of corresponding patients by executing cohort rules from the cohort rules database on attributes of corresponding patients specified in the patient registry records, Wherein the cohort rules specify one or more trigger attributes indicating patient attributes of patients that are considered to be members of a corresponding cohort and generating the cohort comprises, for each corresponding patient and for each cohort rule, adding the corresponding patient to a cohort corresponding to the cohort rule in response to trigger attributes of the cohort rule being triggered by the attributes of those corresponding patients;
analyze, by the cohort successful outcome analysis engine, the medical information in the patient registry records of the patient registry corresponding to patients classified in the cohort, to identify a successful outcome sub-cohort, wherein the successful outcome sub-cohort comprises one or more of the corresponding patients classified into the cohort whose medical information indicates a successful outcome based on a configuration parameter of the cohort successful outcome analysis engine specifying criteria indicating a successful outcome, wherein a successful outcome is a behavior, action, or activity that a corresponding patient engages in that brings the corresponding patient into compliance with a personalized patient care plan assigned to the corresponding patient;

determine, by the medical care intervention analysis system, at least one patient management operation for a current patient classified in the cohort, based on at least one of the successful outcomes associated with corresponding patients in the sub-cohort, wherein the at least one patient management operation comprises transmitting one or more communications to one or more patient communication devices associated with the current patient in accordance with a communication campaign associated with the successful outcome; and transmit, by a communications system, the one or more communications to the one or more patient communication devices associated with the current patient, wherein determining at least one patient management operation comprises:

analyzing the successful outcomes associated with corresponding patients in the sub-cohort to identify different patient management operations associated with the successful outcomes and corresponding numbers of corresponding patients in the sub-cohort with which each different patient management operation is associated;

determining, for each patient management operation, a measure of prevalence of the patient management operation in the sub-cohort based on results of the analysis, comparing the measure of prevalence for each patient management operation to a threshold prevalence value; and determining the at least one patient management operation based on results of the comparison, wherein only patient management operations having a corresponding measure of prevalence that has a predetermined relationship to the management operation.

\* \* \* \* \*